US007381381B2

(12) United States Patent
Lee et al.

(10) Patent No.: US 7,381,381 B2
(45) Date of Patent: Jun. 3, 2008

(54) AIR TREATMENT APPARATUS HAVING AN INTERSTITIAL ELECTRODE OPERABLE TO AFFECT PARTICLE FLOW

(75) Inventors: Jim L. Lee, Rohnert Park, CA (US); Charles E. Taylor, Punta Gorda, FL (US); Shek Fai Lau, Foster City, CA (US)

(73) Assignee: Sharper Image Corporation, San Francisco, CA (US)

( * ) Notice: Subject to any disclaimer, the term of this patent is extended or adjusted under 35 U.S.C. 154(b) by 556 days.

(21) Appl. No.: 10/405,193

(22) Filed: Apr. 1, 2003

(65) Prior Publication Data

US 2004/0033176 A1    Feb. 19, 2004

Related U.S. Application Data

(63) Continuation-in-part of application No. 10/074,207, filed on Feb. 12, 2002, now abandoned.

(60) Provisional application No. 60/369,554, filed on Apr. 1, 2002.

(51) Int. Cl.
 *B01J 19/08* (2006.01)
(52) U.S. Cl. ........................ 422/186.04; 96/95; 96/98

(58) Field of Classification Search ........... 422/186.04; 96/95, 98
See application file for complete search history.

(56) References Cited

U.S. PATENT DOCUMENTS

| 4,673,416 A | * | 6/1987 | Sakakibara et al. ............ 96/79 |
| 4,689,056 A | * | 8/1987 | Noguchi et al. ................ 96/79 |
| 4,789,801 A | * | 12/1988 | Lee ............................. 310/308 |
| 6,176,977 B1 | * | 1/2001 | Taylor et al. ................ 204/176 |

* cited by examiner

*Primary Examiner*—Kishor Mayekar
(74) *Attorney, Agent, or Firm*—Bell, Boyd & Lloyd LLP

(57) ABSTRACT

An electro-kinetic air conditioner for removing particulate from the air creates an airflow using no moving parts. The conditioner includes an ion generator that has an electrode assembly including a first array of emitter electrodes, a second array of collector electrodes, and a high voltage generator. Preferably, a third or leading or focus electrode is located upstream of the first array of emitter electrodes, and/or a trailing electrode is located downstream of the second array of collector electrodes. The device can also include an interstitial electrode located between collector electrodes, an enhanced collector electrode with an integrally formed trailing end, and an enhanced emitter electrode with an enhanced length in order to increase emissivity.

44 Claims, 37 Drawing Sheets

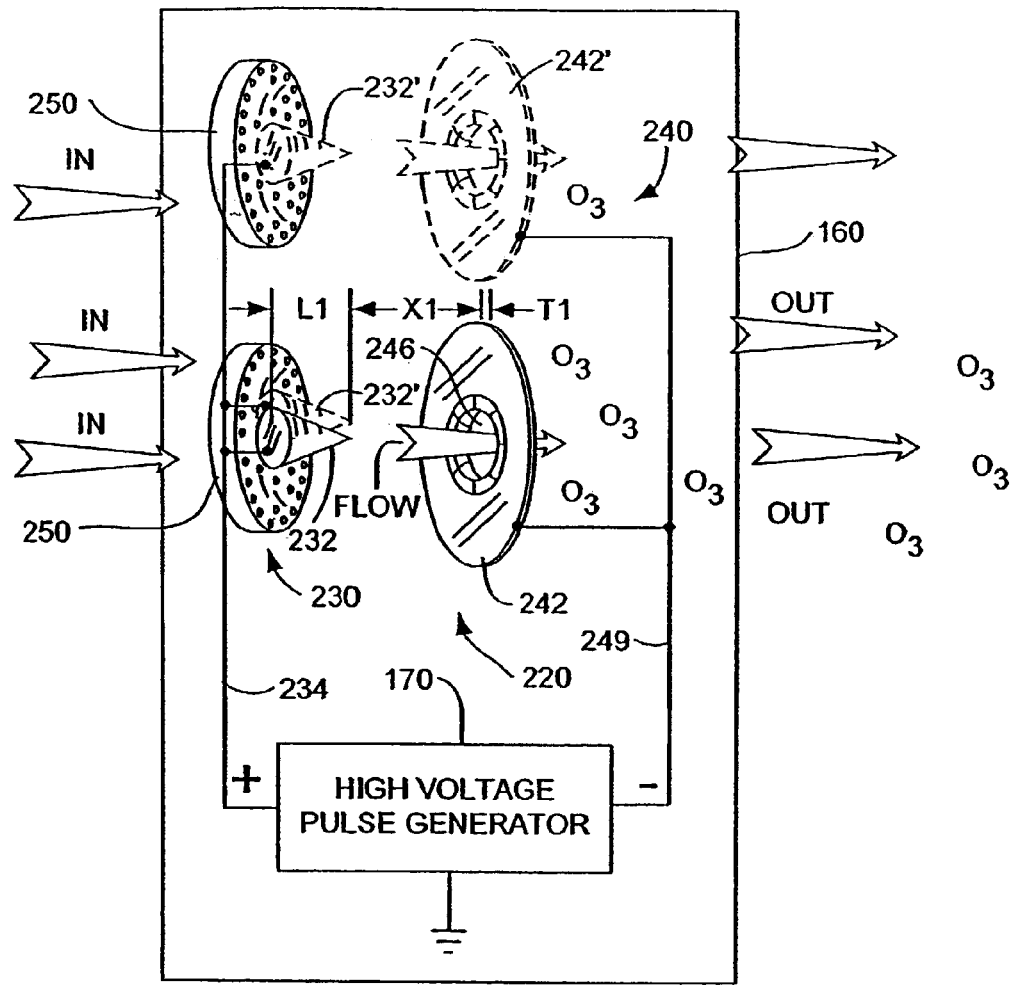
FIG. - 9A
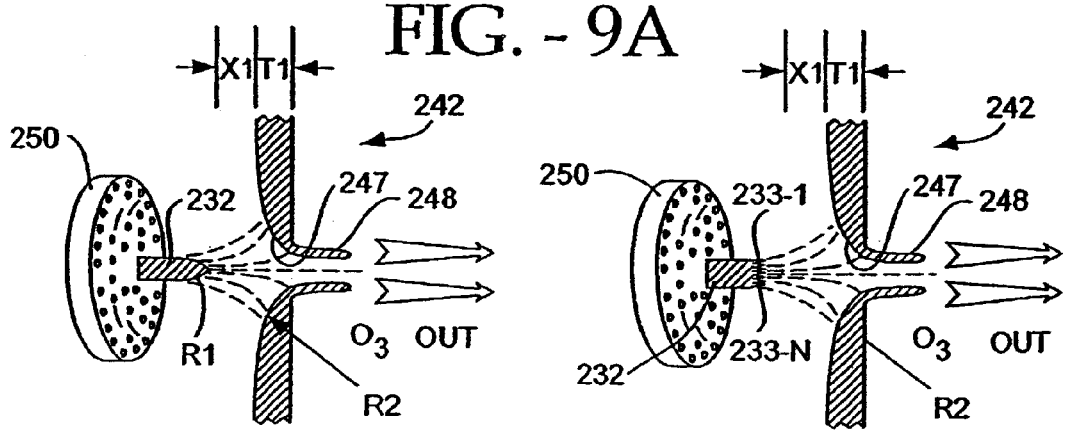
FIG. - 9B  FIG. - 9C

AIR TREATMENT APPARATUS HAVING AN INTERSTITIAL ELECTRODE OPERABLE TO AFFECT PARTICLE FLOW

CLAIM OF PRIORITY

This application claims priority from U.S. Provisional Patent Application entitled "METHOD FOR INCREASING PERFORMANCE OF ION WIND DEVICES," Ser. No. 60/369,554, filed Apr. 1, 2002 under 35 U.S.C. 119(e), which application is incorporated in its entirety herein by reference. This application claims priority to and is a continuation-in-part of U.S. patent application Ser. No. 10/074,207, filed Feb. 12, 2002 now abandoned. This application claims priority to and is a continuation-in-part of U.S. patent application Ser. No. 10/074,096, filed Feb. 12, 2002, now U.S. Pat. No. 6,974,560, which is a continuation-in-part of U.S. Pat. application Ser. No. 09/924,624, filed Aug. 8, 2001 now abandoned, which is a continuation of U.S. patent application Ser. No. 09/564,960, filed May 4, 2000, now U.S. Pat. No. 6,350,417, which is a continuation-in-part of U.S. patent application Ser. No. 09/186,471, filed Nov. 5, 1998, now U.S. Pat. No. 6,176,977.

FIELD OF THE INVENTION

The present invention relates generally to devices that produce an electro-kinetic flow of air from which particulate matter is substantially removed.

BACKGROUND OF THE INVENTION

The use of an electric motor to rotate a fan blade to create an airflow has long been known in the art. Unfortunately, such fans produce substantial noise, and can present a hazard to children who may be tempted to poke a finger or a pencil into the moving fan blade. Although such fans can produce substantial airflow (e.g., 1,000 ft$^3$/minute or more), substantial electrical power is required to operate the motor, and essentially no conditioning of the flowing air occurs.

It is known to provide such fans with a HEPA-compliant filter element to remove particulate matter larger than perhaps 0.3 μm. Unfortunately, the resistance to airflow presented by the filter element may require doubling the electric motor size to maintain a desired level of airflow. Further, HEPA-compliant filter elements are expensive, and can represent a substantial portion of the sale price of a HEPA-compliant filter-fan unit. While such filter-fan units can condition the air by removing large particles, particulate matter small enough to pass through the filter element is not removed, including bacteria, for example.

It is also known in the art to produce an airflow using electro-kinetic techniques, by which electrical power is converted into a flow of air without mechanically moving components. One such system is described in U.S. Pat. No. 4,789,801 to Lee (1988), depicted herein in simplified form as FIGS. 1A and 1B and which patent is incorporated herein by reference. System 10 includes an array of first ("emitter") electrodes or conductive surfaces 20 that are spaced-apart symmetrically from an array of second ("collector") electrodes or conductive surfaces 30. The positive terminal of a generator such as, for example, pulse generator 40 that outputs a train of high voltage pulses (e.g., 0 to perhaps +5 KV) is coupled to the first array, and the negative pulse generator terminal is coupled to the second array in this example. It is to be understood that the arrays depicted include multiple electrodes, but that an array can include or be replaced by a single electrode.

The high voltage pulses ionize the air between the arrays, and create an airflow 50 from the first array toward the second array, without requiring any moving parts. Particulate matter 60 in the air is entrained within the airflow 50 and also moves towards the second electrodes 30. Much of the particulate matter is electrostatically attracted to the surfaces of the second electrodes, where it remains, thus conditioning the flow of air exiting system 10. Further, the high voltage field present between the electrode arrays can release ozone into the ambient environment, which can eliminate odors that are entrained in the airflow.

In the particular embodiment of FIG. 1A, first electrodes 20 are circular in cross-section, having a diameter of about 0.003" (0.08 mm), whereas the second electrodes 30 are substantially larger in area and define a "teardrop" shape in cross-section. The ratio of cross-sectional radii of curvature between the bulbous front nose of the second electrode and the first electrodes exceeds 10:1. As shown in FIG. 1A, the bulbous front surfaces of the second electrodes face the first electrodes, and the somewhat "sharp" trailing edges face the exit direction of the airflow. The "sharp" trailing edges on the second electrodes promote good electrostatic attachment of particulate matter entrained in the airflow.

In another particular embodiment shown herein as FIG. 1B, second electrodes 30 are symmetrical and elongated in cross-section. The elongated trailing edges on the second electrodes provide increased area upon which particulate matter entrained in the airflow can attach.

While the electrostatic techniques disclosed by the '801 patent are advantageous over conventional electric fan-filter units, further increased air transport-conditioning efficiency would be advantageous.

Ion wind devices such as those described in U.S. Pat. No. 4,789,801 provide accelerated gas ions generated by the use of differential high voltage electric fields between an array of one or more emitters and a plurality of collectors (accelerators). The ions are entrained in the ambient bulk gases, causing the gases to flow. Gas velocities can reach as high as eight hundred feet per minute. However, the high voltage electric fields used to generate the gas ions and provide the force necessary for gas acceleration are also responsible for creating molecular disassociation reactions, the most common of which include ozone generated from oxygen when such devices are operating in a breathable atmosphere. The U.S. Food and Drug Administration has determined that indoor, airborne ozone in concentrations above 50 ppb (parts per billion) may be hazardous to humans. NIOSH (National Institute of Occupational Safety and Health) has ruled that indoor concentrations of ozone above 100 ppb may be hazardous to humans. Devices which utilize high voltage electric fields to generate atmospheric plasma, corona discharge and air ions, are all susceptible to generating this allotropic of oxygen, ozone. There exists a linear relationship between the level of the high voltage fields and current and the level of ozone concentration in most direct current operated ion wind systems. Also, a linear relationship exists between the acceleration velocity and intensity of the electric fields. Typically, the higher the voltage the higher the acceleration. Since it is desired to have maximum acceleration, methods must be employed to reduce ozone production or convert unwanted ozone back to oxygen before it is expelled into the breathable atmosphere. It is an object of this invention to provide methods to convert generated ozone back to oxygen in such devices.

Ion wind devices that have been specifically designed as air cleaners have also been inherently limited in their airflow and in the amount of particle contamination they can remove. Unlike electrostatic air cleaners that rely upon a motor driven fan to propel air into an ionizing field, the ion wind device utilizes a structured ionizing field as the primary air movement force. This requires molecular ionization levels at many orders of magnitude greater than are used in electrostatic precipitator devices. Consequently, like-charged particles and matter clustered in the air stream inhibit some airflow and precipitation ability of ion wind devices. It is a further object of this invention to teach a method and apparatus for de-ionizing a large portion of the charged molecules responsible for the resisting forces in the air stream and to improve precipitation efficiency of the charged contaminant particles by accelerating them towards an oppositely charged collector plate array.

SUMMARY OF THE INVENTION

The present invention provides such an apparatus.

One aspect of the present invention is to provide an electro-kinetic air transporter-conditioner that produces an enhanced airflow velocity, enhanced particle collection, and an appropriate amount of ozone production.

An embodiment includes one or more focus or leading electrodes. Each focus or leading electrode may be located upstream to, or even with, each first electrode. The focus or leading electrodes assists in controlling the flow of ionized particles within the airflow. The focus or leading electrode shapes the electrostatic field generated by each first electrode within the electrode assembly.

Another embodiment includes one or more trailing electrodes. Each trailing electrode can be located downstream of a second electrode. The trailing electrode can assist in neutralizing the amount of ions exiting this embodiment of the invention, and can further assist in collecting ionized particles. The trailing electrode can alternatively enhance the flow of negative ions from the transporter-conditioner. Additionally, the trailing electrodes can improve the laminar flow properties of the airflow exiting the air transporter-conditioner.

Another embodiment of the invention includes at least one interstitial electrode located between two second electrodes. The interstitial electrode can also assist in the collection of particulate matter by the second electrodes.

In yet another embodiment of the invention, one or more of the second electrodes are formed to have an enhanced protective end or trailing surface which assists in the operation and cleaning of the embodiment.

In still a further embodiment of the invention, one or more first electrode are of enhanced length in order to increase the emissivity of the first electrode.

Other objects, aspects, features and advantages of the invention will appear from the following description in which the preferred embodiments have been set forth in detail, in conjunction with the accompanying drawings and also from the following claims.

BRIEF DESCRIPTION OF THE DRAWINGS

FIG. 1A is a plan, cross-sectional view, of a first embodiment of an electro-kinetic air transporter-conditioner system according to the prior art; FIG. 1B is a plan, cross-sectional view, of a second embodiment of an electro-kinetic air transporter-conditioner system according to the prior art;

FIG. 2A is a perspective view of a typical embodiment of the housing of an electro-kinetic air transporter-conditioner; FIG. 2B is a perspective view of the embodiment shown in FIG. 2A illustrating the removable second electrodes;

FIG. 4A is a perspective view showing an embodiment of an electrode assembly according to the present invention; FIG. 4B is a plan view of the embodiment illustrated in FIG. 4A; FIG. 4C is a perspective view showing another embodiment of an electrode assembly according to the present invention; FIG. 4D is a plan view illustrating a modified version of the embodiment of FIG. 4C; FIG. 4E is a perspective view showing yet another embodiment of an electrode assembly according to the present invention; FIG. 4F is a plan view of the embodiment of FIG. 4E;

FIG. 5A is a perspective view of still another embodiment of the present invention illustrating the leading or focus electrode added to the embodiment shown in FIG. 4A; FIG. 5B is a plan view of a modified embodiment of the present invention similar to that shown in FIG. 5A illustrating a protective end on each second electrode;

FIG. 6A is a perspective view of a further embodiment of the present invention, illustrating a leading or focus electrode added to the embodiment shown in FIG. 4C; FIG. 6B is a perspective view of a modified embodiment of the present invention as shown in FIG. 6A; FIG. 6C is a perspective view of a modified embodiment of the present invention as shown in FIG. 6B; FIG. 6D is a modified embodiment of the present invention, illustrating a leading or focus electrode added to the embodiment in FIG. 4D;

FIG. 7A is a perspective view of another embodiment of the present invention, illustrating a leading or focus electrode added to the embodiment shown in FIG. 4E; FIG. 7B is a perspective view of an embodiment modified from that shown in FIG. 7A; FIG. 7C is a perspective view of an embodiment modified from that shown in FIG. 7B;

FIG. 8A is a perspective view of still a further embodiment of the present invention, illustrating another embodiment of the leading or focus electrode; FIG. 8B is a perspective view of an embodiment modified from that shown in FIG. 5A; FIG. 8C is a perspective view of yet another embodiment;

FIGS. 9A-9C; FIG. 9A is perspective view of a further embodiment of the present invention; FIG. 9B is a partial view of an embodiment modified from that shown in FIG. 10A; FIG. 9C is another embodiment modified from that shown in FIG. 9A;

FIG. 10A is a perspective view of another embodiment of the present invention, illustrating a trailing electrode added to the embodiment in FIG. 7A; FIG. 10B is a plan view of the embodiment shown in FIG. 10A; FIG. 10C is a plan view of a further embodiment of the present invention; FIG. 10D is a plan view of another embodiment of the present invention similar to FIG. 10C.

FIG. 11A is a plan view of still another embodiment of the present invention; FIG. 11B is a plan view of an embodiment modified from that shown in FIG. 11A; FIG. 11C is a plan view of a further embodiment of the present invention; FIG. 11D is a plan view of an embodiment modified from that shown in FIG. 11C; FIG. 11E is a plan view of a further embodiment of the present invention; FIG. 11F is a plan view of an embodiment modified from that shown in FIG. 11F; FIG. 12A is a perspective view of still another embodiment of the present invention; FIG. 12B is a perspective view of a further embodiment of the present invention; FIG. 12C is a perspective view of yet another embodiment of the present invention;

DETAILED DESCRIPTION OF THE PREFERRED EMBODIMENTS

Overall Air Transporter-Conditioner System Configuration

Figure 1A:
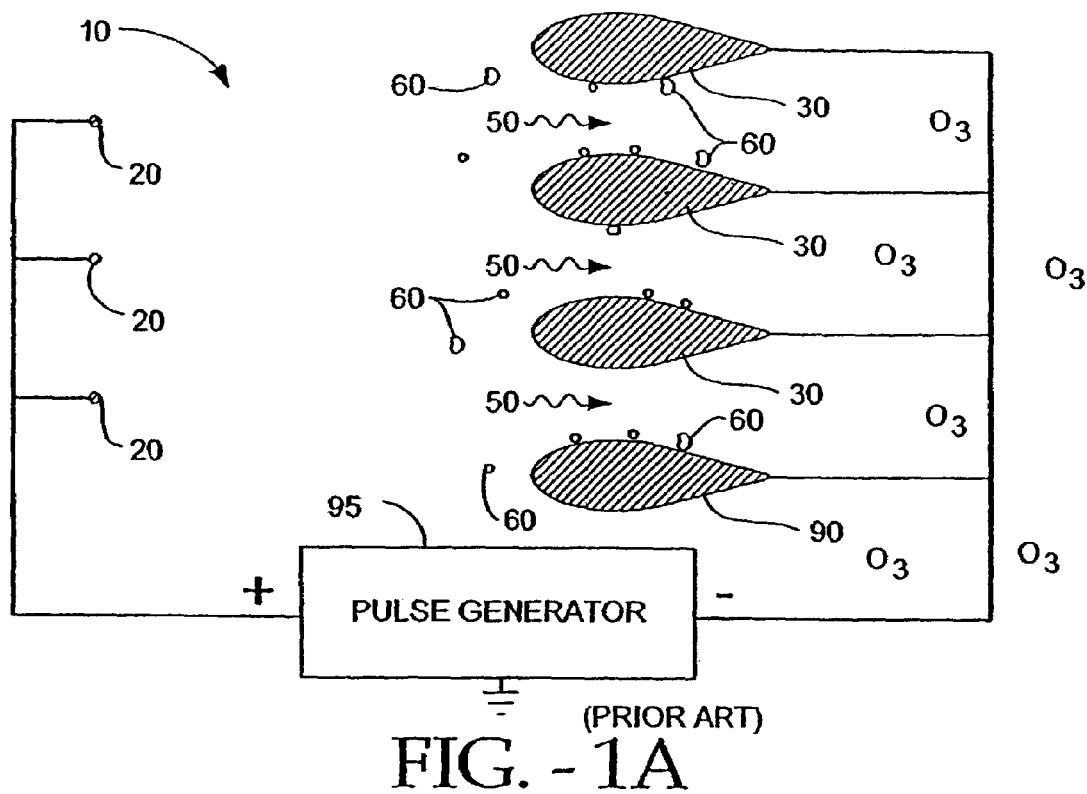
FIGS. 1A-1B.
Figure 1B:
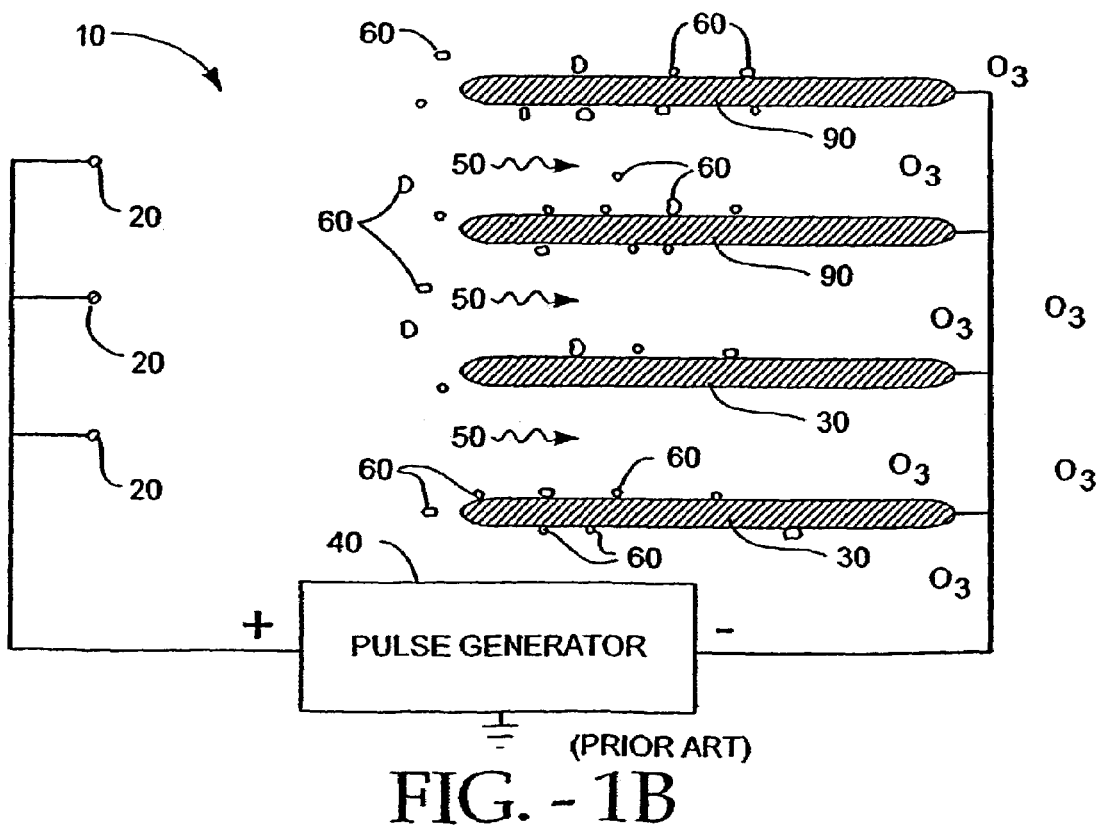
Figure 2A:
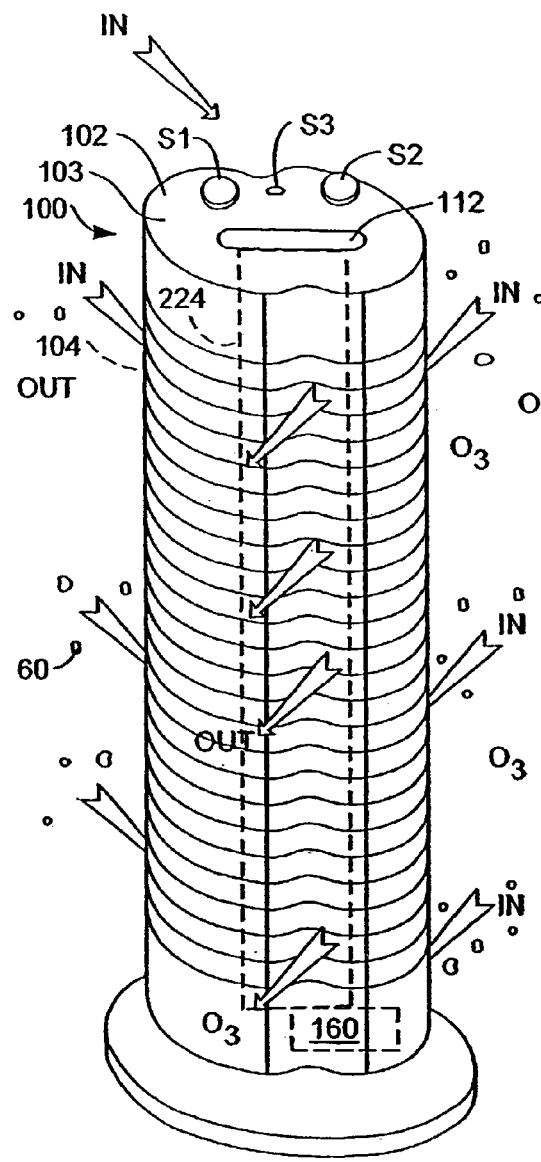
FIGS. 2A-2B.
Figure 2B:
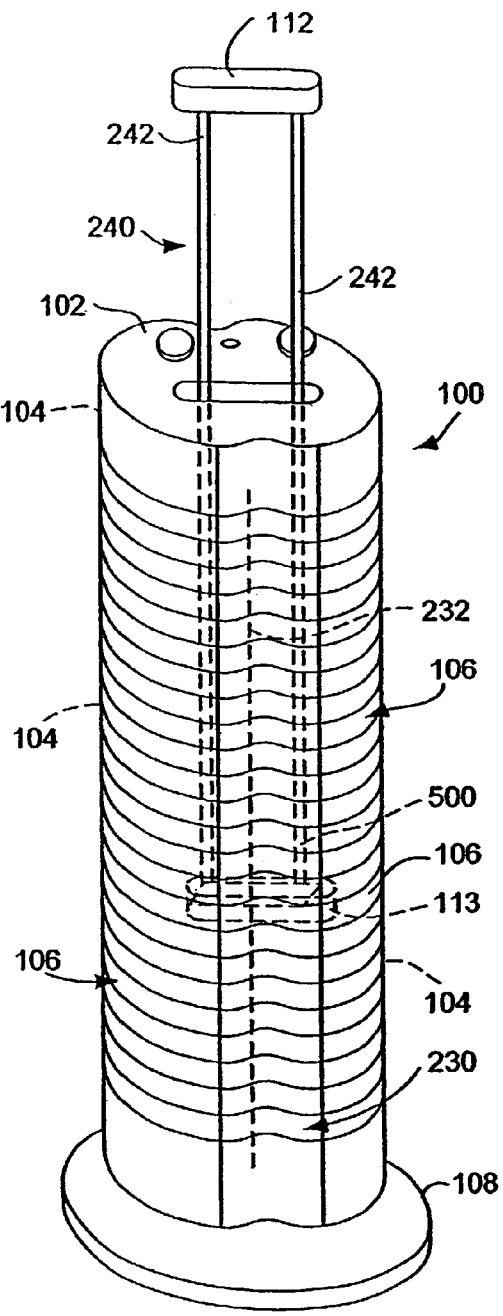

FIGS. 2A and 2B depict an electro-kinetic air transporter-conditioner system 100 whose housing 102 includes preferably rear-located intake vents or louvers 104 and preferably front located exhaust vents 106, and a base pedestal 108. If desired a single vent can provide and be used as both an air intake and an air exhaust with an air inlet channel and an air exhaust channel communicating with the vent and the electrodes. Preferably the housing is freestanding and/or upstandingly vertical and/or elongated. Internal to the transporter housing is an ion generating unit 160, preferably powered by an AC:DC power supply that is energizable or excitable using switch S1. S1, which along with the other below described user operated switches are conveniently located at the top 103 of the unit 100. Ion generating unit 160 is self-contained in that other ambient air, nothing is required from beyond the transporter housing, save external operating potential, for operation of the present invention.

The upper surface of housing 102 includes a user-liftable handle member 112 to which is affixed a second array 240 of collector electrodes 242 within an electrode assembly 220. Electrode assembly 220 also comprises a first array of emitter electrodes 230, or a single first electrode shown here as a single wire or wire-shaped electrode 232. (The terms "wire" and "wire-shaped" shall be used interchangeably herein to mean an electrode either made from a wire or, if thicker or stiffer than a wire, having the appearance of a wire.) In the embodiment shown, lifting member 112 lifts second array electrodes 240 upward, causing the second electrode to telescope out of the top of the housing and, if desired, out of unit 100 for cleaning, while the first electrode array 230 remains within unit 100. As is evident from the figure, the second array of electrode can be lifted vertically out from the top 103 of unit 100 along the longitudinal axis or direction of the elongated housing 102. This arrangement with the second electrodes removable from the top 103 of the unit 100, makes it easy for the user to pull the second electrodes out for cleaning. In FIG. 2B, the bottom ends of second electrodes 242 are connected to a member 113, to which is attached a mechanism 500, which includes a flexible member and a slot for capturing and cleaning the first electrode 232, whenever handle member 112 is moved upward or downward by a user.

Figure 3:
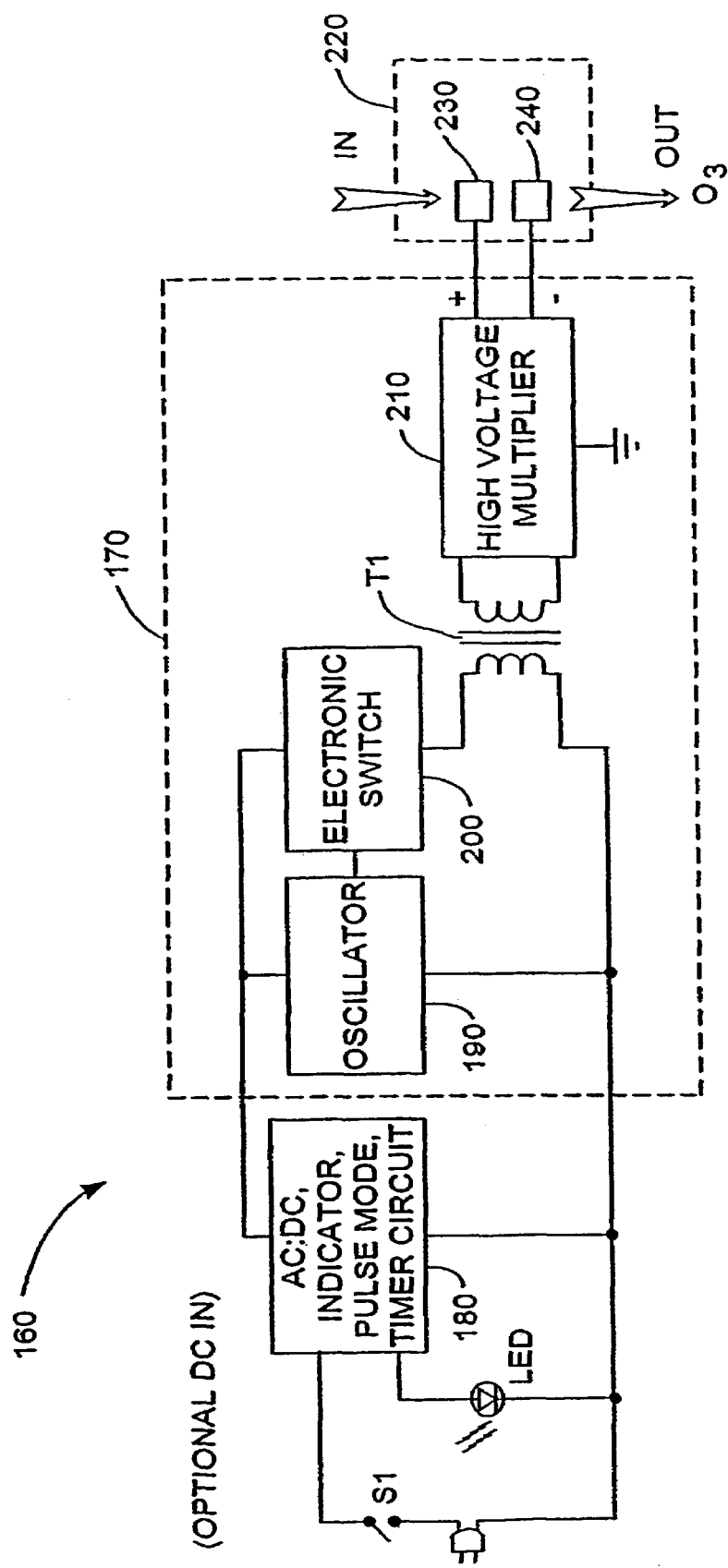
FIG. 3 is an electrical block diagram of the present invention.

The first and second arrays of electrodes are coupled to the output terminals of ion generating unit 160, as best seen in FIG. 3.

The general shape of the embodiment of the invention shown in FIGS. 2A and 2B is that of a figure eight in cross-section, although other shapes are within the spirit and scope of the invention. The top-to-bottom height of the preferred embodiment is in one preferred embodiment, 1 m, with a left-to-right width of preferably 15 cm, and a front-toback depth of perhaps 10 cm, although other dimensions and shapes can of course be used. A louvered construction provides ample inlet and outlet venting in an economical housing configuration. There need be no real distinction between vents 104 and 106, except their location relative to the second electrodes. These vents serve to ensure that an adequate flow of ambient air can be drawn into or made available to the unit 100, and that an adequate flow of ionized air that includes appropriate amounts of $O_3$ flows out from unit 100.

As will be described, when unit 100 is energized with S1, high voltage or high potential output by ion generator 160 produces ions at the first electrode, which ions are attracted to the second electrodes. The movement of the ions in an "IN" to "OUT" direction carries with the ions air molecules, thus electro-kinetically producing an outflow of ionized air. The "IN" notation in FIGS. 2A and 2B denote the intake of ambient air with particulate matter 60. The "OUT" notation in the figures denotes the outflow of cleaned air substantially devoid of the particulate matter, which particulate matter adheres electrostatically to the surface of the second electrodes. In the process of generating the ionized airflow appropriate amounts of ozone ($O_3$) are beneficially produced. It may be desired to provide the inner surface of housing 102 with an electrostatic shield to reduces detectable electromagnetic radiation. For example, a metal shield could be disposed within the housing, or portions of the interior of the housing can be coated with a metallic paint to reduce such radiation.

The housing preferably has a substantially oval-shaped or-elliptically shaped cross-section with dimpled side grooves. Thus, as indicated above, the cross-section looks somewhat like a figure eight. It is within the scope of the present invention for the housing to have a different shaped cross-section such as, but not limited to, a rectangular shape, an egg shape, a tear-drop shape, or circular shape. The housing preferably has a tall, thin configuration. As will become apparent later, the housing is preferably functionally shaped to contain the electrode assembly.

As mentioned above, the housing has an inlet and an outlet. Both the inlet and the outlet are covered by fins or louvers. Each fin is a thin ridge spaced-apart from the next fin, so that each fin creates minimal resistance as air flows through the housing. The fins are horizontal and are directed across the elongated vertical upstanding housing of the unit. Thus, the fins are substantially perpendicular in this preferred embodiment to the electrodes. The inlet and outlet fins are aligned to give the unit a "see through" appearance. Thus, a user can "see through" the unit from the inlet to the outlet. The user will see no moving parts within the housing, but just a quiet unit that cleans the air passing therethrough. Alternatively the fins can be parallel with the electrodes in another preferred embodiment. Other orientations of fins and electrodes are possible in other embodiments.

As best seen in FIG. 3, ion generating unit 160 includes a high voltage generator unit 170 and circuitry 180 for converting raw alternating voltage (e.g., 117 VAC) into direct current ("DC") voltage. Circuitry 180 preferably includes circuitry controlling the shape and/or duty cycle of the generator unit output voltage (which control is altered with user switch S2). Circuitry 180 preferably also includes a pulse mode component, coupled to switch S3, to temporarily provide a burst of increased output ozone. Circuitry 180 can also include a timer circuit and a visual indicator such as a light emitting diode ("LED"). The LED or other indicator (including, if desired, an audible indicator) signals when ion generation quits occurring. The timer can automatically halt generation of ions and/or ozone after some predetermined time, e.g., 30 minutes.

The high voltage generator unit 170 preferably comprises a low voltage oscillator circuit 190 of perhaps 20 KHz frequency, that outputs low voltage pulses to an electronic switch 200, e.g., a thyristor or the like. Switch 200 switchably couples the low voltage pulses to the input winding of a step-up transformer T1. The secondary winding of T1 is coupled to a high voltage multiplier circuit 210 that outputs high voltage pulses. Preferably the circuitry and components comprising high voltage pulse generator 170 and circuit 180 are fabricated on a printed circuit board that is mounted within housing 102. If desired, external audio input (e.g., from a stereo tuner) could be suitably coupled to oscillator 190 to acoustically modulate the kinetic airflow produced by unit 160. The result would be an electrostatic loudspeaker, whose output airflow is audible to the human ear in accordance with the audio input signal. Further, the output air stream would still include ions and ozone.

Output pulses from high voltage generator 170 preferably are at least 10 KV peak-to-peak with an effective DC offset of, for example, half the peak-to-peak voltage, and have a frequency of, for example, 20 KHz. Frequency of oscillation can include other values, but frequency of at least about 20 KHz is preferred as being inaudible to humans. If pets will be in the same room as the unit 100, it may be desired to utilize and even higher operating frequency, to prevent pet discomfort and/or howling by the pet. The pulse train output preferably has a duty cycle of for example 10%, which will promote battery lifetime if live current is not used. Of course, different peak-peak amplitudes, DC offsets, pulse train wave shapes, duty cycle, and/or repetition frequencies can be used instead. Indeed, a 100% pulse train (e.g., an essentially DC high voltage) may be used, albeit with shorter battery lifetime. Thus, generator unit 170 for this embodiment can be referred to as a high voltage pulse generator. Unit 170 functions as a DC:DC high voltage generator, and could be implemented using other circuitry and/or techniques to output high voltage pulses that are input to electrode assembly 220.

As noted, outflow (OUT) preferably includes appropriate amounts of ozone that can remove odors and preferably destroy or at least substantially alter bacteria, germs, and other living (or quasi-living) matter subjected to the outflow. Thus, when switch S1 is closed and the generator 170 has sufficient operating potential, pulses from high voltage pulse generator unit 170 create an outflow (OUT) of ionized air and ozone. When S1 is closed, LED will visually signal when ionization is occurring.

Preferably operating parameters of unit 100 are set during manufacture and are generally not user-adjustable. For example, with respect to operating parameters, increasing the peak-to-peak output voltage and/or duty cycle in the high voltage pulses generated by unit 170 can increase the airflow rate, ion content, and ozone content. These parameters can be set by the user by adjusting switch S2 as disclosed below.

In the preferred embodiment, output flow rate is about 200 feet/minute, ion content is about 2,000,000/cc and ozone content is about 40 ppb (over ambient) to perhaps 2,000 ppb (over ambient). Decreasing the ratio of the radius of the nose of the second electrodes to the radius of the first electrode or decreasing the ratio of the cross-sectioned area of the second electrode to the first electrode below about 20:1 will decrease flow rate, as will decreasing the peak-to-peak voltage and/or duty cycle of the high voltage pulses coupled between the first and second electrode arrays.

In practice, unit 100 is placed in a room and connected to an appropriate source of operating potential, typically 117 VAC. With S1 energizing ionization unit 160, systems 100 emits ionized air and preferably some ozone via outlet vents 106. The airflow, coupled with the ions and ozone freshens the air in the room, and the ozone can beneficially destroy or at least diminish the undesired effects of certain odors, bacteria, germs, and the like. The airflow is indeed electrokinetically produced, in that there are no intentionally moving parts within unit 100. (Some mechanical vibration may occur within the electrodes.).

Having described various aspects of this embodiment of the invention in general, preferred embodiments of electrode assembly 220 are now described. In the various embodiments, electrode assembly 220 comprises a first array 230 of at least one electrode or conductive surface 232, and further comprises a second array 240 of preferably at least one electrode or conductive surface 242. Understandably material(s) for electrodes 232 and 242 should conduct electricity, be resistant to corrosive effects from the application of high voltage, yet be strong enough to be cleaned.

In the various electrode assemblies to be described herein, electrode(s) 232 in the first electrode array 230 are preferably fabricated from tungsten. Tungsten is sufficiently robust in order to withstand cleaning, has a high melting point to retard breakdown due to ionization, and has a rough exterior surface that seems to promote efficient ionization. On the other hand, electrode(s) 242 preferably have a highly polished exterior surface to minimize unwanted point-to-point radiation. As such, electrode(s) 242 preferably are fabricated from stainless steel and/or brass, among other materials. The polished surface of electrode(s) 232 also promotes ease of electrode cleaning.

In contrast to the prior art electrodes disclosed by the '801 patent, electrodes 232 and 242, are light weight, easy to fabricate, and lend themselves to mass production. Further, electrodes 232 and 242 described herein promote more efficient generation of ionized air, and appropriate amounts of ozone, (indicated in several of the figures as $O_3$).

Electrode Assembly with First and Second Electrodes

FIGS. 4A-4F

FIGS. 4A-4F illustrate various configurations of the electrode assembly 220. The output from high voltage pulse generator unit 170 is coupled to an electrode assembly 220 that comprises a first electrode array 230 and a second electrode array 240. Again, instead of arrays, single electrodes or single conductive surfaces can be substituted for one or both array 230 and array 240.

The positive output terminal of unit 170 is coupled to first electrode array 230, and the negative output terminal is coupled to second electrode array 240. It is believed that with this arrangement the net polarity of the emitted ions is positive, e.g., more positive ions than negative ions are emitted. This coupling polarity has been found to work well, including minimizing unwanted audible electrode vibration or hum. However, while generation of positive ions is conducive to a relatively silent airflow, from a health standpoint, it is desired that the output airflow be richer in negative ions, not positive ions. It is noted that in some embodiments, one port (preferably the negative port) of the high voltage pulse generator can in fact be the ambient air. Thus, electrodes in the second array need not be connected to the high voltage pulse generator using a wire. Nonetheless, there will be an "effective connection" between the second array electrodes and one output port of the high voltage pulse generator, in this instance, via ambient air. Alternatively the negative output terminal of unit 170 can be connected to the first electrode array 230 and the positive output terminal can be connected to the second electrode array 240.

With this arrangement an electrostatic flow of air is created, going from the first electrode array towards the second electrode array. (This flow is denoted "OUT" in the figures.) Accordingly electrode assembly 220 is mounted within transporter system 100 such that second electrode array 240 is closer to the OUT vents and first electrode array 230 is closer to the IN vents.

When voltage or pulses from high voltage pulse generator 170 are coupled across first and second electrode arrays 230 and 240, a plasma-like field is created surrounding electrodes 232 in first array 230. This electric field ionizes the ambient air between the first and second electrode arrays and establishes an "OUT" airflow that moves towards the second array. It is understood that the IN flow enters via vent(s) 104, and that the OUT flow exits via vent(s) 106.

Ozone and ions are generated simultaneously by the first array electrodes 232, essentially as a function of the potential from generator 170 coupled to the first array of electrodes or conductive surfaces. Ozone generation can be increased or decreased by increasing or decreasing the potential at the first array. Coupling an opposite polarity potential to the second array electrodes 242 essentially accelerates the motion of ions generated at the first array, producing the airflow denoted as "OUT" in the figures. As the ions and ionized particulate move toward the second array, the ions and ionized particles push or move air molecules toward the second array. The relative velocity of this motion may be increased, by way of example, by decreasing the potential at the second array relative to the potential at the first array.

For example, if +10 KV were applied to the first array electrode(s), and no potential were applied to the second array electrode(s), a cloud of ions (whose net charge is positive) would form adjacent the first electrode array. Further, the relatively high 10 KV potential would generate substantial ozone. By coupling a relatively negative potential to the second array electrode(s), the velocity of the air mass moved by the net emitted ions increases.

On the other hand, if it were desired to maintain the same effective outflow (OUT) velocity, but to generate less ozone, the exemplary 10 KV potential could be divided between the electrode arrays. For example, generator 170 could provide +4 KV (or some other fraction) to the first array electrodes and −6 KV (or some other fraction) to the second array electrodes. In this example, it is understood that the +4 KV and the −6 KV are measured relative to ground. Understandably it is desired that the unit 100 operates to output appropriate amounts of ozone. Accordingly, the high voltage is preferably fractionalized with about +4 KV applied to the first array electrodes and about −6 KV applied to the second array electrodes.

Figure 4A:
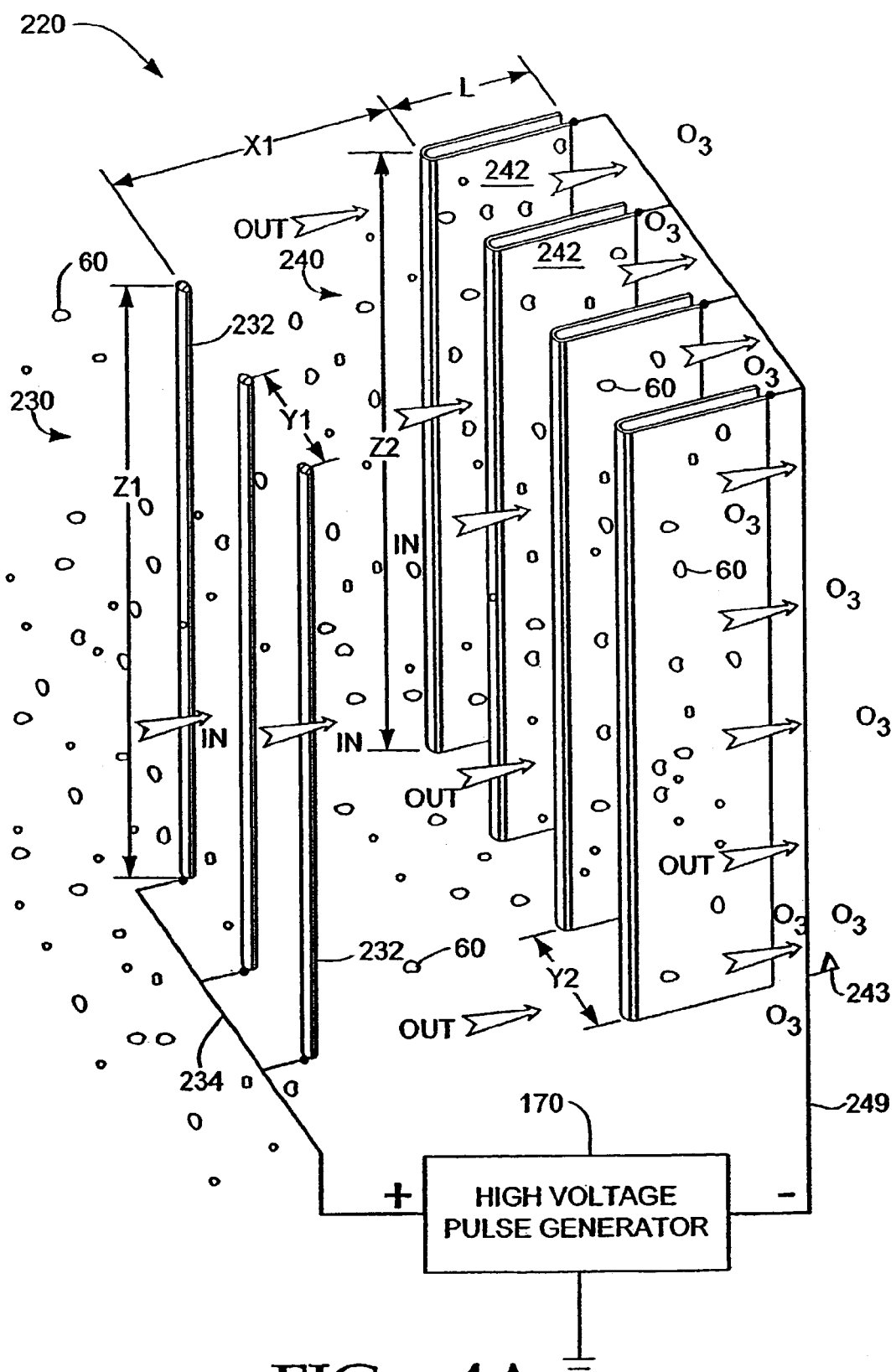
FIGS. 4A-4F.
Figure 4B:
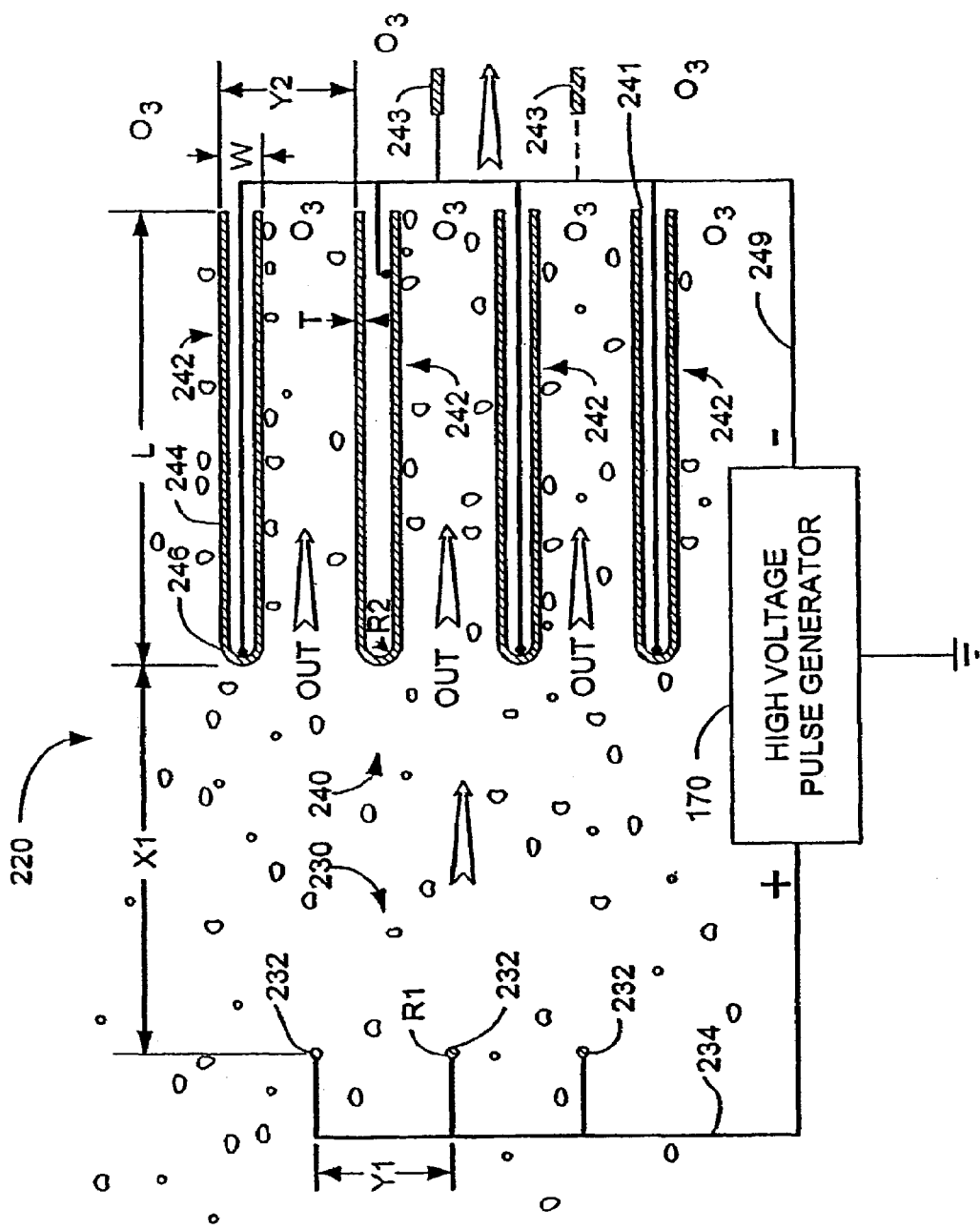

In the embodiments of FIGS. 4A and 4B, electrode assembly 220 comprises a first array 230 of wire-shaped electrodes 232, and a second array 240 of generally "U"-shaped electrodes 242. In preferred embodiments, the number N1 of electrodes comprising the first array can preferably differ by one relative to the number N2 of electrodes comprising the second array 240. In many of the embodiments shown, N2>N1. However, if desired, additional first electrodes 232 could be added at the outer ends of array 230 such that N1>N2, e.g., five first electrodes 232 compared to four second electrodes 242.

As previously indicated first or emitter electrodes 232 are preferably lengths of tungsten wire, whereas electrodes 242 are formed from sheet metal, preferably stainless steel, although brass or other sheet metal could be used. The sheet metal is readily configured to define side regions 244 and bulbous nose region 246, forming the hollow, elongated "U"-shaped electrodes 242. While FIG. 4A depicts four electrodes 242 in second array 240 and three electrodes 232 in first array 230, as noted previously, other numbers of electrodes in each array could be used, preferably retaining a symmetrically staggered configuration as shown. It is seen in FIG. 4A that while particulate matter 60 is present in the incoming (IN) air, the outflow (OUT) air is substantially devoid of particulate matter, which adheres to the preferably large surface area provided by the side regions 244 of the second array electrodes 242.

FIG. 4B illustrates that the spaced-apart configuration between the first and second arrays 230, 240 is staggered. Preferably, each first array electrode 232 is substantially equidistant from two second array electrodes 242. This symmetrical staggering has been found to be an efficient electrode placement. Preferably, in this embodiment, the staggering geometry is symmetrical in that adjacent electrodes 232 or adjacent electrodes 242 are spaced-apart a constant distance, Y1 and Y2 respectively. However, a non-symmetrical configuration could also be used. Also, it is understood that the number of electrodes 232 and 242 may differ from what is shown.

In the embodiment of FIGS. 4A, typically dimensions are as follows: diameter of electrodes 232, R1, is about 0.08 mm, distances Y1 and Y2 are each about 16 mm, distance X1 is about 16 mm, distance L is about 20 mm, and electrode heights Z1 and Z2 are each about 1 m. The width W of electrodes 242 is preferably about 4 mm, and the thickness of the material from which electrodes 242 are formed is about 0.5 mm. Of course other dimensions and shapes could be used. For example, preferred dimensions for distance X1 may vary between 12-30 mm, and the distance Y2 may vary between 1530 mm. It is preferred that electrodes 232 have a small diameter. A wire having a small diameter, such as R1, generates a high voltage field and has a high emissivity. Both characteristics are beneficial for generating ions. At the same time, it is desired that electrodes 232 (as well as electrodes 242) be sufficiently robust to withstand occasional cleaning.

Electrodes 232 in first array 230 are coupled by a conductor 234 to a first (preferably positive) output port of high voltage pulse generator 170. Electrodes 242 in second array 240 are coupled by a conductor 249 to a second (preferably negative) output port of high voltage generator 170. The electrodes may be electrically connected to the conductors 234 or 249 at various locations. By way of example only, FIG. 4B depicts conductor 249 making connection with some electrodes 242 internal to bulbous end 246, while other electrodes 242 make electrical connection to conductor 249 elsewhere on the electrode 242. Electrical connection to the various electrodes 242 could also be made on the electrode external surface, provided no substantial impairment of the outflow airstream results; however it has been found to be preferable that the connection is made internally.

In this and the other embodiments to be described herein, ionization appears to occur at the electrodes 232 in the first electrode array 230, with ozone production occurring as a function of high voltage arcing. For example, increasing the peak-to-peak voltage amplitude and/or duty cycle of the pulses from the high voltage pulse generator 170 can increase ozone content in the output flow of ionized air. If desired, user-control S2 can be used to somewhat vary ozone content by varying amplitude and/or duty cycle. Specific circuitry for achieving such control is known in the art and need not be described in detail herein.

Note the inclusion in FIGS. 4A and 4B of at least one output controlling electrodes 243, preferably electrically coupled to the same potential as the second array electrodes 242. Electrode 243 preferably defines a pointed shape in side profile, e.g., a triangle. The sharp point on electrodes 243 causes generation of substantial negative ions (since the electrode is coupled to relatively negative high potential). These negative ions neutralize excess positive ions otherwise present in the output airflow, such that the OUT flow has a net negative charge. Electrodes 243 is preferably stainless steel, copper, or other conductor material, and is perhaps 20 mm high and about 12 mm wide at the base. The inclusion of one electrode 243 has been found sufficient to provide a sufficient number of output negative ions, but more such electrodes may be included.

Figure 4C:
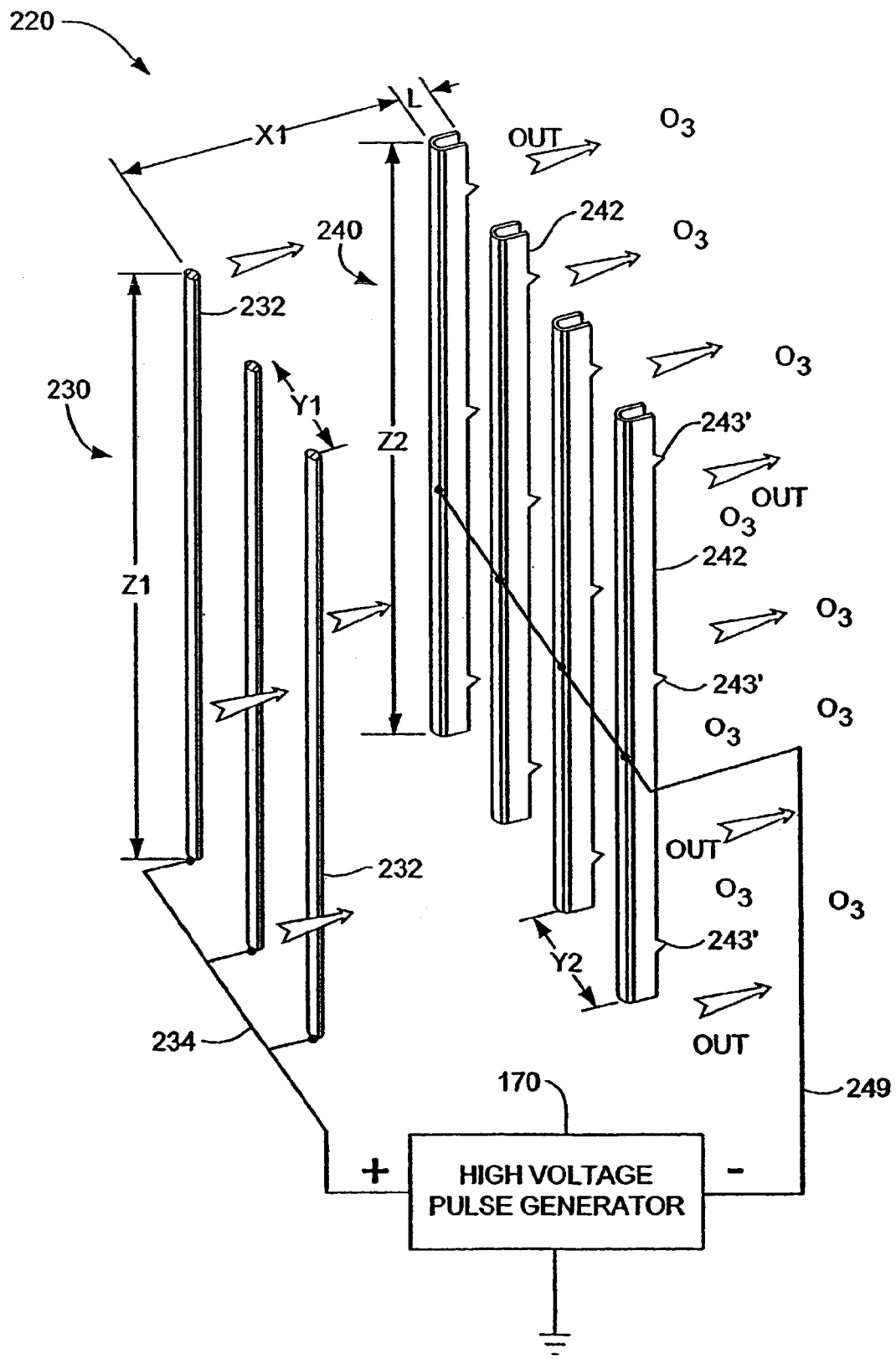

In the embodiments of FIGS. 4A, 4B and 4C, each "U"-shaped electrode 242 has two trailing surface or sides 244 that promote efficient kinetic transport of the outflow of ionized air and ozone. For the embodiment of FIG. 4C, there is the inclusion on at least one portion of a trailing edge of a pointed electrode region 243'. Electrode region 243' helps promote output of negative ions, in the same fashion that was previously described with respect to electrodes 243, as shown in FIGS. 4A and 4B.

In FIG. 4C and the figures to follow, the particulate matter is omitted for ease of illustration. However, from what was shown in FIGS. 4A-4B, particulate matter will be present in the incoming air, and will be substantially absent from the outgoing air. As has been described, particulate matter 60 typically will be electrostatically precipitated upon the surface area of electrodes 242.

As discussed above and as depicted by FIG. 4C, it is relatively unimportant where on an electrode array electrical connection is made. Thus, first array electrodes 232 are shown electrically connected together at their bottom regions by conductor 234, whereas second array electrodes 242 are shown electrically connected together in their middle regions by the conductor 249. Both arrays may be connected together in more than one region, e.g., at the top and at the bottom. It is preferred that the wire or strips or other inter-connecting mechanisms be at the top, bottom, or periphery of the second array electrodes 242, so as to minimize obstructing stream air movement through the housing 210.

Figure 4D:
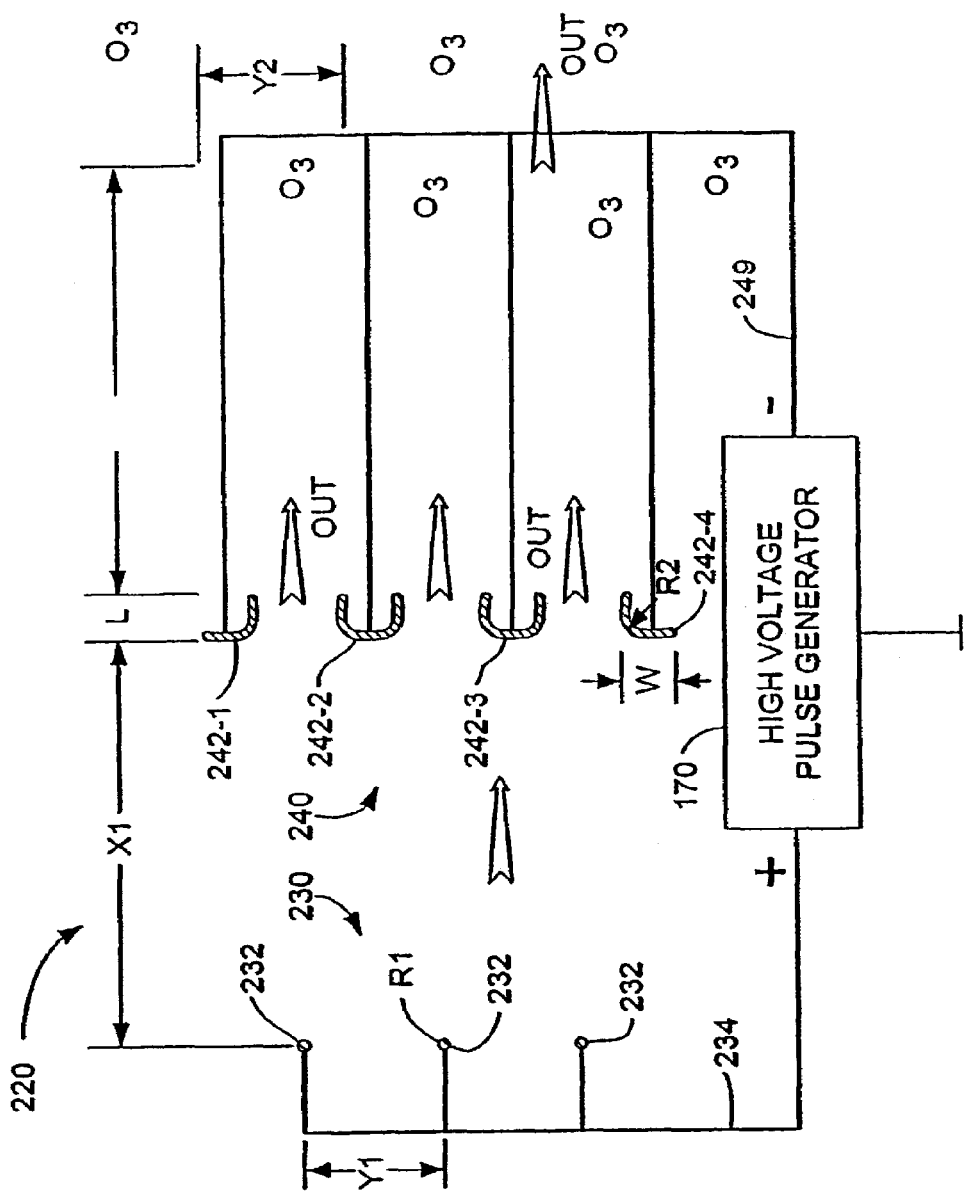

It is noted that the embodiments of FIGS. 4C and 4D depict somewhat truncated versions of the second electrodes 242. Whereas dimension L in the embodiment of FIGS. 4A and 4B was about 20 mm, in FIGS. 4C and 4D, L has been shortened to about 8 mm. Other dimensions in FIG. 4C preferably are similar to those stated for FIGS. 4A and 4B. It will be appreciated that the configuration of second electrode array 240 in FIG. 4C can be more robust than the configuration of FIGS. 4A and 4B, by virtue of the shorter trailing edge geometry. As noted earlier, a symmetrical staggered geometry for the first and second electrode arrays is preferred for the configuration of FIG. 4C.

In the embodiment of FIG. 4D, the outermost second electrodes, denoted 242-1 and 242-4, have substantially no outermost trailing edges. Dimension L in FIG. 4D is preferably about 3 mm, and other dimensions may be as stated for the configuration of FIGS. 4A and 4B. Again, the ratio of the radius or surface areas between the first electrode 232 and the second electrodes 242 for the embodiment of FIG. 4D preferably exceeds about 20:1.

Figure 4E:
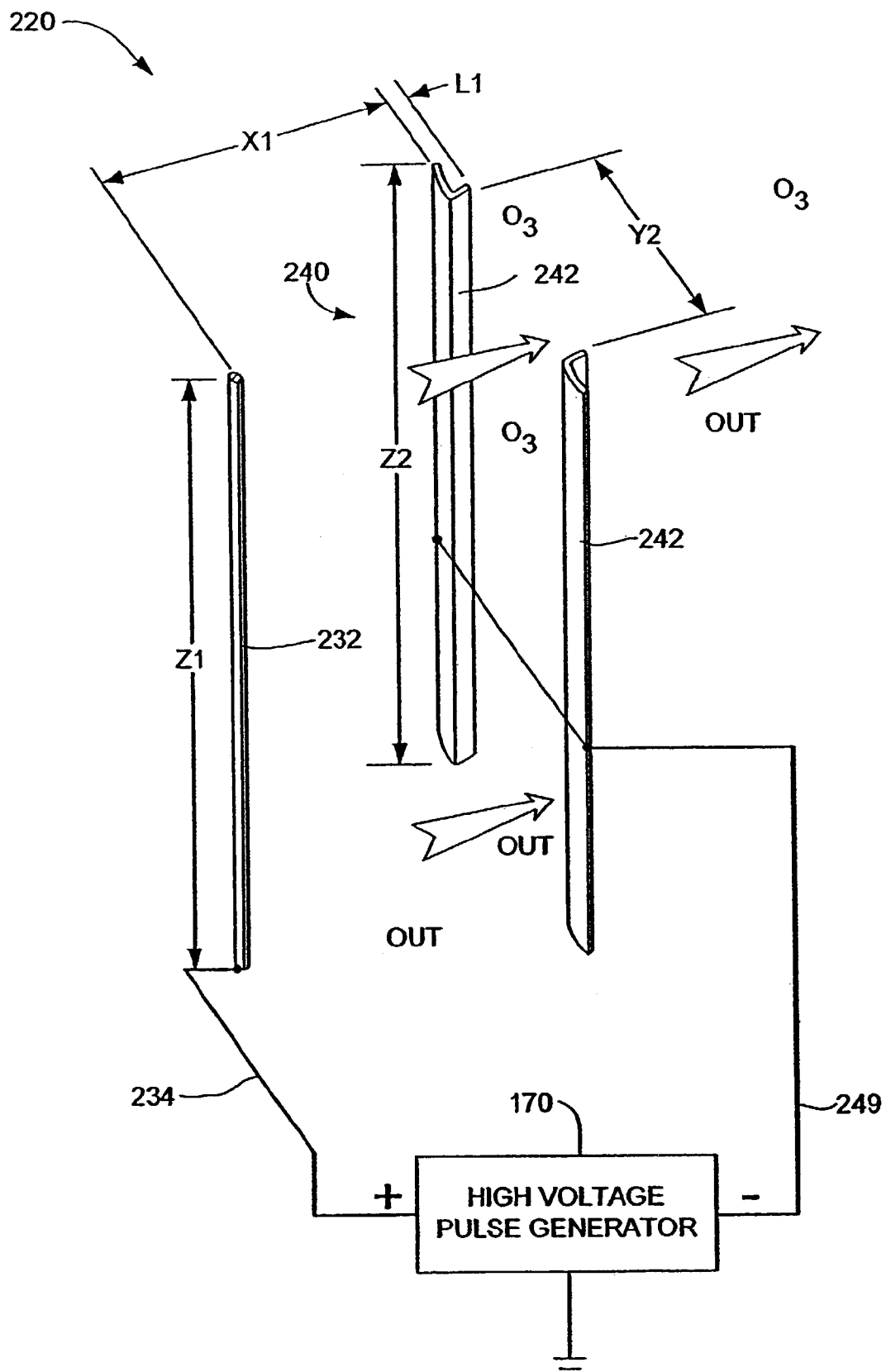
Figure 4F:
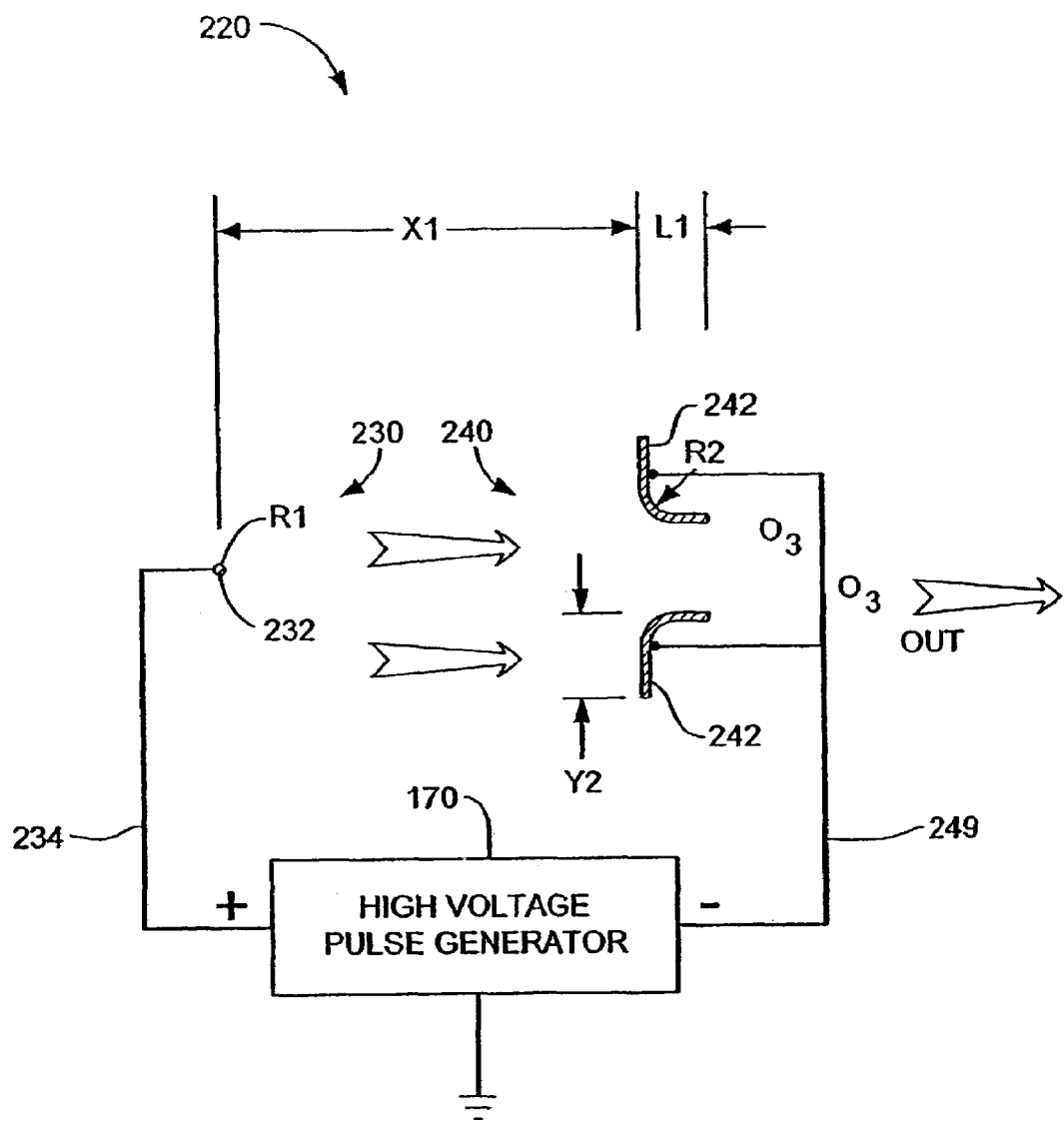

FIGS. 4E and 4F depict another embodiment of electrode assembly 220, in which the first electrode array 230 comprises a single wire electrode 232, and the second electrode array 240 comprises a single pair of curved "L"-shaped electrodes 242, in cross-section. Typical dimensions, where different than what has been stated for earlier-described embodiments, are $X1 \approx 12$ mm, $Y2 \approx 5$ mm, and $L1 \approx 3$ mm. The effective surface area or radius ratio is again greater than about 20:1. The fewer electrodes comprising assembly 220 in FIGS. 4E and 4F promote economy of construction, and ease of cleaning, although more than one electrode 232, and more than two electrodes 242 could of course be employed. This particular embodiment incorporates the staggered symmetry described earlier, in which electrode 232 is equidistant from two electrodes 242. Other geometric arrangements, which may not be equidistant, are within the spirit and scope of the invention.

Electrode Assembly With an Upstream Focus Electrode

FIGS. 5A-5B

Figure 5A:
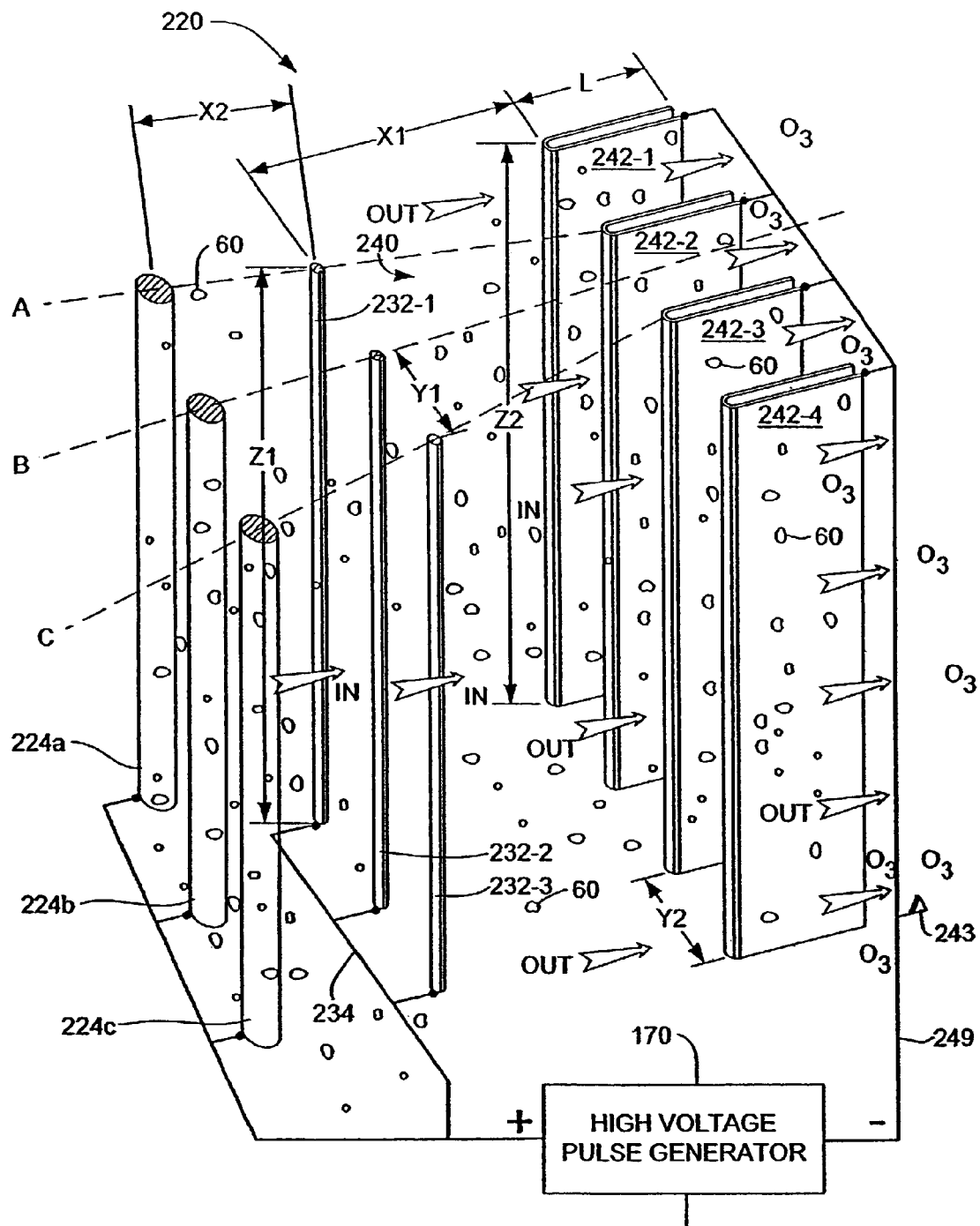
FIGS. 5A-5B.
Figure 5B:
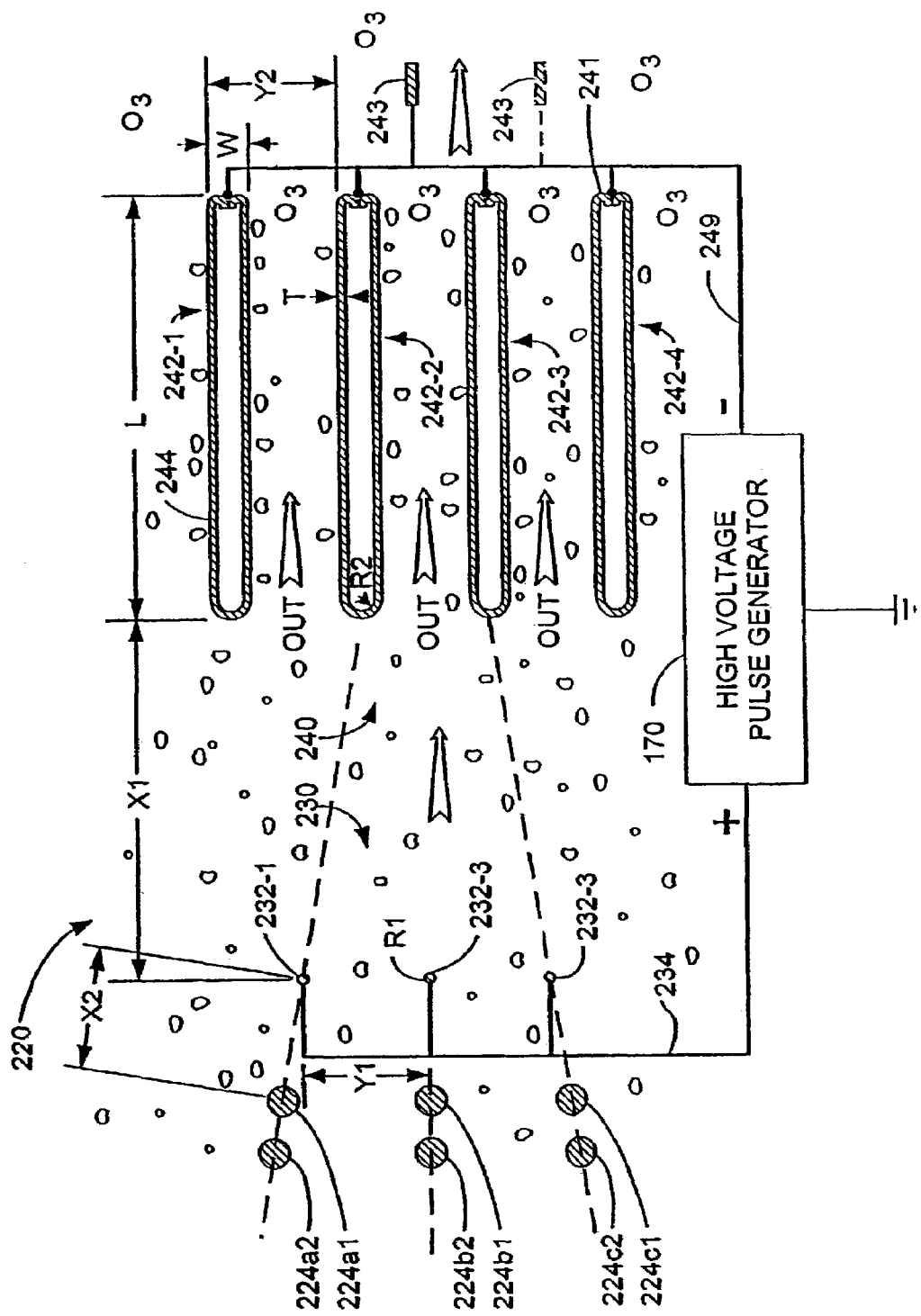

The embodiments illustrated in FIGS. 5A-5B are somewhat similar to the previously described embodiments in FIGS. 4A-4B. The electrode assembly 220 includes a first array of electrodes 230 and a second array of electrodes 240. Again, for this and the other embodiments, the term "array of electrodes" may refer to a single electrode or a plurality of electrodes. Preferably, the number of electrodes 232 in the first array of electrodes 230 will differ by one relative to the number of electrodes 242 in the second array of electrodes 240. The distances L, X1, Y1, Y2, Z1 and Z2 for this embodiment are similar to those previously described in FIG. 4A.

As shown in FIG. 5A, the electrode assembly 220 preferably adds a third, or leading, or focus, or directional electrode 224a, 224b, 224c (generally referred to as "electrode 224") upstream of each first electrode 232-1, 232-2, 232-3. The focus electrode 224 produces an enhanced airflow velocity exiting the devices 100 or 200. In general, the third focus electrode 224 directs the airflow, and ions generated by the first electrode 232, towards the second electrodes 242. Each third focus electrode 224 is a distance X2 upstream from at least one of the first electrodes 232. The distance X2 is preferably 5-6 mm, or four to five diameters of the focus electrode 224. However, the third focus electrode 224 can be further from or closer to the first electrode 232.

The third focus electrode 224 illustrated in FIG. 5A is a rod-shaped electrode. The third focus electrode 224 can also comprise other shapes that preferably do not contain any sharp edges. The third focus electrode 224 is preferably manufactured from material that will not erode or oxidize, such as stainless steel. The diameter of the third focus electrode 224, in a preferred embodiment, is at least fifteen times greater than the diameter of the first electrode 232. The diameter of the third focus electrode 224 can be larger or smaller. The diameter of the third focus electrode 224 is preferably large enough so that third focus electrode 224 does not function as an ion emitting surface when electrically connected with the first electrode 232. The maximum diameter of the third focus electrode 224 is somewhat constrained. As the diameter increases, the third focus electrode 224 will begin to noticeably impair the airflow rate of the units 100 or 200. Therefore, the diameter of the third electrode 224 is balanced between the need to form a non-ion emitting surface and airflow properties of the unit 100 or 200.

In a preferred embodiment, each third focus electrodes 224a, 224b, 224c are electrically connected with the first array 230 and the high voltage generator 170 by the conductor 234. As shown in FIG. 5A, the third focus electrodes 224 are electrically connected to the same positive outlet of the high voltage generator 170 as the first array 230. Accordingly, the first electrode 232 and the third focus electrode 224 generate a positive electrical field. Since the electrical fields generated by the third focus electrode 224 and the first electrode 232 are both positive, the positive field generated by the third focus electrode 224 can push, or repel, or direct, the positive field generated by the first electrode 232 towards the second array 240. For example, the positive field generated by the third focus electrode 224a will push, or repel, or direct, the positive field generated by the first electrode 232-1 towards the second array 240. In general, the third focus electrode 224 shapes the electrical field generated by each electrode 232 in the first array 230. This shaping effect is believe to decrease the amount of ozone generated by the electrode assembly 220 and increases the airflow of the units 100 and 200.

The particles within the airflow are positively charged by the ions generated by the first electrode 232. As previously mentioned, the positively charged particles are collected by the negatively charged second electrodes 242. The third focus electrode 224 also directs the airflow towards the second electrodes 242 by guiding the charged particles towards the trailing sides 244 of each second electrode 242. It is believed that the airflow will travel around the third focus electrode 224, partially focusing the airflow towards the trailing sides 244, improving the collection rate of the electrode assembly 220.

The third focus electrode 224 may be located at various positions upstream of each first electrode 232. By way of example only, a third focus electrode 224b is located directly upstream of the first electrode 232-2 so that the center of the third focus electrode 224b is in-line and symmetrically aligned with the first electrode 232-2, as shown by extension line B. Extension line B is located midway between the second electrode 242-2 and the second electrode 242-3.

Alternatively, a third focus electrode 224 can also be located at an angle relative to the first electrode 232. For example, a third focus electrode 224a can be located upstream of the first electrode 232-1 along a line extending from the middle of the nose 246 of the second electrode 242-2 through the center of the first electrode 232-1, as shown by extension line A. The third focus electrode 224a is in-line and symmetrically aligned with the first electrode 232-1 along extension line A. Similarly, the third electrode 224c is located upstream to the first electrode 232-3 along a line extending from the middle of the nose 246 of the second electrode 242-3 through the first electrode 232-3, as shown by extension line C. The third focus electrode 224c is in-line and symmetrically aligned with the first electrode 232-3 along extension line C. It is within the scope of the present invention for the electrode assembly 220 to include third focus electrodes 224 that are both directly upstream and at an angle to the first electrodes 232, as depicted in FIG. 5A. Thus the focus electrodes fan out relating to the first electrodes.

FIG. 5B illustrates that an electrode assembly 220 may contain multiple third focus electrodes 224 upstream of each first electrode 232. By way of example only, the third focus electrode 224a2 is in-line and symmetrically aligned with the third focus electrode 224a1, as shown by extension line A. In a preferred embodiment, only the third focus electrodes 224a1, 224b1, 224c1 are electrically connected to the high voltage generator 170 by conductor 234. Accordingly, not all of the third electrodes 224 are at the same operating potential. In the embodiment shown in FIG. 5B, the third focus electrodes 224a1, 224b1, 224c1 are at the same electrical potential as the first electrodes 232, while the third focus electrodes 224a2, 224b2, 224c2 are floating. Alternatively, the third focus electrodes 224a2, 224b2 and 224c2 may be electrically connected to the high voltage generator 170 by the conductor 234.

FIG. 5B illustrates that each second electrode 242 may also have a protective end 241. In the previous embodiments, each "U"-shaped second electrode 242 has an open end. Typically, the end of each trailing side or side wall 244 contains sharp edges. The gap between the trailing sides or side walls 244, and the sharp edges at the end of the trailing sides or side walls 244, generate unwanted eddy currents. The eddy currents create a "back draft," or airflow traveling from the outlet towards the inlet, which slow down the airflow rate of the units 100 or 200.

In a preferred embodiment, the protective end 241 is created by shaping, or rolling; the trailing sides or side walls 244 inward and pressing them together, forming a rounded trailing end with no gap between the trailing sides or side walls of each second electrode 242. Accordingly the side walls have outer surfaces, and the outer surface of end of the side walls are bent back adjacent to the trailing ends of the side walls so that the outer surface of the side walls are adjacent to, or face, or touch each other. Accordingly a smooth trailing edge is integrally formed on the second electrode. If desired, it is within the scope of the invention to spot weld the rounded ends together along the length of the second electrode 242. It is also within the scope of the present invention to form the protective end 241 by other methods such as, but not limited to, placing a strap of plastic across each end of the trailing sides 244 for the full length of the second electrode 242. The rounded or capped end is an improvement over the previous electrodes 242 without a protective end 241. Eliminating the gap between the trailing sides 244 also reduces or eliminates the eddy currents typically generated by the second electrode 242. The rounded protective end also provides a smooth surface for purpose of cleaning the second electrode. Accordingly in this embodiment the collector electrode is a one-piece, integrally formed, electrode with a protection end.

FIGS. 6A-6D

Figure 6A:
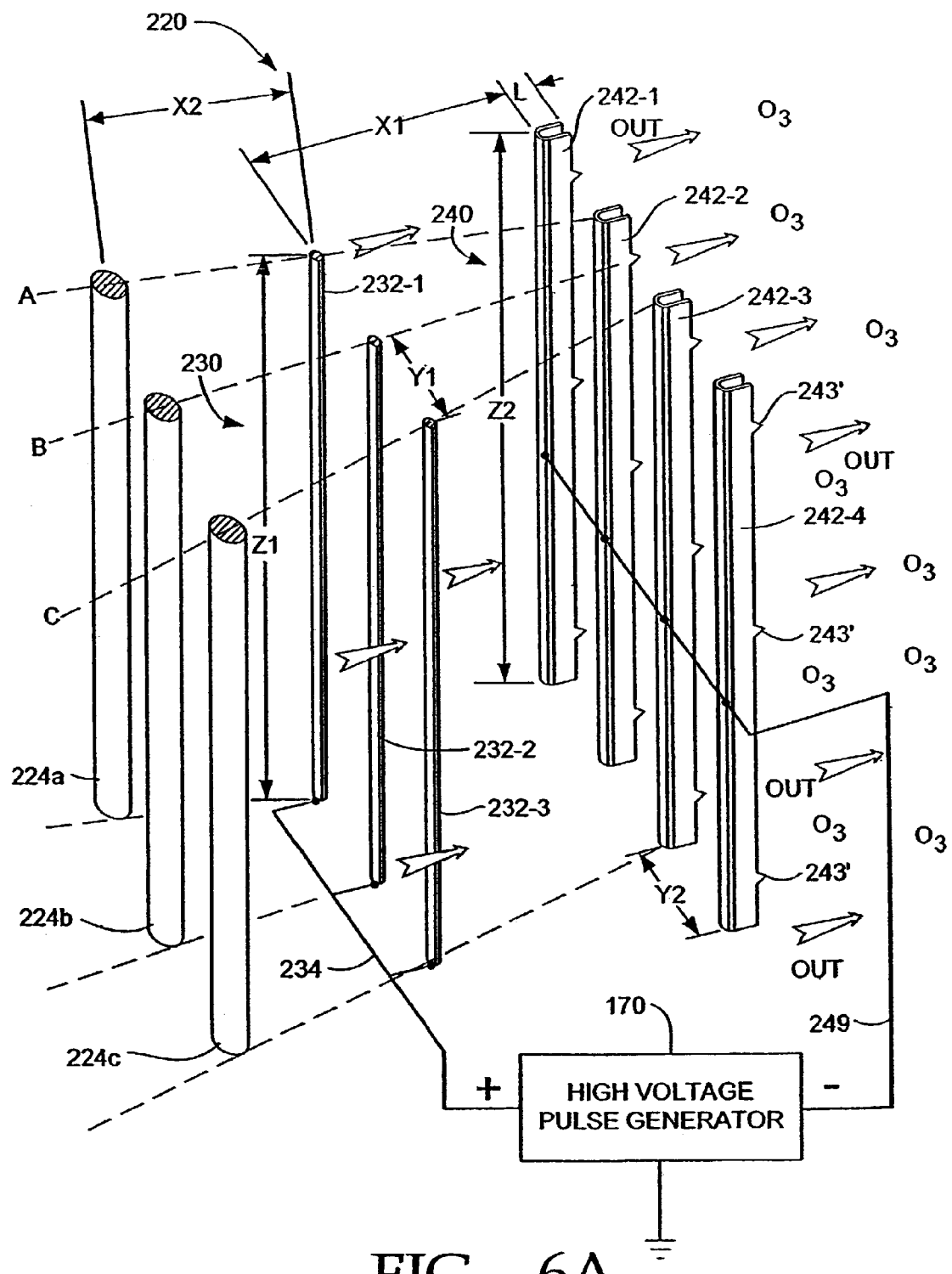
FIGS. 6A-6D.

FIG. 6A illustrates an electrode assembly 220 including a first array of electrodes 230 having three wire-shaped first electrodes 232-1, 232-2, 232-3 (generally referred to as "electrode 232") and a second array of electrodes 240 having four "U"-shaped second electrodes 242-1, 242-2, 242-3, 242-4 (generally referred to as "electrode 242"). Each first electrode 232 is electrically connected to the high voltage generator 170 at the bottom region, whereas each second electrode 242 is electrically connected to the high-voltage generator 170 in the middle to illustrate that the first and second electrodes 232, 242 can be electrically connected in a variety of locations.

The second electrode 242 in FIG. 6A is a similar version of the second electrode 242 shown in FIG. 4C. The distance L has been shortened to about 8 mm, while the other dimensions X1, Y1, Y2, Z1, Z2 are similar to those shown in FIG. 4A.

Figure 6B:
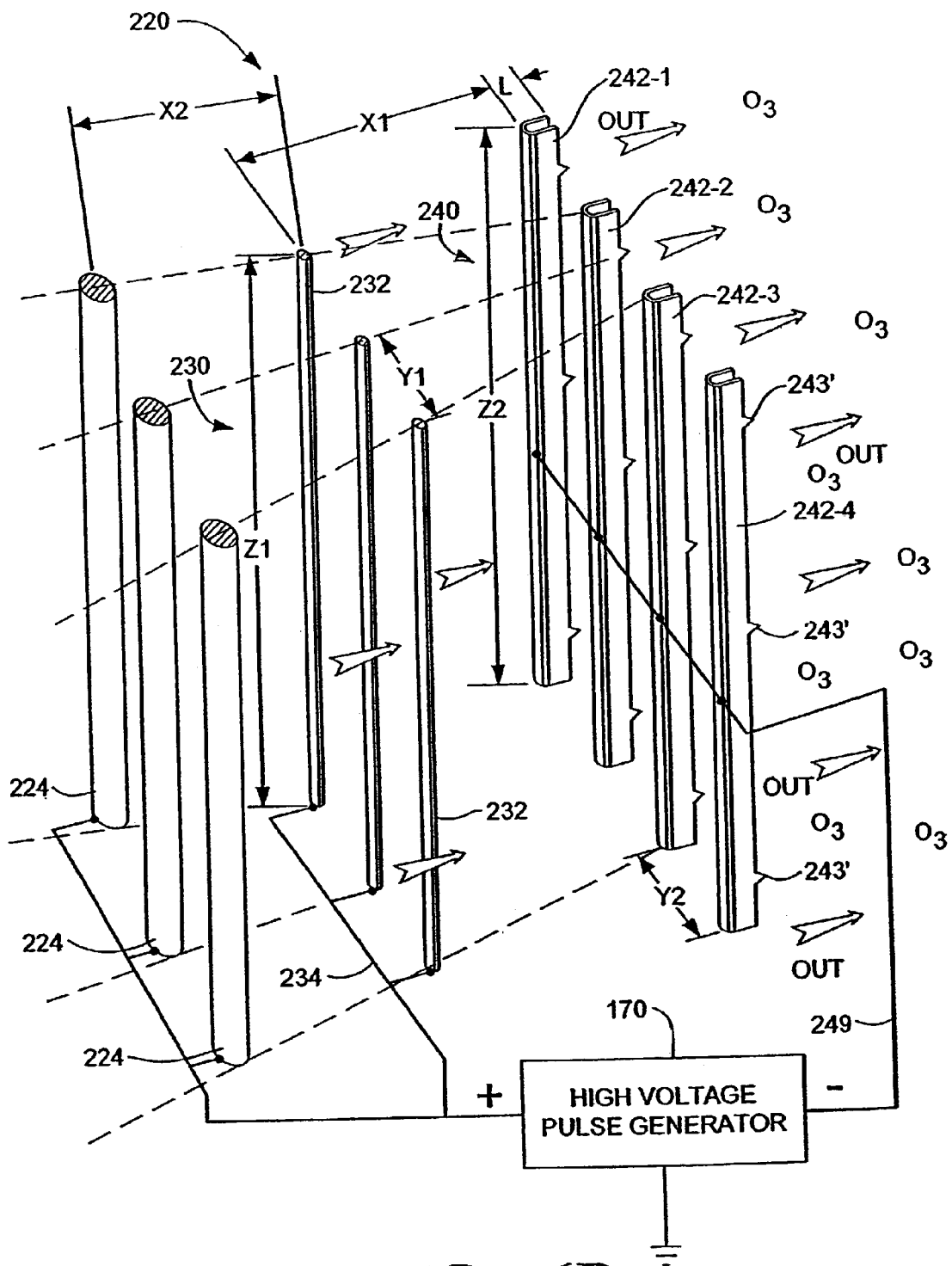

A third leading or focus electrode 224 is located upstream of each first electrode 232. The innermost third focus electrode 224b is located directly upstream of the first electrode 232-2, as shown by extension line B. Extension line B is located midway between the second electrodes 242-2, 242-3. The third focus electrodes 224a, 224c are at an angle with respect to the first electrodes 232-1, 232-3. For example, the third focus electrode 224a is upstream to the first electrode 232-1 along a line extending from the middle of the nose 246 of the second electrode 242-2 extending through the center of the first electrode 232-1, as shown by extension line A. The third electrode 224c is located upstream of the first electrode 232-3 along a line extending from the center of the nose 246 of the second electrode 242-3 through the center of the first electrode 232-3, as shown by extension line C. Accordingly and preferably the focus electrodes fan out relative to the first electrodes as an aid for directing the flow of ions and charged particles. FIG. 6B illustrates that the third focus electrodes 224 and the first electrode 232 may be electrically connected to the high voltage generator 170 by conductor 234.

Figure 6C:
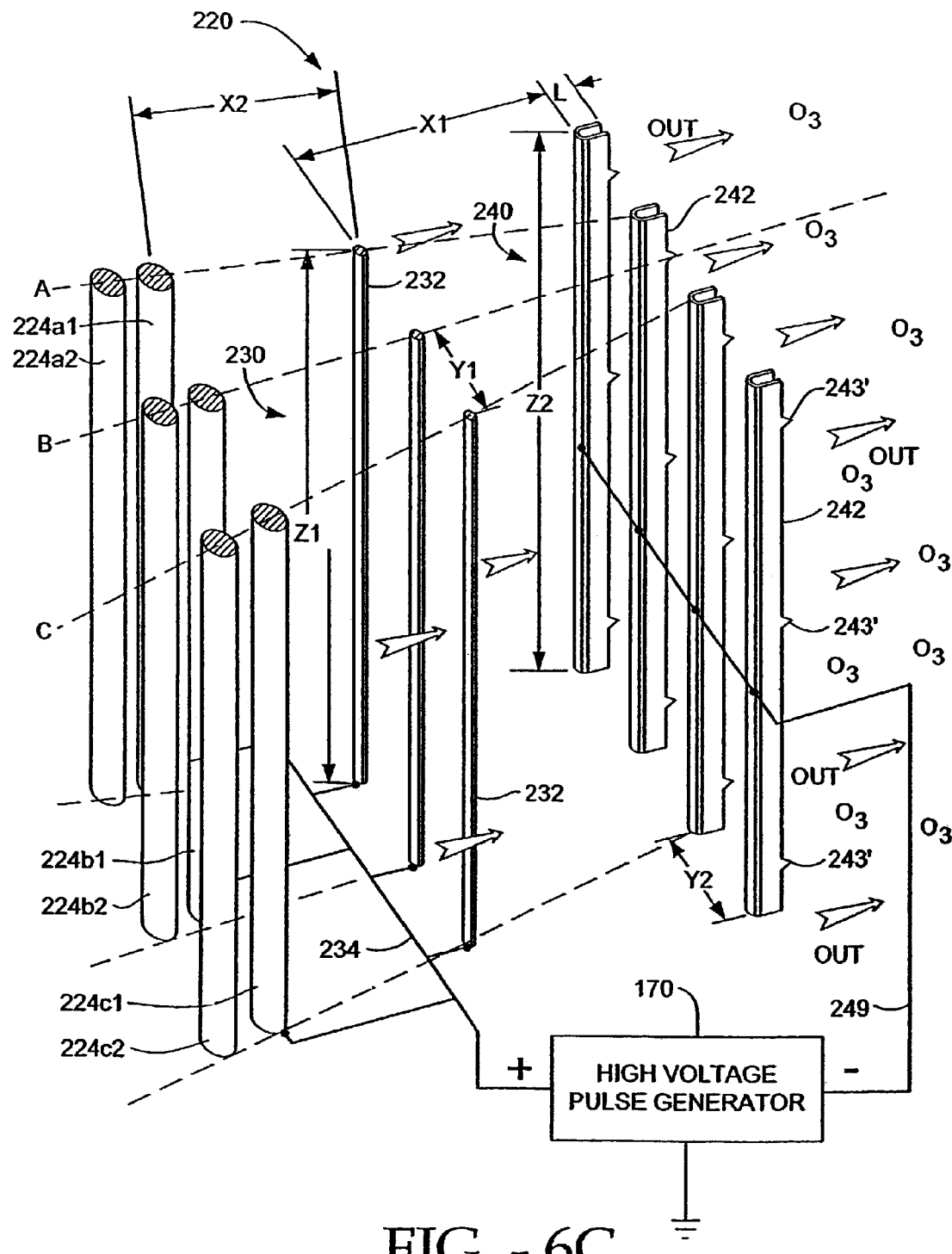

FIG. 6C illustrates that a pair of third focus electrodes 224 may be located upstream of each first electrode 232. Preferably, the multiple third focus electrodes 224 are in-line and symmetrically aligned with each other. For example, the third focus electrode 224a2 is in-line and symmetrically aligned with the third focus electrode 224a1, along extension line A. As previously mentioned, preferably only third focus electrodes 224a1, 224b1, 224c1 are electrically connected with the first electrodes 232 by conductor 234. It is also within the scope of the present invention to have none or all of the third focus electrodes 224 electrically connected to the high voltage generator 170.

Figure 6D:
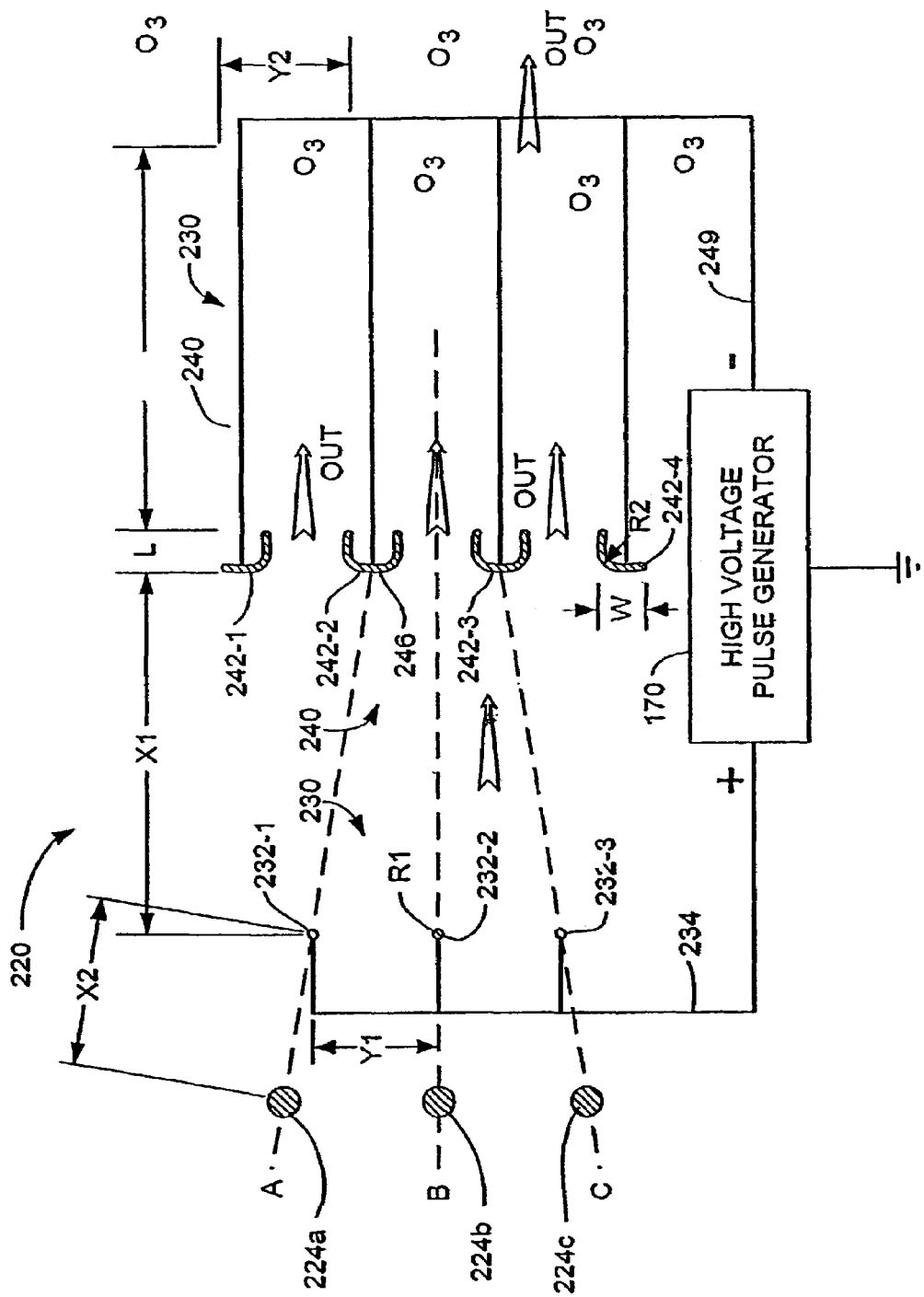

FIG. 6D illustrates third focus electrodes 224 added to the electrode assembly 220 shown in FIG. 4D. Preferably, a third focus electrode 224 is located upstream of each first electrode 232. For example, the third focus electrode 224b is in-line and symmetrically aligned with the first electrode 232-2, as shown by extension line B. Extension line B is located midway between the second electrodes 242-2, 242-3. The third focus electrode 224a is in-line and symmetrically aligned with the first electrode 232-1, as shown by extension line A. Similarly, the third electrode 224c is in-line and symmetrically aligned with the first electrode 232-3, as shown by extension line C. Extension lines A-C extend from the middle of the nose 246 of the "U"-shaped second electrodes 242-2, 242-3 through the first electrodes 232-1, 232-3, respectively. In a preferred embodiment, the third electrodes 224a, 224b, 224c with the high voltage generator 170 by the conductor 234. This embodiment can also include a pair of third focus electrodes 224 upstream of each first electrode 232 as is depicted in FIG. 6C.

FIGS. 7A-7C

Figure 7A:
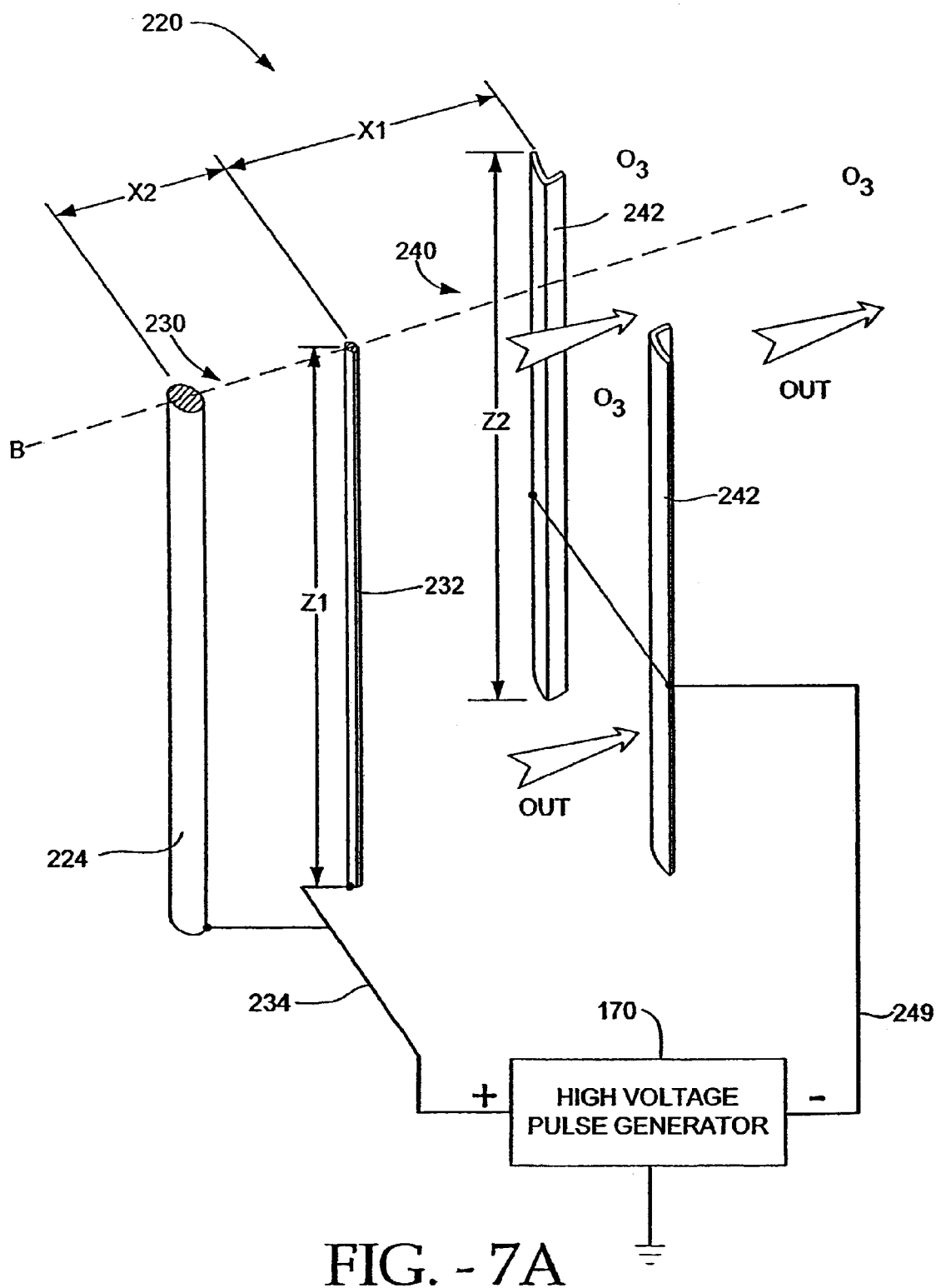
FIGS. 7A-7C.
Figure 7B:
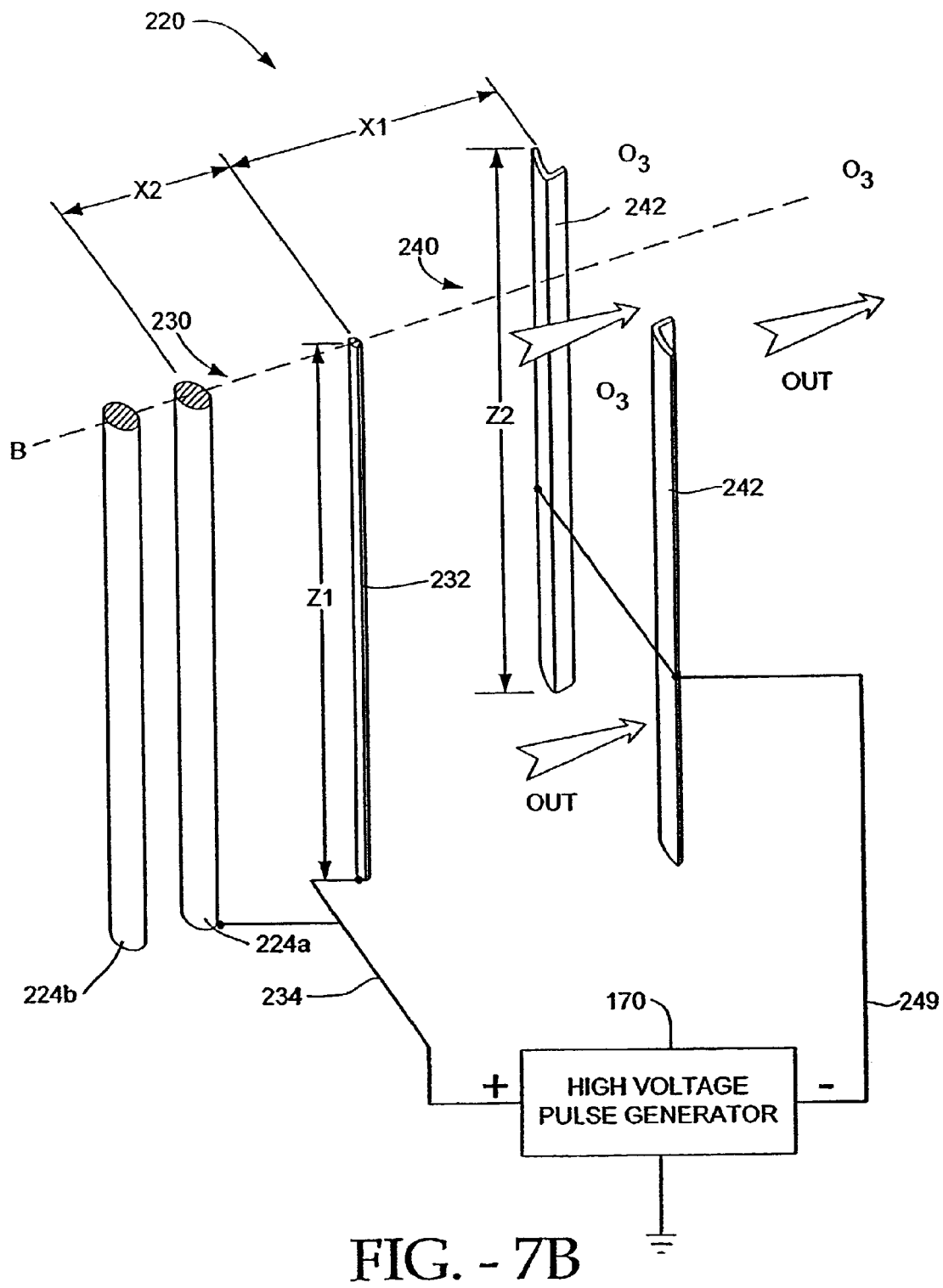
Figure 7C:
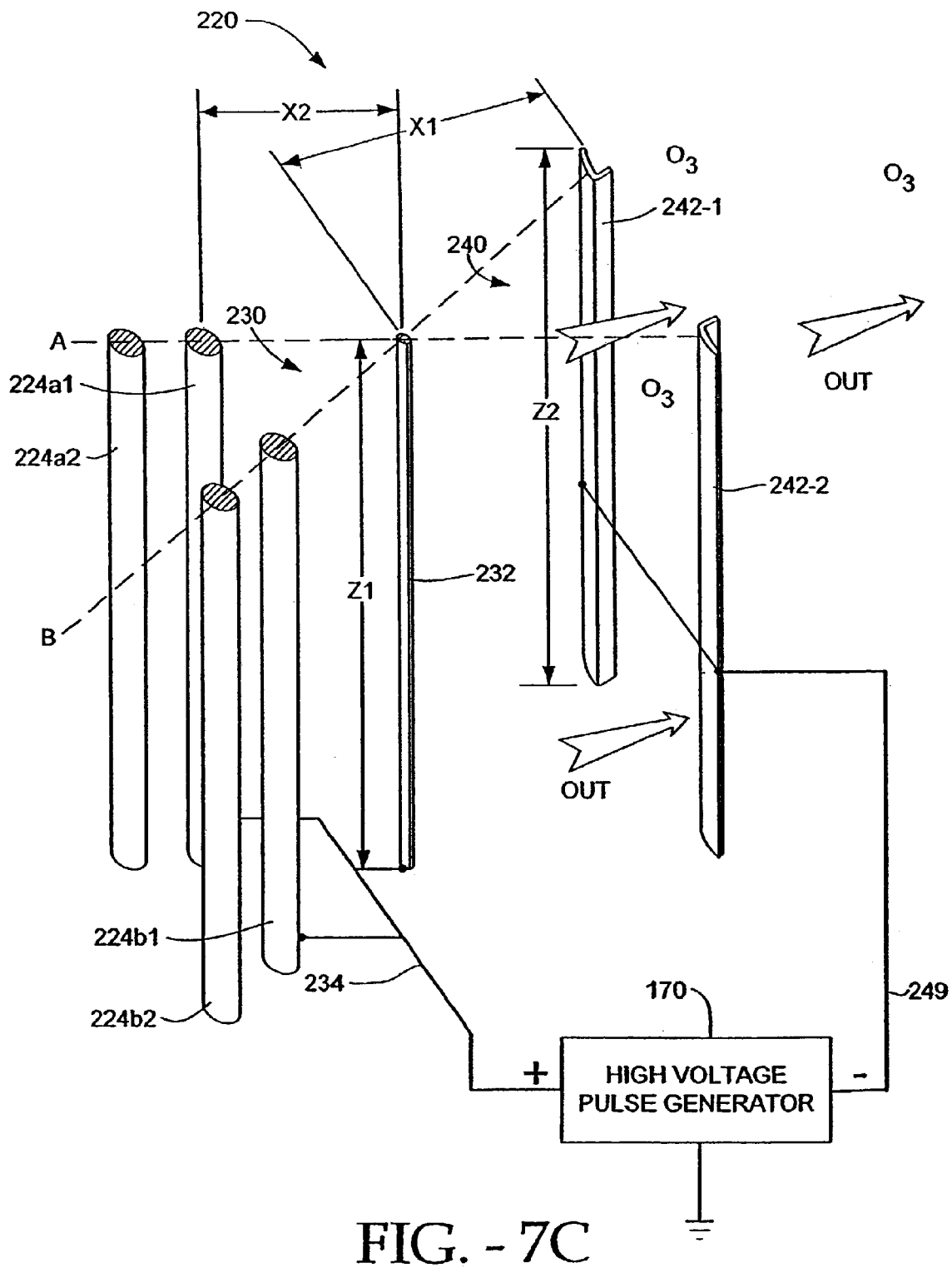

FIGS. 7A-7C illustrate that the electrode assembly 220 shown in FIG. 4E can include a third focus electrode upstream of the first array of electrodes 230 comprising a single wire electrode 232. Preferably, the center of the third focus electrode 224 is in-line and symmetrically aligned with the center of the first electrode 232, as shown by extension line B. Extension line B is located midway between the second electrodes 242. The distances X1, X2, Y1, Y2, Z1 and Z2 are similar to the embodiments previously described. The first electrode 232 and the second electrode 242 may be electrically connected to the high-voltage generator 170 by conductor 234, 249 respectively. It is within the scope of the present invention to connect the first and second electrodes to opposite ends of the high voltage generator 170 (e.g., the first electrode 232 may be negatively charged and the second electrode 242 may be positively charged). In a preferred embodiment the third focus electrode 224 is also electrically connected to the high voltage generator 170.

FIG. 7B illustrates that a pair of third focus electrodes 224a, 224b may be located upstream of the first electrode 232. The third focus electrodes 224a, 224b are inline and symmetrically aligned with the first electrode 232, as shown by extension line B. Extension line B is located midway between the second electrodes 242. Preferably, the third focus electrode 224b is upstream of third focus electrode 224a a distance equal to the diameter of a third focus electrode 224. In a preferred embodiment, only the third focus electrode 224a is electrically connected to the high voltage generator 170. It is within the scope of the present invention to electrically connect both third focus electrodes 224a, 224b to the high voltage generator 170.

FIG. 7C illustrates that each third focus electrode 224 can be located at an angle with respect to the first electrode 232. Similar to the previous embodiments, the third focus electrode 224a1 and 224b1 is located a distance X2 upstream from the first electrode 232. By way of example only, the third focus electrodes 224a1, 224a2 are located along a line extending from the middle of the second electrode 242-2 through the center of the first electrode 232, as shown by extension line A. Similarly, the third focus electrodes 224b1, 224b2 are along a line extending from the middle of the second electrode 242-1 through the middle of the first electrode 232, as shown by extension line B. The third focus electrode 224a2 is in-line and symmetrically aligned with the third focus electrode 224a1 along extension line A. Similarly, the third focus electrode 224b2 is in line and symmetrically aligned with the third focus electrode 224b1 along extension line B. The third focus electrodes 224 are fanned out and form a "V" pattern upstream of first electrode 232. In a preferred embodiment, only the third focus electrodes 224a1 and 224b1 are electrically connected to the high-voltage generator 170 by conductor 234. It is within the scope of the invention to electrically connect the third focus electrodes 224a and 224b2 to the high voltage generator 170.

FIGS. 8A-8B

Figure 8A:
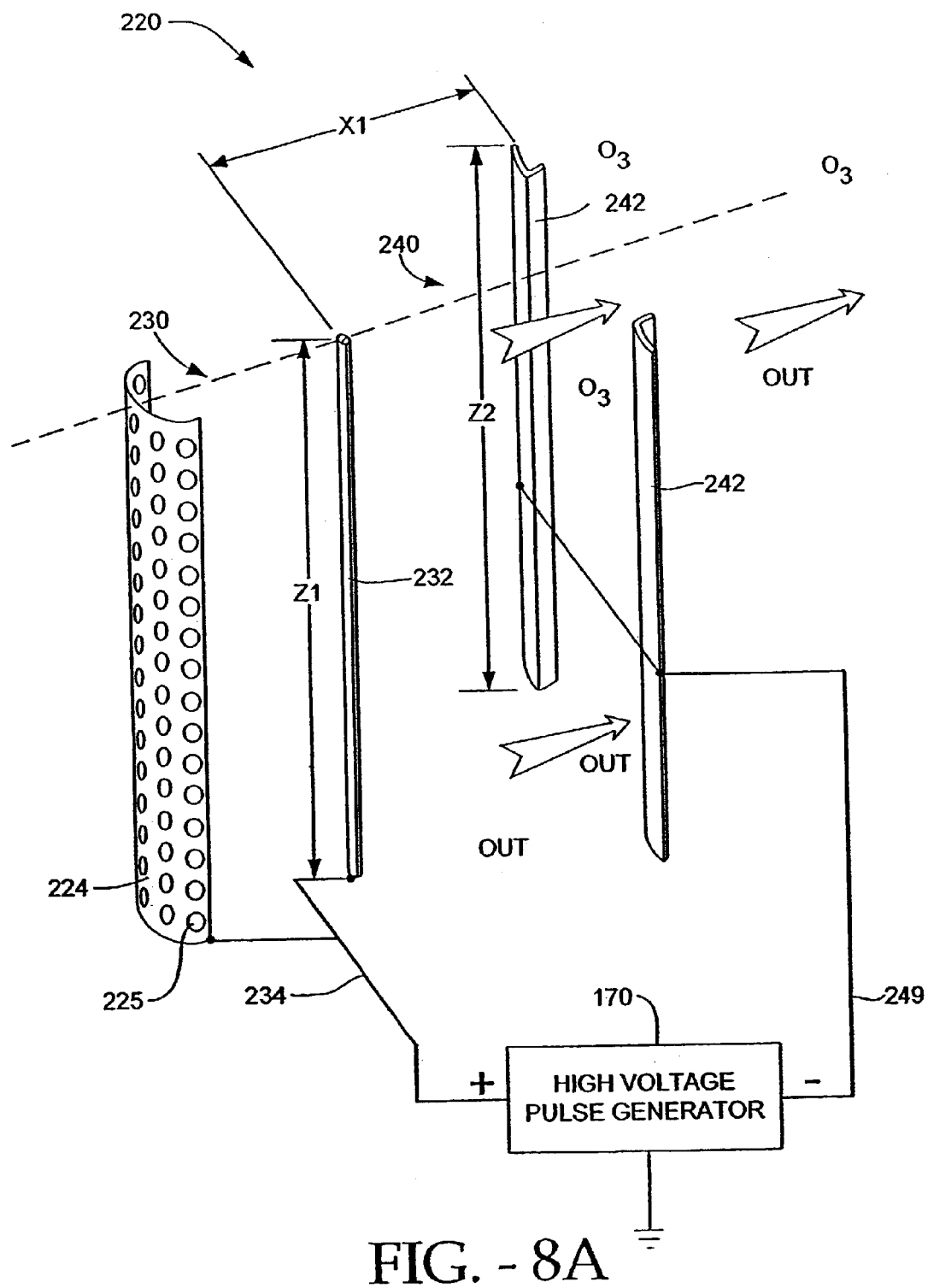
FIGS. 8A-8C.

The previously described embodiments of the electrode assembly 220 disclose a rod-shaped third focus electrode 224 upstream of each first electrode 232. FIG. 8A illustrates an alternative configuration for the third focus electrode 224. By way of example only, the electrode assembly 220 may include a "U"-shaped or possibly "C"-shaped third focus electrode 224 upstream of each first electrode 232. Further the third focus electrode 224 can have other curved configurations such as, but not limited to, circular-shaped, elliptical-shaped, and parabolically-shaped other concave shapes facing the first electrode 232. In a preferred embodiment, the third focus electrode 224 has holes 225 extending through, forming a perforated surface to minimize the resistance of the third focus electrode 224 on the airflow rate.

In a preferred embodiment, the third focus electrode 224 is electrically connected to the high voltage generator 170 by conductor 234. The third focus electrode 224 in FIG. 8A is preferably not an ion emitting surface. Similar to previous embodiments, the third focus electrode 224 generates a positive electric field and pushes or repels the electric field generated by the first electrode 232 towards the second array 240.

Figure 8B:
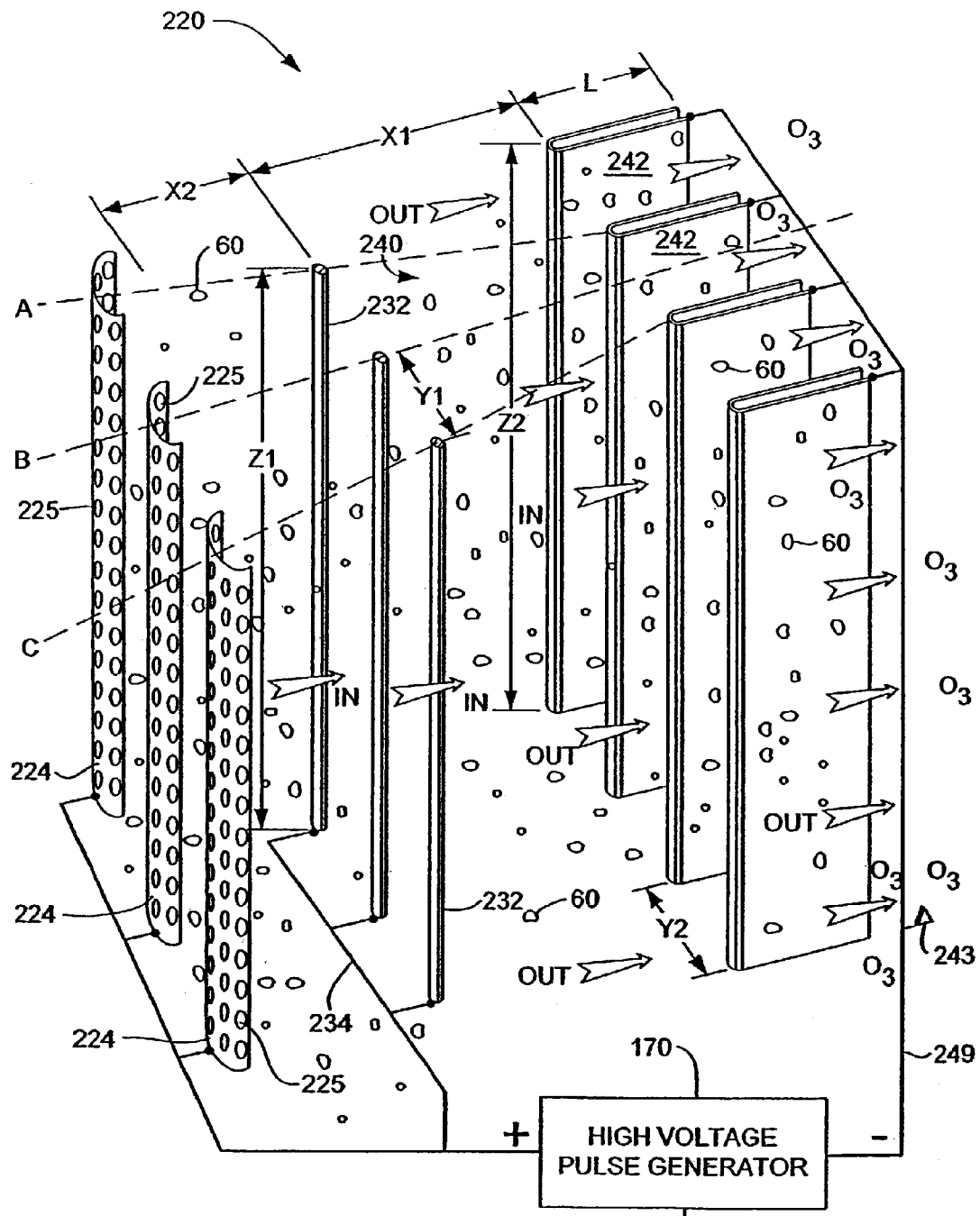

FIG. 8B illustrates that a perforated "U"-shaped or "C"-shaped third focus electrode 224 can be incorporated into the electrode assembly 220 shown in FIG. 4A. Even though only two configurations of the electrode assembly 220 are shown with the perforated "U"-shaped third focus electrode 224, all the embodiments described in FIGS. 5A-12C may incorporate the perforated "U"-shaped third focus electrode 224. It is also within the scope of the invention to have multiple perforated "U"-shaped third focus electrodes 224 upstream of each first electrode 232. Further in other embodiment the "U"-shaped third focus electrode 224 can be made of a screen or a mesh.

Figure 8C:
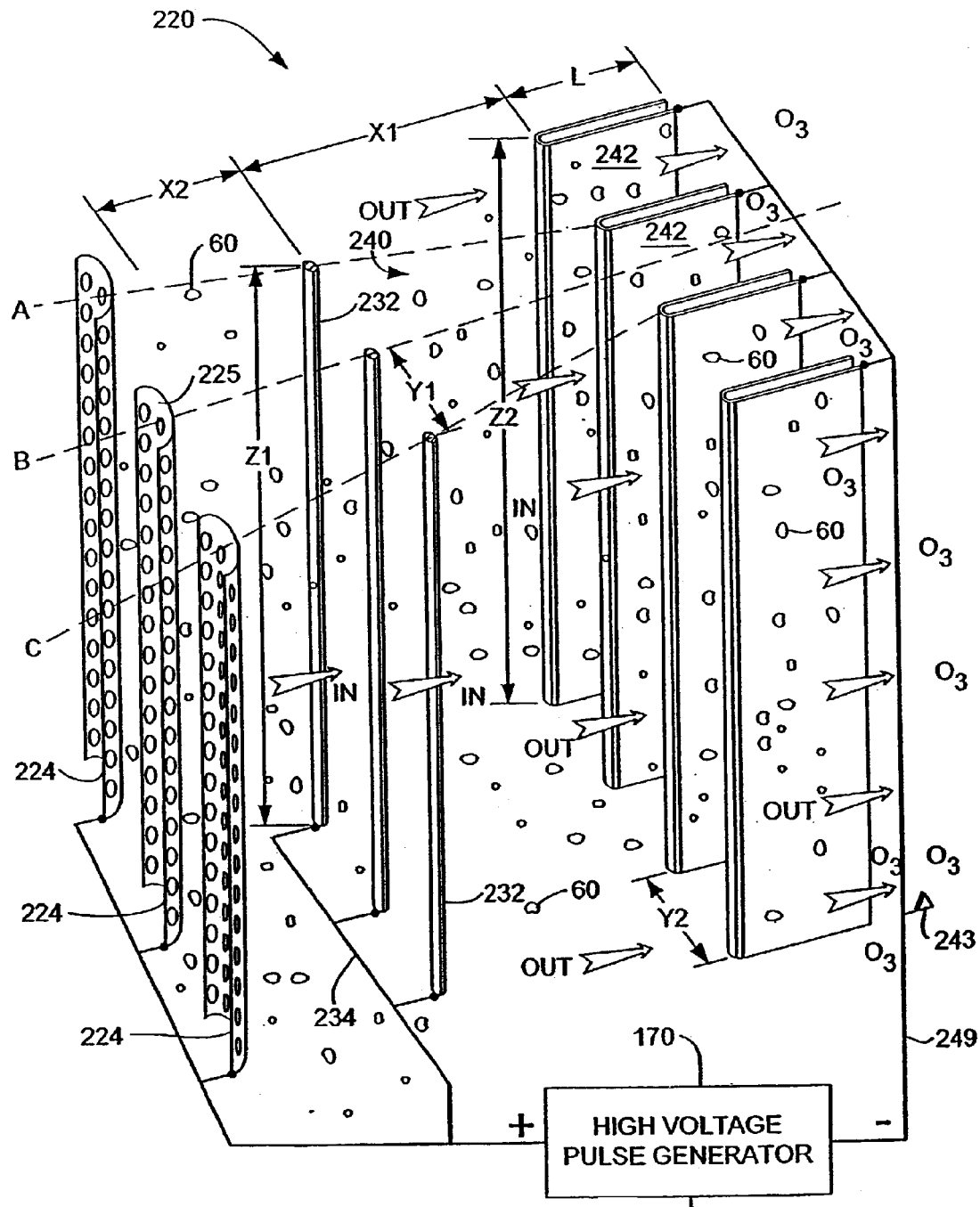

FIG. 8C illustrates third focus electrodes 224 similar to those depicted in FIG. 8B, except that the third focus electrodes 224 are rotated by 180° to preset a convex surface facing to the first electrodes 232 in order to focus and direct the field of ions and airflow from the first electrode 232 toward the second electrode 242. These third focus electrodes 224 shown in FIGS. 8A-8C are located along extension lines A, B, C similar to previously described embodiments.

FIGS. 9A-9C

FIG. 9A illustrates a pin-ring configuration of the electrode assembly 220. The electrode assembly 220 contains a cone-shaped or triangular-shaped first electrode 232, a ring-shaped second electrode 242 downstream of the first electrode 232, and a third focus electrode 250 upstream of the first electrode 232. The third focus electrodes 250 may be electrically connected to the high voltage generator 170. Preferably the focus electrode 250 is spaced from the first electrode 232 a distance that is in accordance with the other embodiments described herein. Alternatively, the third focus electrode 250 can have a floating potential. As indicated by phantom elements 232', 242', the electrode assembly 220 can comprise a plurality of such pin-like and ring-like elements. The plurality of pin-ring configurations as depicted in FIG. 9A can be positioned one above the other along the elongated housing of the invention. Such a plurality of pin-ring configurations can of course operate in another embodiment without the third focus electrode. It is understood that this plurality of pin-ring configurations can be upstanding and elongated along the elongated direction of said housing and can replace the first and second electrodes shown, for example, in FIG. 2B and be removable much as the second electrode in FIG. 2B is removable. Preferably, the first electrode 232 is tungsten, and the second electrode 242 is stainless steel. Typical dimensions for the embodiment of FIG. 9A are L1≈10 millimeters, X1≈9.5 millimeters, T≈0.5 millimeters and the diameter of the opening 246≈12 millimeters.

The electrical properties and characteristics of the third focus electrode 250 is similar to the third focus electrode 224 described in previous embodiments. In contrast to the rod-shaped physical characteristic of the previous embodiments, the shape the third focus electrode 250 is a concave disc, with the concave surface preferably facing toward the second electrodes 242. The third focus electrode 250 preferably has holes extending therethrough to minimize the disruption in airflow. It is within the scope of the present invention for the third focus electrode 250 to comprise other shapes such as, but not limited to, a convex disc a parabolic disc, a spherical disc, or other convex or concave shapes or a rectangle, or other planar surface and be within the spirit and scope of the invention. The diameter of the third focus electrode 250 is preferably at least fifteen times greater than the diameter of the first electrode 232. The focus electrode 250 can also be made of a screen or a mesh.

The second electrode 242 has an opening 246. The opening 246 is preferably circular in this embodiment. It is within the scope of the present invention that the opening 246 can comprise other shapes such as, but not limited to, rectangular, hexagonal or octagonal. The second electrode 242 has a collar 247 (see FIG. 9B) surrounding the opening 246. The collar 247 attracts the dust contained within the airstream passing through the opening 246. As seen in the FIGS. 9B and 9C the collar 247 includes a downstream extending tubular portion 248 which can collect particles. As a result, the airstream emitted by the electrode assembly 220 has a reduced dust content.

Other similar pin-ring embodiments are shown in FIGS. 9B-9C. For example, the first electrode 232 can comprise a rod-shaped electrode having a tapered end. In FIG. 9B, a detailed cross-sectional view of the central portion of the second electrode 242 in FIG. 9A is shown. Preferably, the collar 247 is positioned in relation to the first electrode 232, such that the ionization paths from the distal tip of the first electrode 232 to the collar 247 have substantially equal path lengths. Thus, while the distal tip (or emitting tip) of the first electrode 232 is advantageously small to concentrate the electric field, the adjacent regions of the second electrode 242 preferably provide many equidistant inter-electrode paths. The lines drawn in phantom in FIGS. 9B and 9C depict theoretical electric force field lines emanating from the first electrode 232 and terminating on the curved surface of the second electrode 242. Preferably, the bulk of the field emanates within about 45 degrees of coaxial axis between the first electrode 232 and the second electrode 242.

In FIG. 9C, one or more first electrodes 232 are replaced by a conductive block 232" of carbon fibers, the block having a distal surface in which projecting fibers 233-1, . . . 233-N take on the appearance of a "bed of nails." The projecting fibers can each act as an emitter electrode and provide a plurality of emitting surfaces. Over a period of time, some or all of the electrodes will literally be consumed, where upon the block 232" may be replaced. Materials other than graphite may be used for block 232" providing that the material has a surface with projecting conductive fibers such as 233-N.

Electrode Assembly With a Downstream Trailing Electrode

FIGS. 10A-10D

Figure 10A:
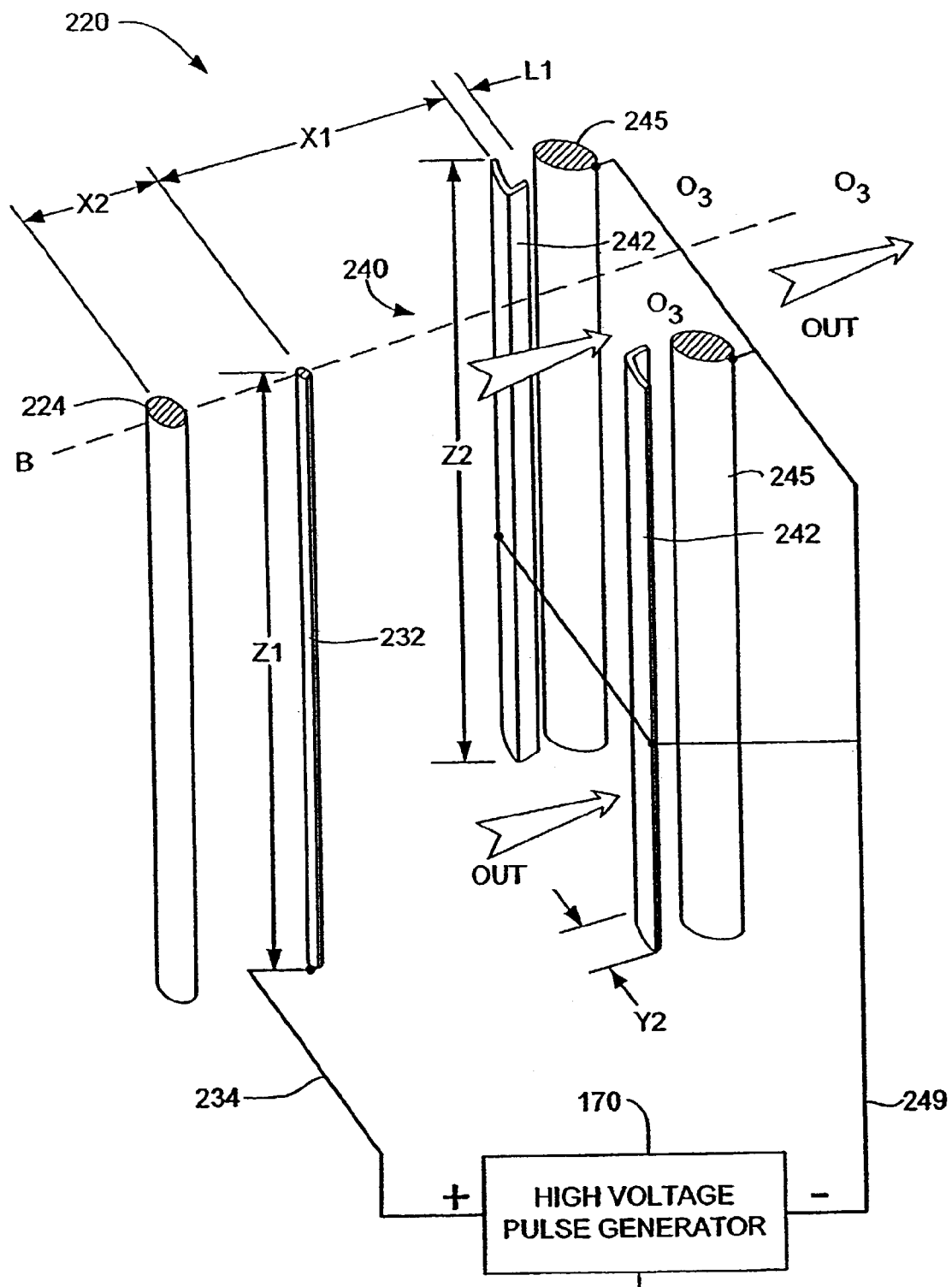
FIGS. 10A-10D.
Figure 10B:
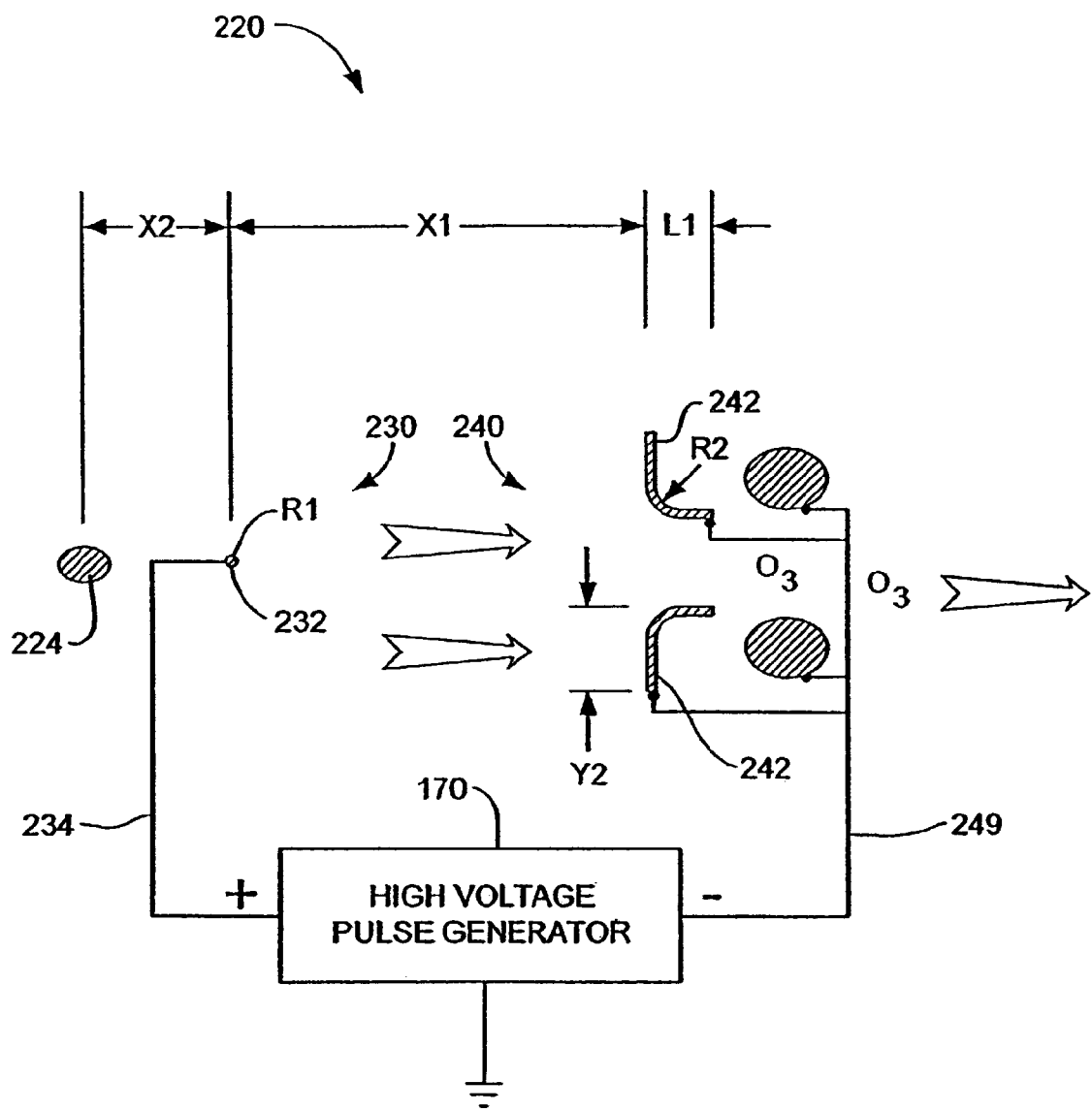
Figure 10C:
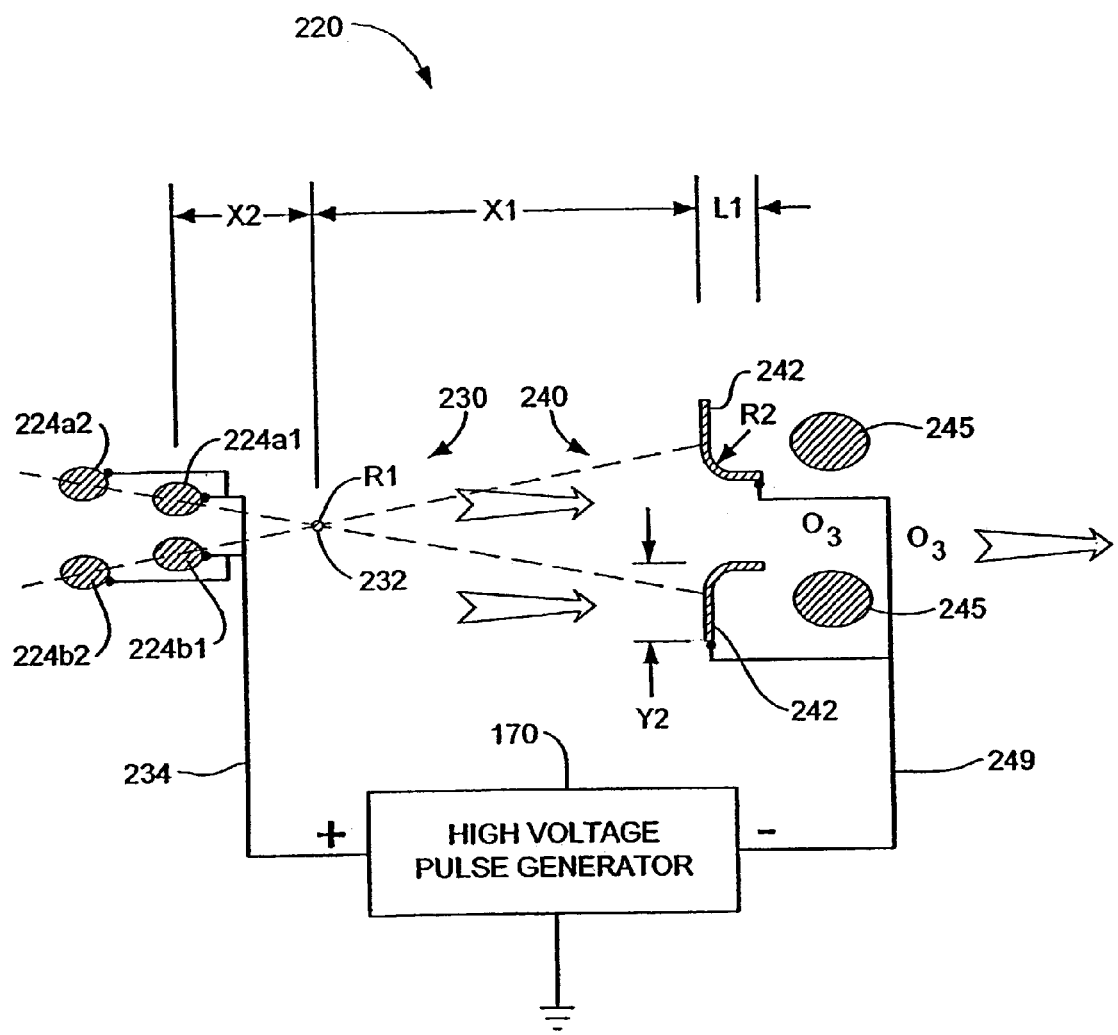
Figure 10D:
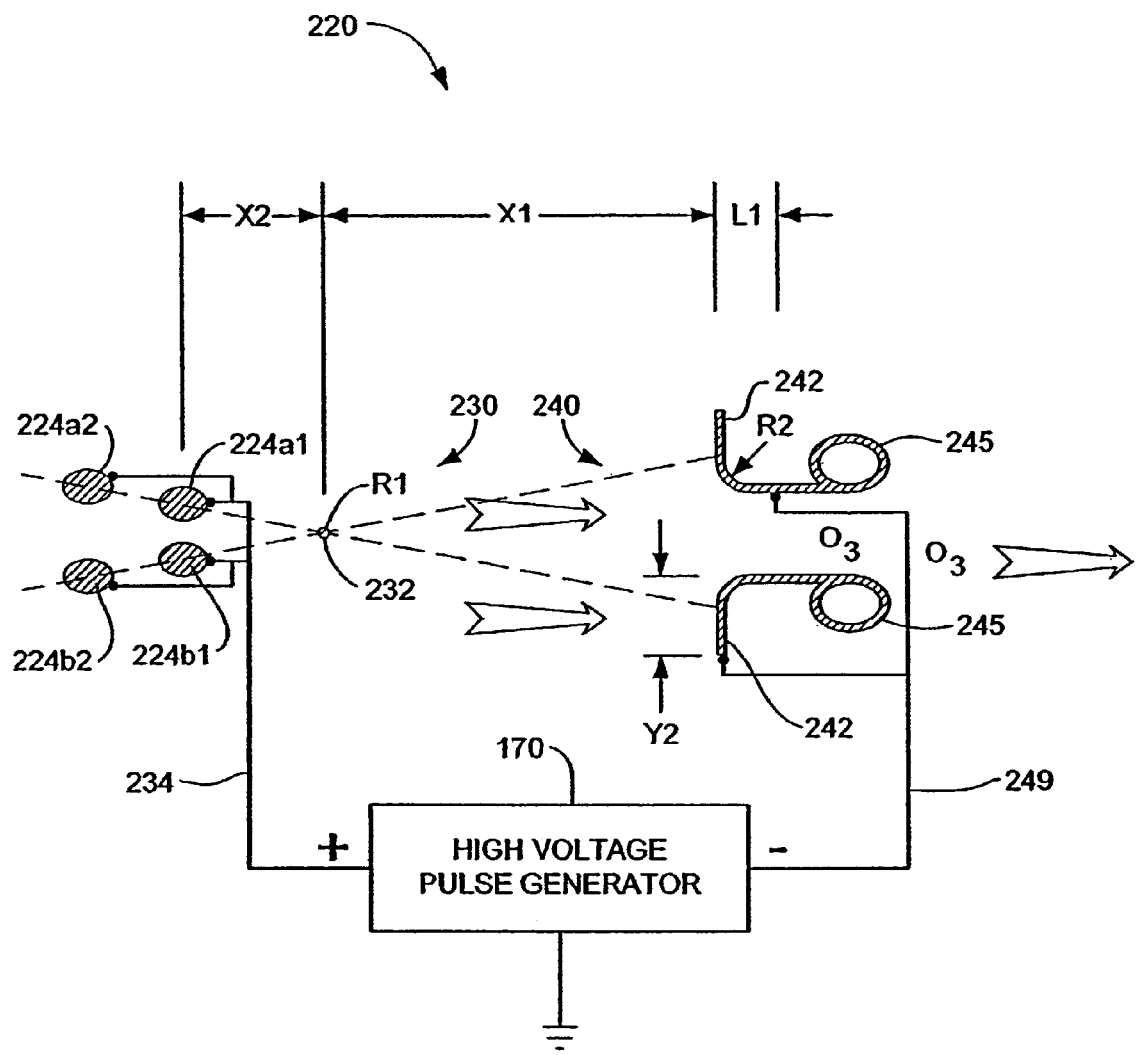

FIGS. 10A-10C illustrate an electrode assembly 220 having an array of trailing electrodes 245 added to an electrode assembly 220 similar to that shown in FIG. 7A. It is understood that an alternative embodiment similar to FIG. 10A can include a trailing electrode or electrodes without any focus electrodes and be within the spirit and scope of the inventions. Referring now to FIGS. 10A-10B, each trailing electrode 245 is located downstream of the second array of electrodes 240. Preferably, the trailing electrodes are located downstream from the second electrodes 242 by at least three times the radius R2 (see FIG. 10B). Further, the trailing electrodes 245 are preferably directly downstream of each second electrode 242 so as not to interfere with the flow of air. Also, the trailing electrode 245 is aerodynamically smooth, for example, circular, elliptical, or teardrops shaped in cross-section so as not to unduly interfere with the smoothness of the airflow thereby. In a preferred embodiment, the trailing electrodes 245 are electrically connected to the same outlet of the high voltage generator 170 as the second array of electrodes 240. As shown in FIG. 10A, the second electrodes 242 and the trailing electrodes 245 have a negative electrical charge. This arrangement can introduce more negative charges into the air stream. Alternatively, the trailing electrodes 245 can have a floating potential if they are not electrically connected. The trailing electrodes 245 can also be grounded in other embodiments. Further alternatively, as shown in FIG. 10D, the trailing electrode 245 can be formed with the second electrode out of a sheet of metal formed in the shape of the second electrode and then extending to the position of the trailing electrode and formed as a hollow trailing electrode with a peripheral wall that is about the shape of the outer surface of the trailing electrode 245 depicted in FIG. 10C.

When the trailing electrodes 245 are electrically connected to the high voltage generator 170, the positively charged particles within the airflow are also attracted to and collect on, the trailing electrodes. In a typical electrode assembly with no trailing electrode 245, most of the particles will collect on the surface area of the second electrodes 242. However, some particles will pass through the unit 200 without being collected by the second electrodes 242. Thus, the trailing electrodes 245 serve as a second surface area to collect the positively charged particles. The trailing electrodes 245 also can deflect charged particles toward the second electrodes.

The trailing electrodes 245 preferably also emit a small amount of negative ions into the airflow. These negative ions will neutralize the positive ions emitted by the first electrodes 232. If the positive ions emitted by the first electrodes 232 are not neutralized before the airflow reaches the outlet 260, the outlet fins 212 can become electrically charged and particles within the airflow may tend to stick to the fins 212. If this occurs, eventually the amount of particles collected by the fins 212 will block or minimize the airflow exiting the unit 200.

FIG. 10C illustrates another embodiment of the electrode assembly 200, having trailing electrodes 245 added to an embodiment similar to that shown in FIG. 7C. The trailing electrodes 245 are located downstream of the second array 240 similar to the previously described embodiments above. It is within the scope of the present invention to electrically connect the trailing electrodes 245 to the high voltage generator 170. As shown in FIG. 10C, all of the third focus electrodes 224 are electrically connected to the high voltage generator 170. In a preferred embodiment, only the third focus electrodes 224a1, 224b1 are electrically connected to the high voltage generator 170. The third focus electrodes 224a2, 224b2 have a floating potential.

Electrode Assemblies with Various Combinations of Focus Electrodes, Trailing Electrodes and Enhanced Second Electrodes with Protective Ends

FIGS. 11A-11D

Figure 11A:
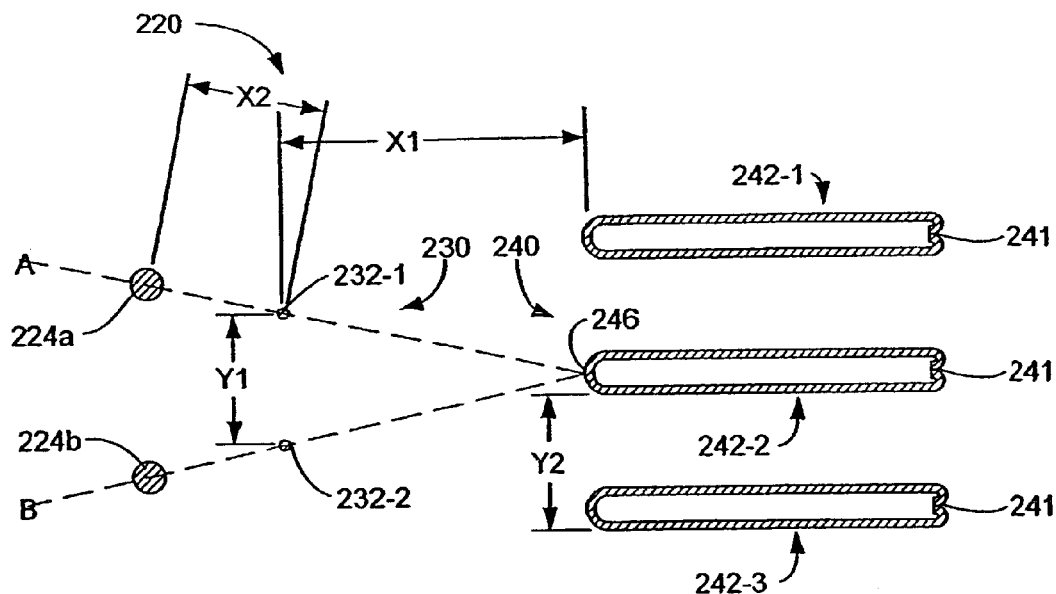
FIGS. 11A-11F.

FIG. 11A illustrates an electrode assembly 220 that includes a first array of electrodes 230 having two wire-shaped electrodes 232-1, 232-2 (generally referred to as "electrode 232") and a second array of electrodes 240 having three "U"-shaped electrodes 242-1, 242-2, 242-3 (generally referred to as "electrode 242"). This configuration is in contrast to, for example, the configurations of FIG. 9A, wherein there are three first emitter electrodes 232 and four second collector electrodes 242.

Upstream from each first electrode 232, at a distance X2, is a third focus electrode 224. Each third focus electrode 224a, 224b is at an angle with respect to a first electrode 232. For example, the third focus electrode 224a is preferably along a line extending from the middle of the nose 246 of the second electrode 242-2 through the center of the first electrode 232-1, as shown by extension line A. The third focus electrode 224a is in-line and symmetrically aligned with the first electrode 232-1 along extension line A. Similarly, the third focus electrode 224b is located along a line extending from middle of the nose 246 of the second electrode 242-2 through the center of the first electrode 232-2, as shown by extension line B. The third focus electrode 224b is in-line and symmetrically aligned with the first electrode 232-2 along extension line B. As previously described, the diameter of each third focus electrode 224 is preferably at least fifteen times greater than the diameter of the first electrode 232.

As shown in FIG. 11A, and similar to the embodiment shown in FIG. 5B, each second electrode preferably has a protective end 241. In a preferred embodiment, the third focus electrodes 224 are electrically connected to the high voltage generator 170 (not shown). It is within the spirit and scope of the invention to not electrically connect the third focus electrodes 224.

Figure 11B:
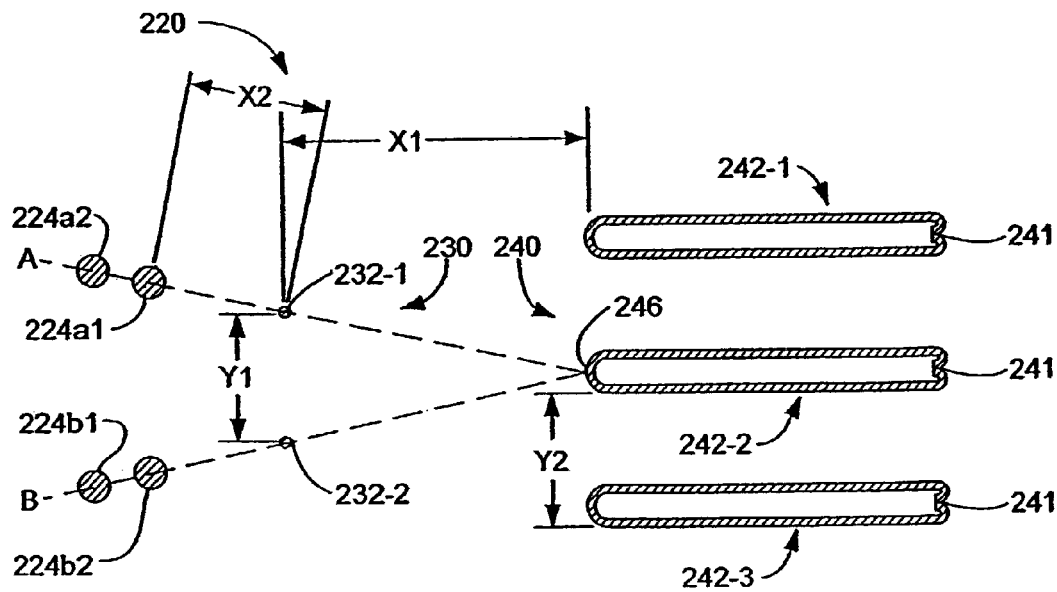

FIG. 11B illustrates that multiple third focus electrodes 224 may be located upstream of each first emitter electrode 232. For example, the third focus electrode 224a2 is in-line and symmetrically aligned with the third focus electrode 224a1 along extension line A. Similarly, the third focus electrode 224b2 is in-line and symmetrically aligned with the third focus electrode 242b1 along extension line B. It is within the scope of the present invention to electrically connect all, or none of, the third focus electrodes 224 to the high-voltage generator 170. In a preferred embodiment, only the third focus electrodes 224a1, 224b1 are electrically connected to the high voltage generator 170, with the third focus electrodes 224a2, 224b2 having a floating potential.

Figure 11C:
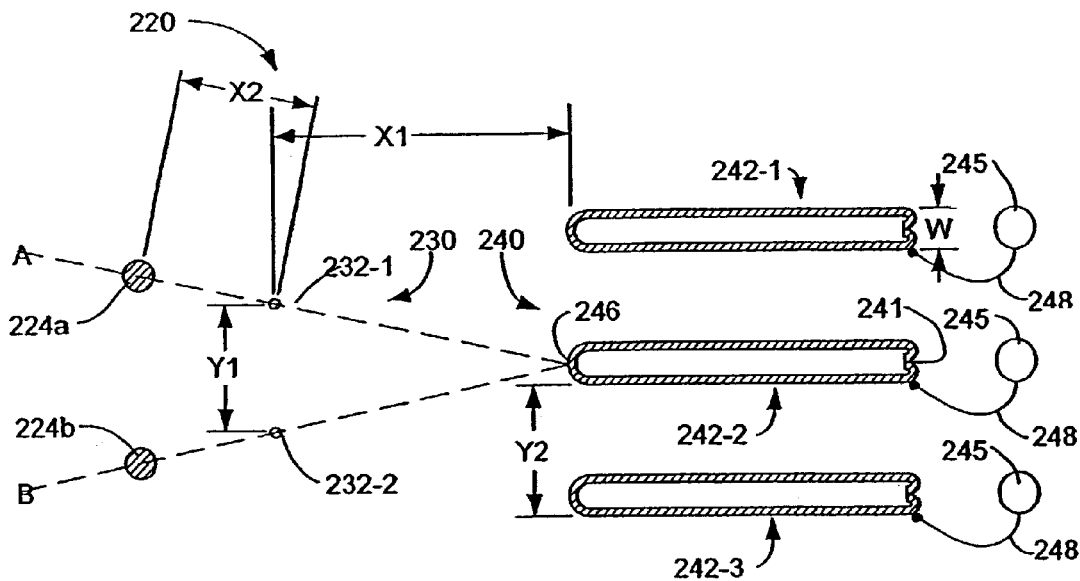

FIG. 11C illustrates that the electrode assembly 220 shown in FIG. 11A may also include a trailing electrode 245 downstream of each second electrode 242. Each trailing electrode 245 is in-line with the second electrode so as not to interfere with airflow past the second electrode 242. Each trailing electrode 245 is preferably located a distance downstream of each second electrode 242 equal to at least three times the width W of the second electrode 242. It is within the scope of the present invention for the trailing electrode to by located at other distances downstream. The diameter of the trailing anode 245 is preferably no greater than the width W of the second electrode 242 to limit the interference of the airflow coming off the second electrode 242.

One aspect of the trailing electrode 245 is to direct the air trailing off the second electrode 242 and provide a more laminar flow of air exiting the outlet 260. Another aspect of the trailing electrode 245 is to neutralize the positive ions generated by the first array 230 and collect particles within the airflow. As shown in FIG. 11C, each trailing electrode 245 is electrically connected to a second electrode 242 by a conductor 248. Thus, the trailing electrode 245 is negatively charged, and serves as a collecting surface, similar to the second electrode 242, attracts the positively charged particles in the airflow. As previously described, the electrically connected trailing electrode 245 also emits negative ions to neutralize the positive ions emitted by the first electrodes 232.

Figure 11D:
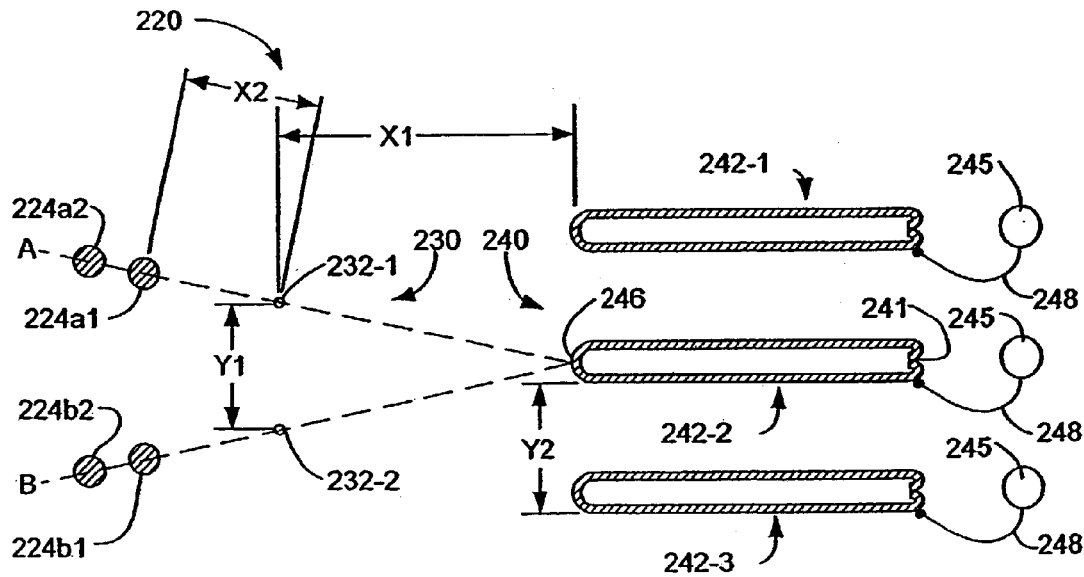

FIG. 11D illustrates that a pair of third focus electrodes 224 may be located upstream of each first electrode 232. For example, the third focus electrode 224a2 is upstream of the third focus electrode 224a1 so that the third focus electrodes 224a1, 224a2 are in-line and symmetrically aligned with each other along extension line A. Similarly, the third focus electrode 224b2 is in line and symmetrically aligned with the third focus electrode 224b1 along extension line B. As previously described, preferably only the third focus electrodes 224a1, 224b1 are electrically connected to the high voltage generator 170, while the third focus electrodes 224a2, 224b2 have a floating potential. It is within the spirit and scope of the present invention to electrically connect all, or none, of the third focus electrodes to the high voltage generator 170.

Electrode Assemblies with Second Collector Electrodes Having Interstitial Electrodes

FIGS. 11E-11F

Figure 11E:
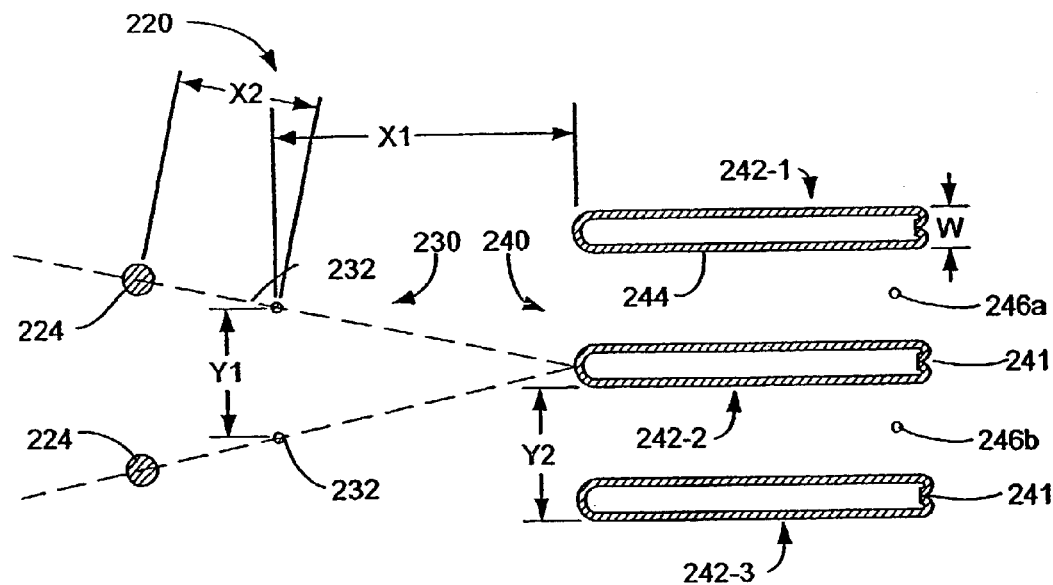

FIG. 11E illustrates another embodiment of the electrode assembly 220 with an interstitial electrode 246. In this embodiment, the interstitial electrode 246 is located midway between the second electrodes 242. For example, the interstitial electrode 246a is located midway between the second electrodes 242-1, 242-2, while the interstitial electrode 246b is located midway between second electrodes 242-2, 242-3. Preferably, the interstitial electrode 246a, 246b are electrically connected to the first electrodes 232, and generate an electrical field with the same positive or negative charge as the first electrodes 232. The interstitial electrode 246 and the first electrode 232 then have the same polarity. Accordingly, particles traveling toward the interstitial electrode 246 will be repelled by the interstitial electrode 246 towards the second electrodes 242. Alternatively, the interstitial electrodes can have a floating potential or be grounded.

It is to be understood that interstitial electrodes 246a, 246b may also be closer to one second collector electrode than to the other. Also, the interstitial electrodes 246a, 246b are preferably located substantially near or at the protective end 241 or ends of the trailing sides 244, as depicted in FIG. 11E. Still further the interstitial electrode can be substantially located along a line between the two trailing portions or ends of the second electrodes. These rear positions are preferred as the interstitial electrodes can cause the positively charged particle to deflect towards the trailing sides 244 along the entire length of the negatively charged second collector electrode 242, in order for the second collector electrode 242 to collect more particles from the airflow.

Still further, the interstitial electrodes 246a, 246b can be located upstream along the trailing side 244 of the second collector electrodes 244. However, the closer the interstitial electrodes 246a, 246b get to the nose 246 of the second electrode 242, generally the less effective interstitial electrodes 246a, 246b are in urging positively charged particles toward the entire length the second electrodes 242. Preferably, the interstitial electrodes 246a, 246b are wire-shaped and smaller or substantially smaller in diameter than the width "W" of the second collector electrodes 242. For example, the interstitial electrodes can have a diameter of, the same as, or on the order, of the diameter of the first electrodes. For example, the interstitial electrodes can have a diameter of one-sixteenth of an inch. Also, the diameter of the interstitial electrodes 246a, 246b is substantially less than the distance between second collector electrodes, as indicated by Y2. Further the interstitial electrode can have a length or diameter in the downstream direction that is substantially less than the length of the second electrode in the downstream direction. The reason for this size of the interstitial electrodes 246a, 246b is so that the interstitial electrodes 246a, 246b have a minimal effect on the airflow rate exiting the device 100 or 200.

Figure 11F:
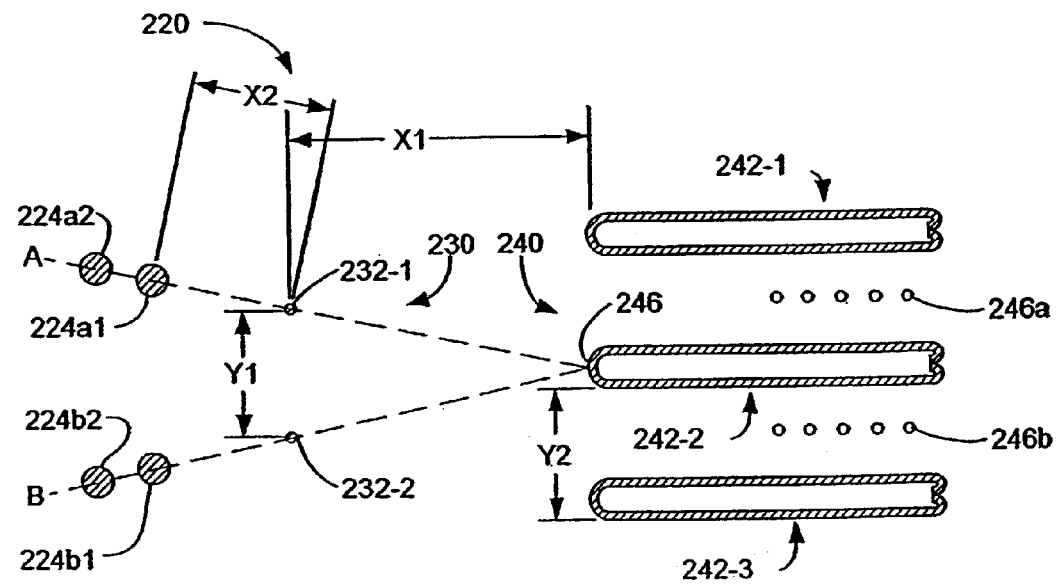

FIG. 11F illustrates that the electrode assembly 220 in FIG. 11E can include a pair of third electrodes 224 upstream of each first electrode 232. As previously described, the pair of third electrodes 224 are preferably in-line and symmetrically aligned with each other. For example, the third electrode 224a2 is in-line and symmetrically aligned with the third electrode 224a1 along extension line A. Extension line A preferably extends from the middle of the nose 246 of the second electrode 242-2 through the center of the first electrode 232-1. As previously disclosed, in a preferred embodiment, only the third electrodes 224a1, 224b1 are electrically connected to the high voltage generator 170. In FIG. 11F, a plurality of interstitial electrode 296a and 246b are located between the second electrodes 242. Preferably these interstitial electrodes are in-line and have a potential gradient with an increasing voltage potential on each successive interstitial electrode in the downstream direction in order to urge particles toward the second electrodes. In this situation the voltage on the interstitial electrodes would have the same sign as the voltage of the first electrode 232.

Electrode Assembly With an Enhanced First Emitter Electrode Being Slack

FIGS. 12A-12C

The previously described embodiments of the electrode assembly 220 include a first array of electrodes 230 having at least one wire-shaped electrode 232. It is within the scope of the present invention for the first array of electrodes 230 to contain electrodes consisting of other shapes and configurations.

Figure 12A:
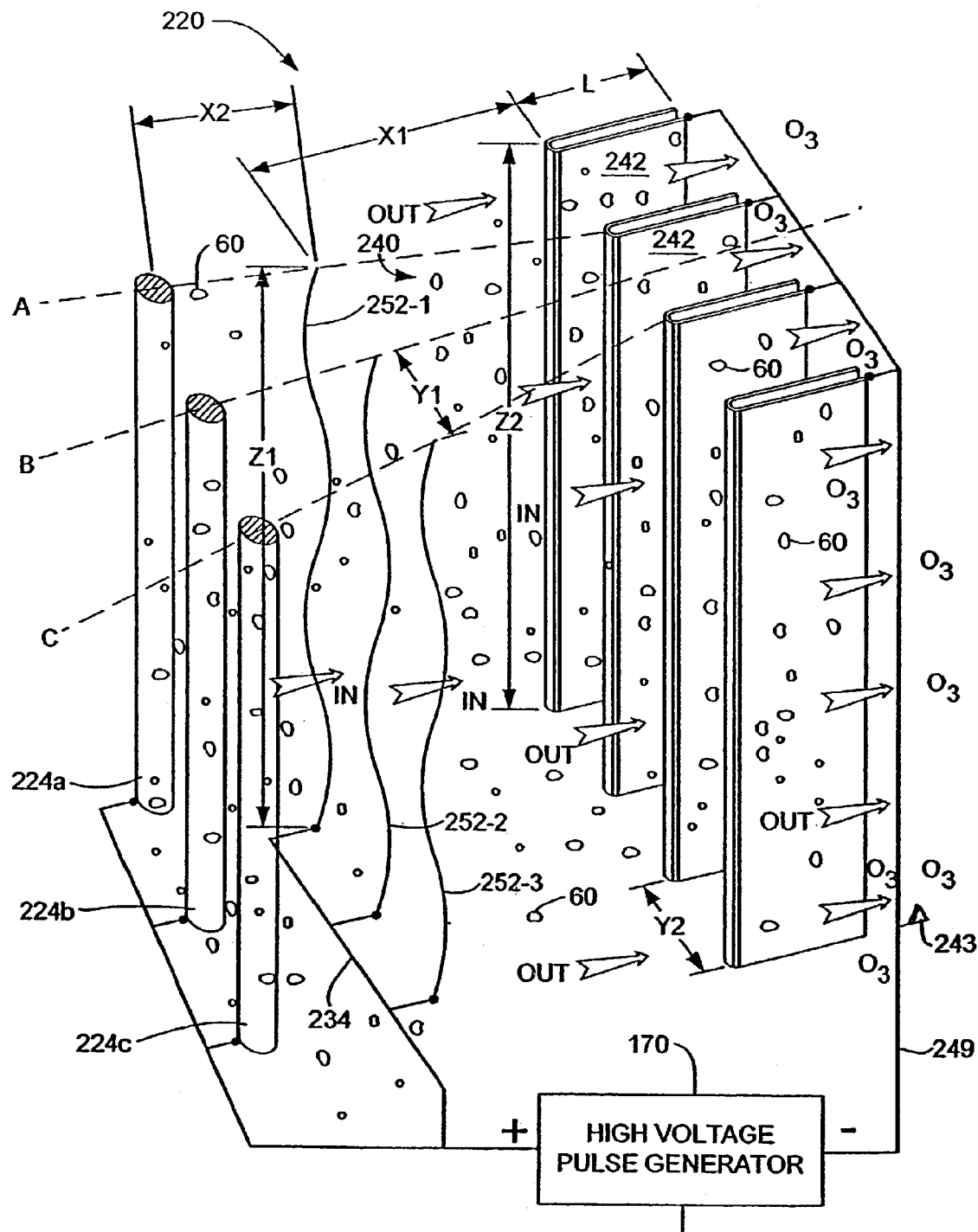
FIGS. 12A-12C.

FIG. 12A illustrates that the first array of electrodes 230 may include curved wire-shaped electrodes 252. The curved wire-shaped electrode 252 is an ion emitting surface and generates an electric field similar to the previously described wire-shaped electrodes 232. Also similar to previous embodiments, each second electrode 242 is "downstream," and each third focus electrode 224 is "upstream," to the curved wire-shaped electrodes 252. The electrical properties and characteristics of the second electrode 242 and the third focus electrode 224 are similar to the previously described embodiment shown in FIG. 5A. It is to be understood that an alternative embodiment of FIG. 12A can exclude the focus electrodes and be within the spirit and scope of the invention.

As shown in FIG. 12A, positive ions are generated and emitted by the first electrode 252. In general, the quantity of negative ions generated and emitted by the first electrode is proportional to the surface area of the first electrode. The height Z1 of the first electrode 252 is equal to the height Z1 of the previously disclosed wire-shaped electrode 232. However, the total length of the electrode 252 is greater than the total length of the electrode 232. By way of example only, and in a preferred embodiment, if the electrode 252 was straightened out the curved or slack wire electrode 252 is 15-30% longer than a rod or wire-shaped electrode 232. The electrode 252 is allowed to be slack to achieve the shorter height Z1. When a wire is held slack, the wire may form a curved shape similar to the first electrode 252 shown in FIG. 12A. The greater total length of the electrode 252 translates to a larger surface area than the wire-shaped electrode 232. Thus, the electrode 252 will generate and emit more ions than the electrode 232. Ions emitted by the first electrode array attach to the particulate matter within the airflow. The charged particulate matter is attracted to, and collected by, the oppositely charged second collector electrodes 242. Since the electrodes 252 generate and emit more ions than the previously described electrodes 232, more particulate matter will be removed from the airflow.

Figure 12B:
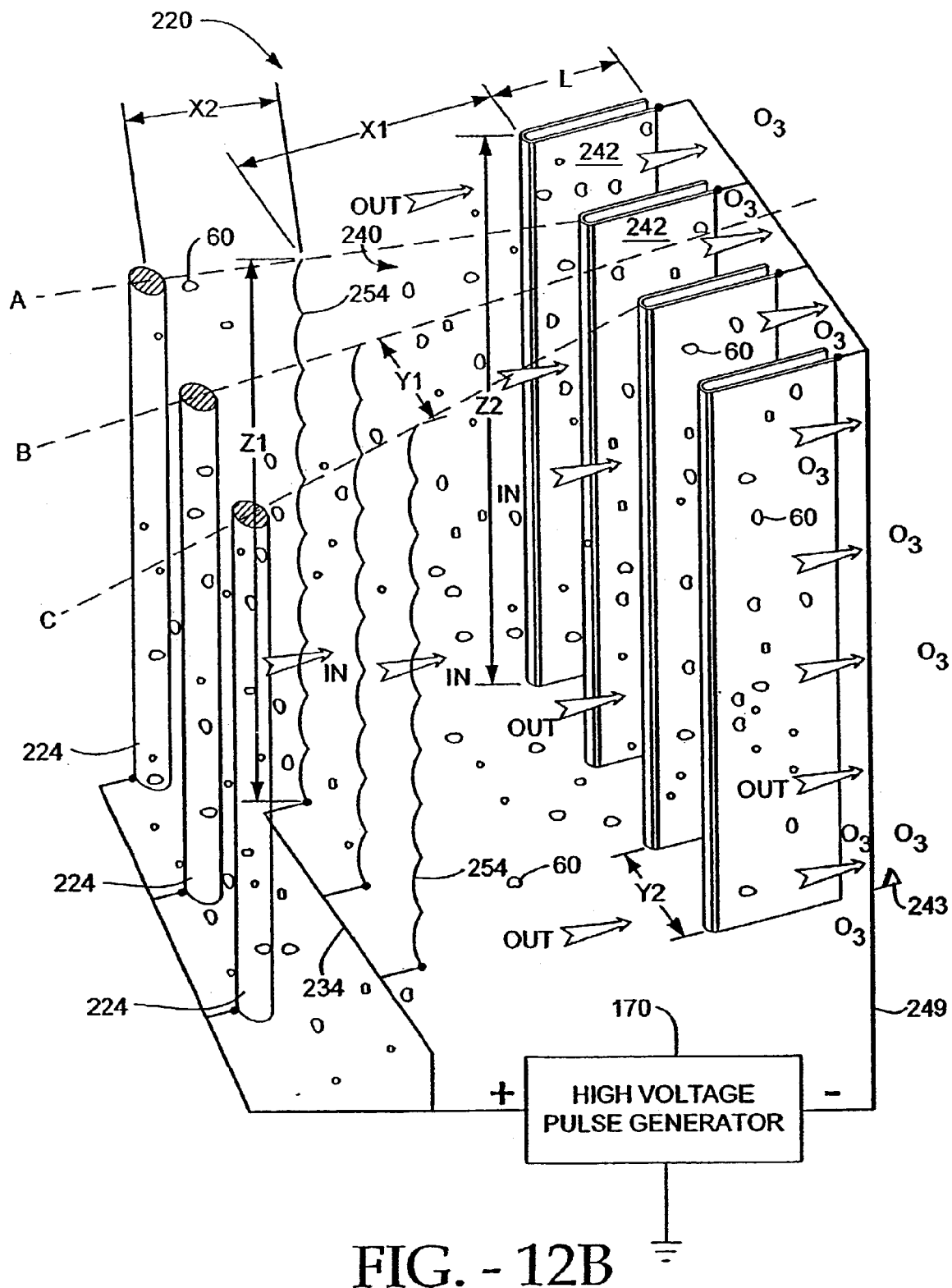

FIG. 12B illustrates that the first array of electrodes 230 may include flat coil wire-shaped electrodes 254. Each flat coil wire-shaped electrode 254 also has a larger surface area than the previously disclosed wire-shaped electrode 232. By way of example only, if the electrode 254 was straightened out, the electrode 254 will have a total length that is preferably 10% longer than the electrode 232. Since the height of the electrode 254 remains at Z1, the electrode 254 has a "kinked" configuration as shown in FIG. 12B. This greater length translates to a larger surface area of the electrode 254 than the surface area of the electrode 232. Accordingly, the electrode 254 will generate and emit a greater number of ions than electrode 232. It is to be understood that an alternative embodiment of FIG. 12B can exclude the focus electrodes and be within the spirit and scope of the invention.

Figure 12C:
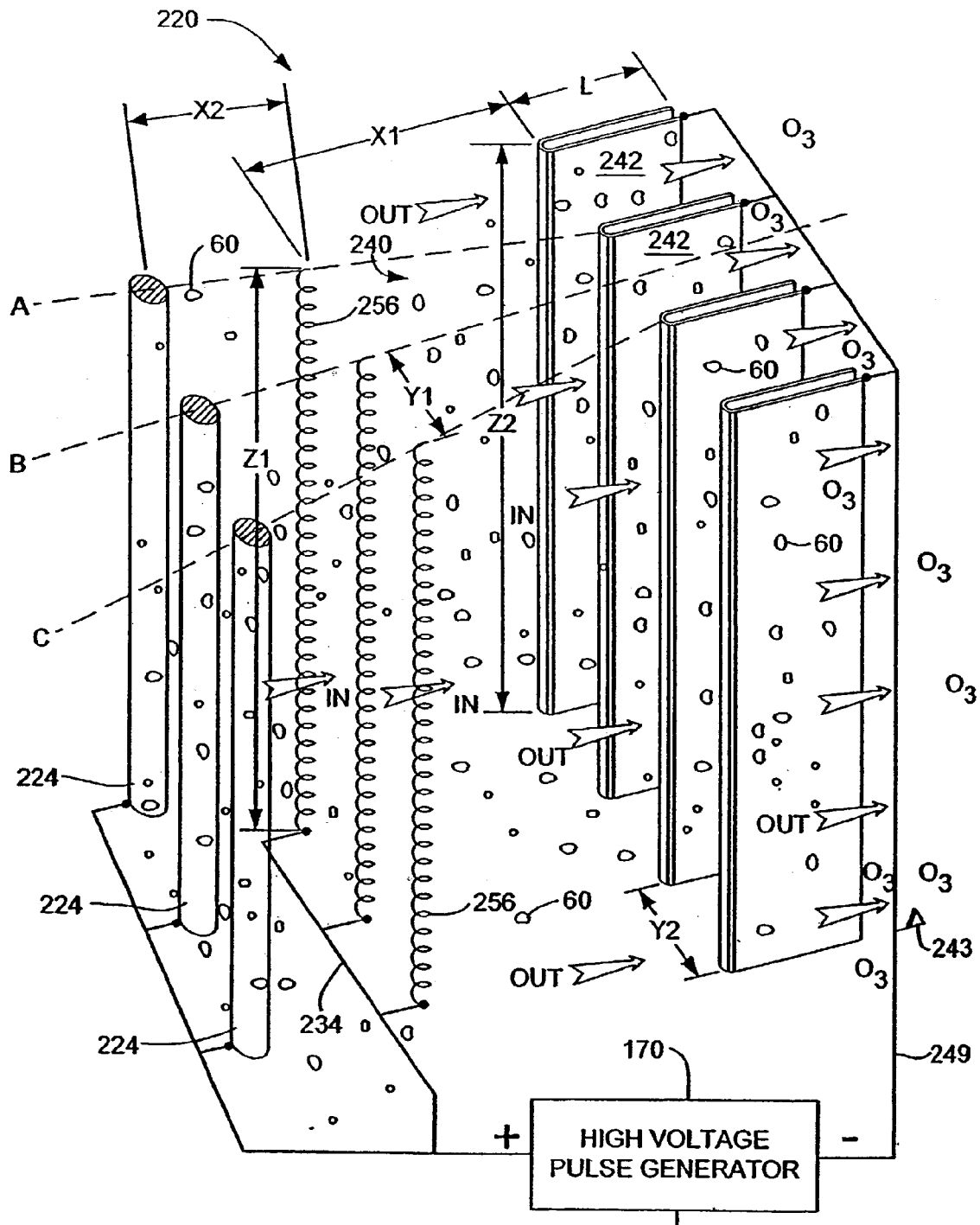

FIG. 12C illustrates that the first array of electrodes 230 may also include coiled wire-shaped electrodes 256. Again, the height Z1 of the electrodes 256 is similar to the height Z1 of the previously described electrodes 232. However, the total length of the electrodes 256 is greater than the total length of the electrodes 232. In a preferred embodiment, if the coiled electrode 256 was straightened out the electrodes 256 will have a total length two to three times longer than the wire-shaped electrodes 232. Thus, the electrodes 256 have a larger surface area than the electrodes 232, and generate and emit more ions than the first electrodes 232. The diameter of the wire that is coiled to produce the electrode 256 is similar to the diameter of the electrode 232. The diameter of the electrode 256 itself is preferably 1-3 mm, but can be smaller in accordance with the diameter of first emitter electrode 232. The diameter of the electrode 256 shall remain small enough so that the electrode 256 has a high emissivity and is an ion emitting surface. It is to be understood that an alternative embodiment of FIG. 12C can exclude the focus electrodes and be within the spirit and scope of the invention.

The electrodes 252, 254 and 256 shown in FIGS. 12A-12C may be incorporated into any of the electrode assembly 220 configurations previously disclosed in this application.

As described supra, the use of one or more interstitial electrodes improves the overall performance of ion wind devices by increasing charged particle precipitation. These uniquely positioned and energized electrodes may also reduce the discharge of ozone and increase airflow in ion wind devices.

Figure 13:
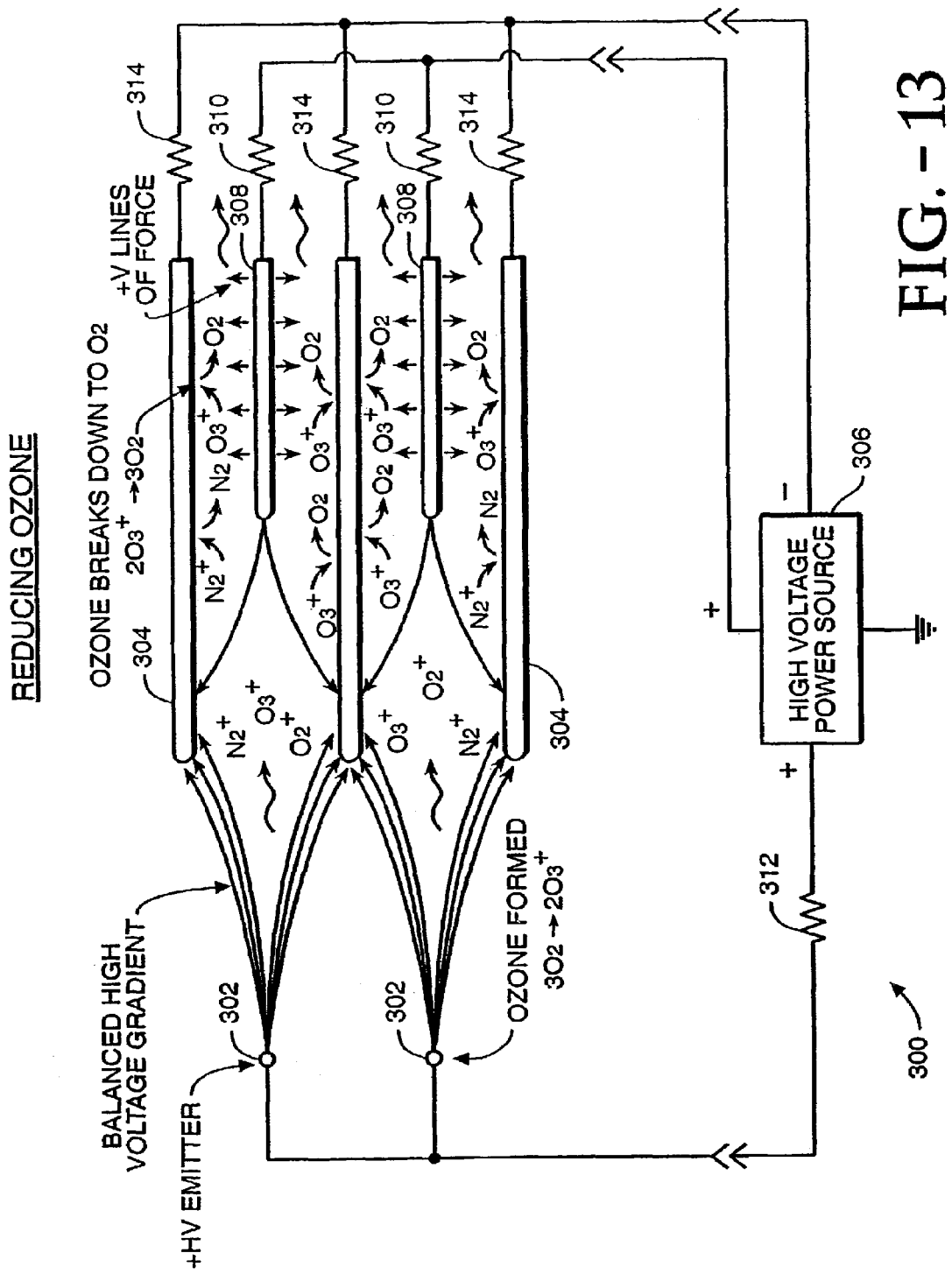
FIG. 13 is a schematic view of an ion wind device of this invention illustrating the use of one or more interstitial electrodes to reduce the discharge of ozone.

FIG. 13 is a schematic view of an ion wind device of this invention illustrating the use of one or more interstitial electrodes to reduce the discharge of ozone. Ion wind device 300 includes one or more emitters 302, collectors 304, and high voltage power source 306, all as discussed in more detail supra. Ozone cations ($O_3^+$) are formed at the positively charged emitter element 302 ($3O_2 \rightarrow 2O_3$). Nitrogen ($N_2^+$) cations and oxygen ($O_2^+$) cations are also produced at the positively charged emitter element 302. When the molecules of $O_3$, $N_2$, and $O_2$ gain or lose valence electrons from their outer shell, their respective sizes change also. For example, non-ionized (neutral) nitrogen has an atomic radius of 0.71 angstroms and oxygen has a radius of 0.66 angstroms. When they gain electrons (become anionic), they increase in size to 1.71 angstrom units for nitrogen and 1.40 angstrom units for oxygen. In the case of an $O_3^+$ ozone ion, if it is abruptly converted to $O_3$ or $O_3^-$ by adding electrons to its L (2p) shell using a high voltage potential it will radically increase in size, become even more unstable, and convert back to oxygen ($2 O_3^+ \rightarrow 3 O_2^-$). Placing a charged interstitial electrode 308 downstream in the ion wind apparatus accelerates the ozone cations toward the negatively charged collector electrode 304 where the cations will receive one or more valence electrons to abruptly convert them to a balanced ion or to an anion. Some of the ozone cations will contact the leading edge and surface area of the collector electrode 304 and convert to oxygen without the need for acceleration. However, very few will actually make contact with the negatively charged collector. The down line electrode(s) 308 may be charged with any positive pulsed or DC voltage with respect to the collector from +00 volts to +10,000 volts depending upon the physical configuration of the array and the specific emitter and collector voltages in use. A grounded or negatively charged plate will also act as a direct contact breakdown source to the ozone cation. However, like the random contact made by the ozone cation upon the collector plates, there is the same likelihood that only minimal and random contact is made with the down line electrodes. The more positive the voltage potential applied to the down line electrodes without corona occurring, the more effective the rate of chemical conversion to oxygen becomes. Also, a great deal of the nitrogen cation $N_2^+$ is balanced or converted to an anion $N_2^-$. This is desirable in most ion wind devices to minimize the output of breathable cations, which are typically nitrogen molecules that make up almost 80% of the atmosphere.

The down line electrode 308 may be in the form of either one or more conductive rods or a thin plate material. The differential voltage between the down line electrode should not be high enough to create high voltage break over or corona current since this may create additional ozone as well as damage high voltage circuitry. Each electrode is preferably equipped with a high voltage series resistor 310 (e.g., between one and ten megohms) to limit peak current and inhibit break over. The higher the series resistance the less likelihood of voltage break over and incidence of corona current. However, higher resistance also will inhibit electron transfer between voltage source and free ions. An optimum series resistance is dependent upon selected applied voltages, electrode spacing and desired effect. Typically a one megohm emitter series resistor 312, ten megohm collector series resistor 314 and a 4 megohm down line electrode series resistor 310 are desirable when using +8 KV, −8 KV and +4 KV respectively in a 1"×1"×½" array.

The down line electrode 308 is preferably positioned equidistantly from and between the collector plates 304. The position of the electrode from the rear (air discharge) point of the collector plates toward the emitter element is voltage dependent. The down line electrode should not be positioned and/or charged in such a manner as to distort (bend) the primary voltage gradient. Typically, a charged interstitial electrode configuration should not exceed +4,000 volts DC and extend beyond the halfway distance from the end of the collector plates 304 toward the emitter element 302. Deeper upstream penetration toward the emitter element is possible at reduced electrode voltage. However, positioning of any electrode, charged or not, too close to the leading edge of the collector plates will alter primary balanced lines of force with the result of reduced airflow. Utilizing a poorly filtered DC voltage source for the collector and down line electrode is also desirable. The ripple voltage acts to further excite the accelerated movement of the ozone cation resulting in additional molecular disassociation.

Figure 14:
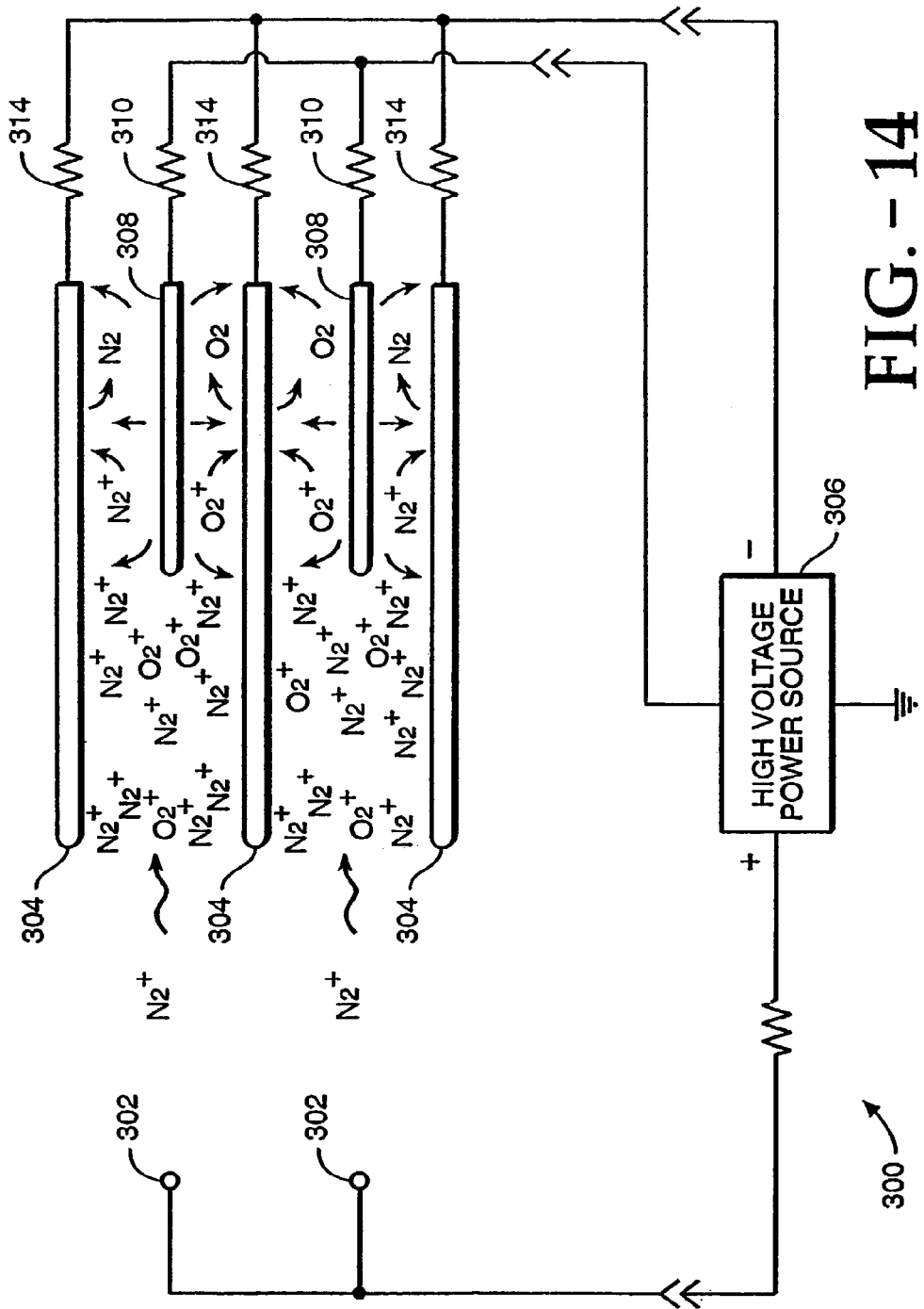
FIG. 14 is a schematic view of an ion wind device of this invention illustrating the use of one or more interstitial electrodes to increase airflow by de-ionizing charged molecules responsible for resisting forces in the airstream.

FIG. 14 is a schematic view of an ion wind device of this invention illustrating the use of one or more interstitial electrodes to increase airflow by de-ionizing charged molecules responsible for resisting forces in the airstream. Ion wind devices do not rely upon a motorized fan to force charged airflow through a collector array. Instead, airflow is achieved by charging air molecules, $N_2$ and $O_2$, and repelling the air ions within a balanced voltage gradient, while simultaneously attracting some of them to an oppositely charged element (collector). Therefore, the existence of a heavily populated cationic field of molecules downstream from the source of cation production inhibits unrestricted airflow. The down line electrode 308 reduces the like-charge effect by accelerating a large amount of the nitrogen cations toward a negatively charged field and collector element 304 where their valence may be balanced or reversed. The acceleration of atmospheric ions toward an oppositely charged collector 304 is far more effective than random contacts with a grounded or negatively charged electrode.

Figure 15:
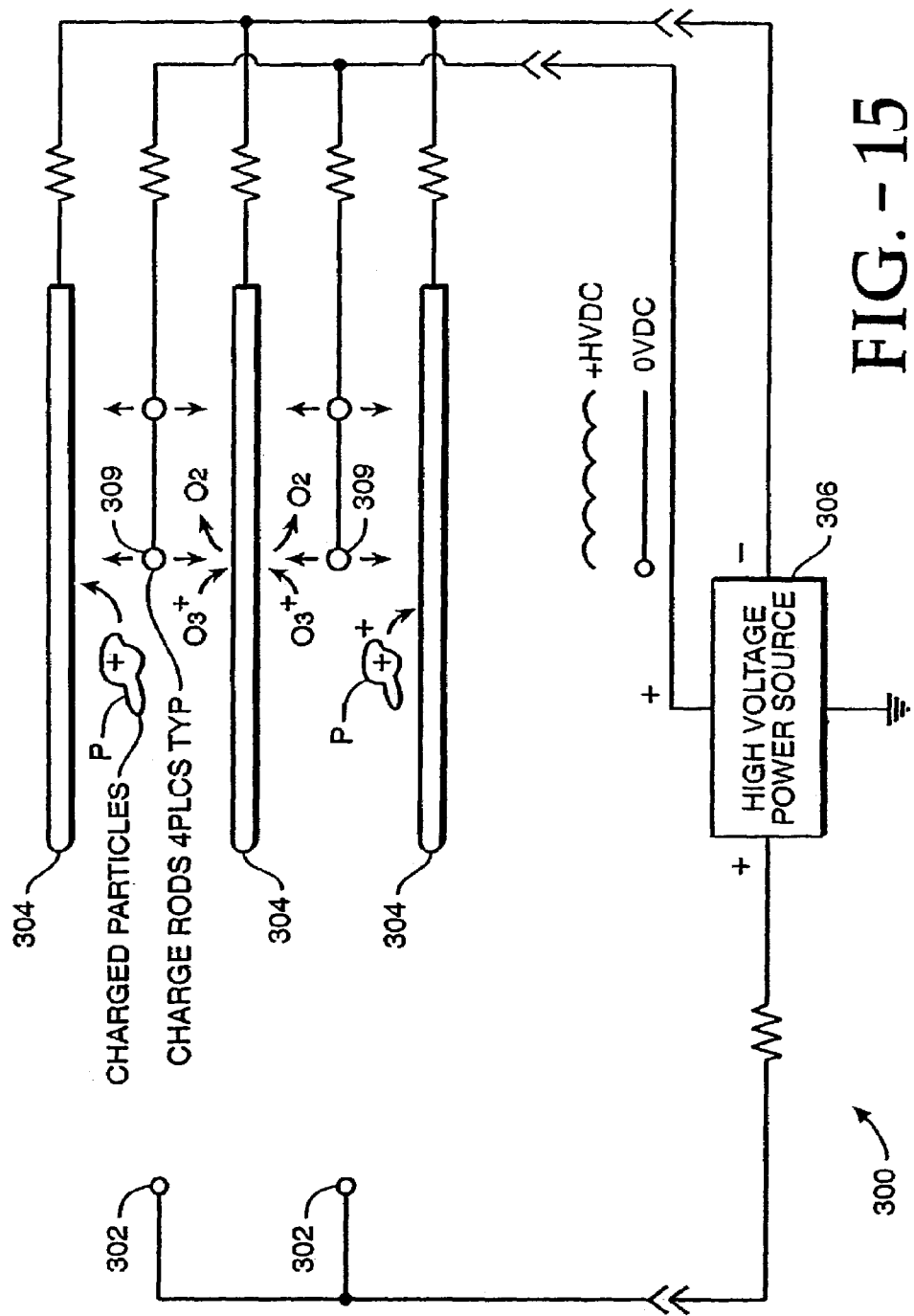
FIG. 15 is a schematic view of an ion wind device of this invention illustrating the use of one or more interstitial electrodes to increase airflow by improving the precipitation efficiency of charged particles.

FIG. 15 is a schematic view of an ion wind device of this invention illustrating the use of one or more interstitial electrodes to increase airflow by improving the precipitation efficiency of charged particles. As air is drawn into the emitter area of the ion wind device, so too are small particles P of pollen, airborne viruses, spores, miscellaneous air pollution, etc. These materials, particularly in the size range of 0.1 micron to 10 microns, are also either directly ionized or are attached to the charged oxygen and nitrogen. By virtue of their relatively large mass and momentum induced by acceleration from transverse electric fields many are collected upon the surface of the oppositely charged collector plates 304 before they can exit the array. To increase the number of collected charged particles, various schemes have been proposed. Principally, increasing collector surface area, increasing collector surface voltage level, and reducing air velocity have been the most common methods used by ion wind devices.

The addition of a positively charged down line electrode 309 exerts a repelling force upon the positively charged particles P. A positive high voltage field accelerates a positively charged particle, or particle cluster, toward the negatively charged plate 304. Typically, a collector plate area A must be squared ($A^2$) to double particle precipitation efficiently. The addition of a down line +4 KV plate electrode or rod 309 having an area of less than A/2 will also double particle precipitation efficiency. As the air stream is evacuated more quickly of charged particles, gaseous ions are allowed to flow with less opposition. The result is increased airflow.

Figure 16:
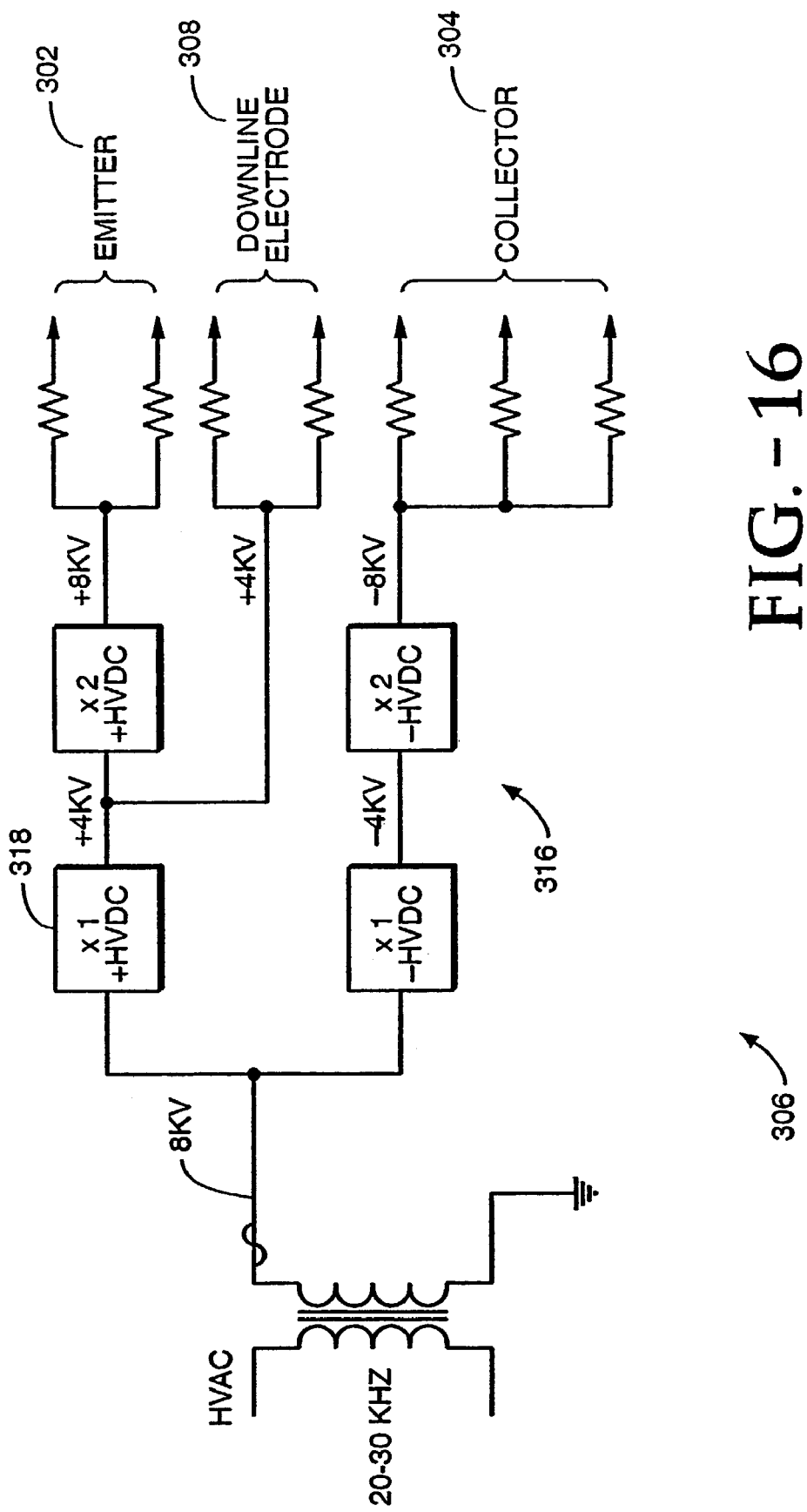
FIG. 16 is a schematic view of a high voltage power source for ion wind devices of this invention.

FIG. 16 is a schematic view of a typical high voltage power source for the present invention. Power source 306 includes a dual positive and negative half wave voltage multiplier 316 operating with an input frequency of 20,000 Hz or above. Typical output voltages are +8 KV, −8 KV and +4 KV (which is derived from the first stage 318 of the two-stage positive voltage multiplier). Multiplier capacitance values are typically between 220 pf and 470 pf at 10 KV or greater depending upon the desired voltage and ripple effect.

Figure 17:
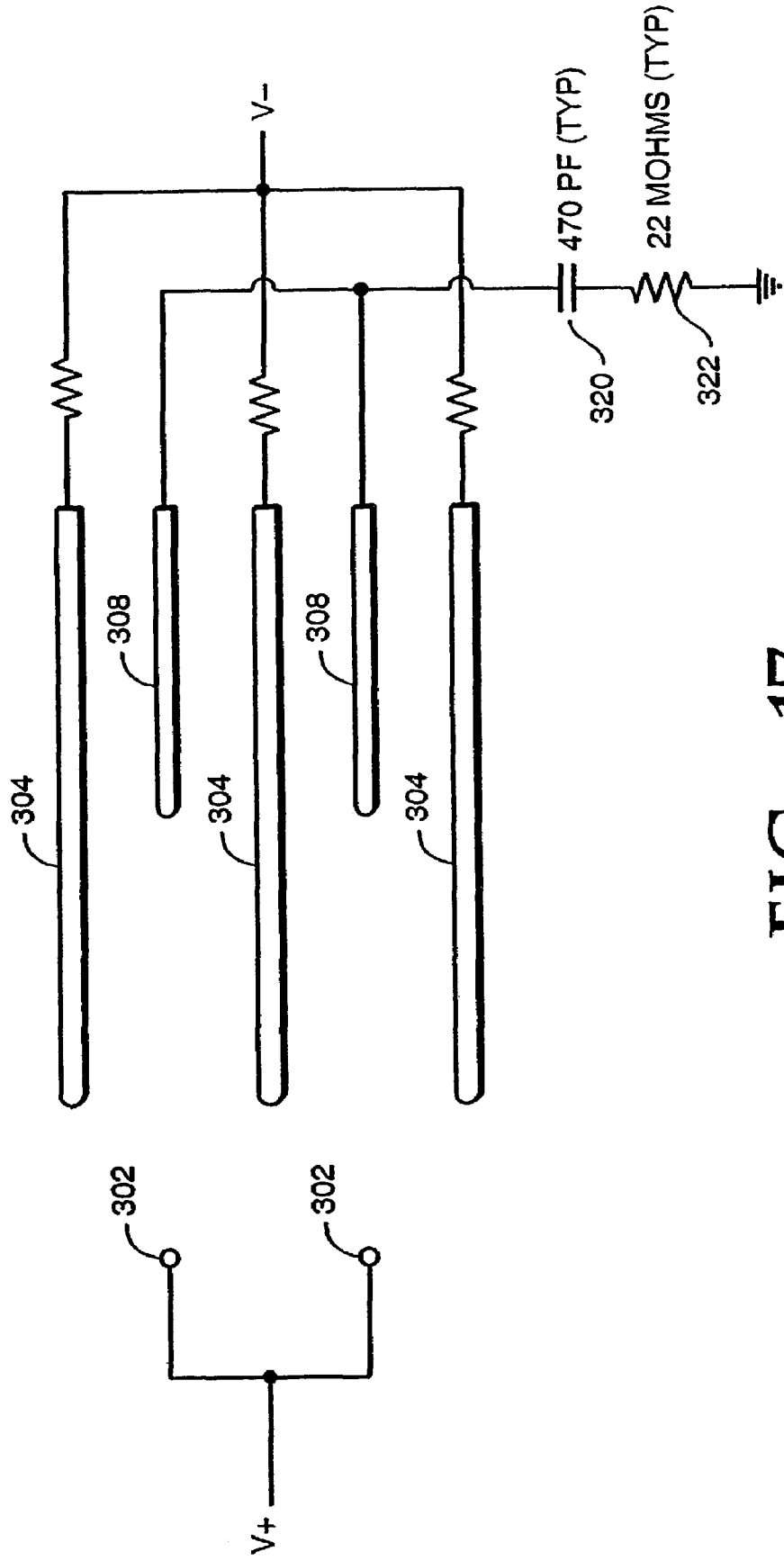
FIG. 17 is a schematic view of an alternate wiring option for an interstitial electrode of this invention.

FIG. 17 is a schematic view of an alternate wiring option for an interstitial electrode. A down line electrode plate or rod element which is isolated from ground or a voltage source will accumulate a surface charge proportional to air stream ion polarity and density. Also, a down line electrode which is connected to ground via a high voltage capacitor will accumulate a large surface charge proportional to air stream ion polarity and density. This may be achieved by the direct connection of one or more interstitial electrodes 308 to a 470 pf HV capacitor 320 in series with a 20M ohm resistor 322 to ground. Instead of using a direct ground or an active voltage source to the additional electrodes, this configuration permits the electrodes to float to a positive voltage level and behave the same as if a direct DC bias were applied to them. This serves to increase precipitation efficiency and airflow, while simultaneously reducing ozone and power consumption.

Finally, reversing the polarity of emitter, collector and down line electrodes will have similar benefits as described herein. However, using a negative high voltage emitter source generally increases the production of ozone and irregular plasma envelope emissivity at the primary emitter element.

The foregoing description of the preferred embodiments of the present invention has been provided for the purposes of illustration and description. It is not intended to be exhaustive or to limit the invention to the precise forms disclosed. Many modifications and variations will be apparent to the practitioner skilled in the art. Modifications and variations may be made to the disclosed embodiments without departing from the subject and spirit of the invention as defined by the following claims. Embodiments were chosen and described in order to best describe the principles of the invention and its practical application, thereby enabling others skilled in the art to understand the invention, the various embodiments and with various modifications that are suited to the particular use contemplated. It is intended that the scope of the invention be defined by the following claims and their equivalents.

What is claimed as invention is:

1. An air treatment apparatus comprising:
   a housing having an elongated shape, the housing extending along a longitudinal axis, the housing having:
   (a) an air inlet portion;
   (b) an air outlet portion positioned in a downstream direction relative to the air inlet portion, the air inlet portion and the air outlet portion being positioned on a lateral axis which intersects with the longitudinal axis;
   (c) an emitter electrode support;
   (d) a collector electrode support, the collector electrode support having at least one housing wall which defines an elongated slot extending substantially parallel to the longitudinal axis; and (e) an interstitial electrode support;

at least one wire-shaped elongated emitter electrode supported by the emitter electrode support;

a collector electrode unit having:
  (a) a base portion spaced apart from a top portion, the top portion having a handle, the base portion being configured to be slidably inserted into the elongated slot; and
  (b) a plurality of elongated, plate-shaped collector electrodes, each one of the elongated, plate-shaped collector electrodes having:
    (i) one end coupled to the base portion;
    (ii) another end coupled to the top portion;
    (iii) an elongated body extending between the ends; and
    (iv) a first edge and a second edge, the second edge being positioned in the downstream direction relative to the first edge when the base portion of collector electrode unit is inserted into the elongated slot of the housing;

a voltage generator, electrically coupled to the emitter electrode and the collector electrodes to create a flow of air in the downstream direction; and at least one elongated interstitial electrode supported by the interstitial electrode support, the interstitial electrode being located between at least two of the collector electrodes, said interstitial electrode having:
  (a) a plurality of spaced-apart ends, the ends being positioned along an axis which is substantially parallel to the longitudinal axis; and
  (b) a portion positioned in the downstream direction relative to the first edges of the two collector electrodes when the base portion of collector electrode unit is inserted into the elongated slot of the housing.

2. The air treatment apparatus of claim 1 wherein said plurality of collector electrodes are fin shaped and said interstitial electrode is wire shaped.

3. The air treatment apparatus of claim 1 wherein said plurality of collector electrodes are fin shaped and said interstitial electrode is rod shaped.

4. The air treatment apparatus of claim 1 wherein said interstitial electrode is located midway between the two collector electrodes.

5. The air treatment apparatus of claim 1 wherein said interstitial electrode is one of wire-shaped and rod-shaped with the interstitial electrode located substantially along a line between trailing portions of the two collector electrodes.

6. The air treatment apparatus of claim 1 wherein said interstitial electrode and said wire-shaped elongated emitter electrode are electrically connected.

7. The air treatment apparatus of claim 1 wherein said interstitial electrode and said plurality of elongated, plate-shaped collector electrodes have the same polarity when said voltage generator is energized.

8. The air treatment apparatus of claim 1 wherein said wire-shaped elongated emitter electrode has a first sign potential and can charge particles with the same sign potential, and said plurality of elongated, plate-shaped collector electrodes and said interstitial electrode both have an opposite sign potential such that said interstitial electrode can deflect charged particles toward said plurality of elongated, plate-shaped collector electrodes.

9. The air treatment apparatus of claim 1 wherein said wire-shaped elongated emitter electrode emits ions when said voltage generator is energized, and wherein said interstitial electrode can neutralize the ions emitted by said wire-shaped elongated emitter electrode.

10. The air treatment apparatus of claim 1 wherein said wire-shaped elongated emitter electrode emits positive ions when said voltage generator is energized, and wherein said elongated interstitial electrode can neutralize the positive ions emitted by said wire-shaped elongated emitter electrode by emitting negative ions.

11. The air treatment apparatus of claim 1 wherein said collector electrode unit is removable by a user.

12. The air treatment apparatus of claim 1 wherein said collector electrode unit is removable by a user for cleaning.

13. The air treatment apparatus of claim 1 wherein the housing is configured to hold an electro-kinetic air transporter-conditioner.

14. The air treatment apparatus of claim 1 wherein said plurality of collector electrodes and said interstitial electrode are substantially a same length.

15. The air treatment apparatus of claim 1 wherein the housing has a base and a top.

16. The air treatment apparatus of claim 15 wherein the elongated slot extends through the top.

17. The air treatment apparatus of claim 1 which includes an electrode cleaning member supported by the housing.

18. The air treatment apparatus of claim 1 wherein said elongated interstitial electrode is one of wire-shaped or rod-shaped.

19. The air treatment apparatus of claim 1 wherein said wire-shaped elongated emitter electrode is an ion emitter and the plurality of elongated, plate-shaped collector electrodes are collectors of particulate matter.

20. The air treatment apparatus of claim 1 wherein said wire-shaped elongated emitter electrode is positively charged and the plurality of elongated, plate-shaped collector electrodes are negatively charged.

21. The air treatment apparatus of claim 20 wherein said wire-shaped elongated emitter electrode is pin-shaped.

22. The air treatment apparatus of claim 1 wherein said elongated interstitial electrode is at least one of: positive potential, negative potential, floating potential, and grounded.

23. The air treatment apparatus of claim 1 wherein said elongated interstitial electrode has a potential sign which is the opposite to the potential sign of the plurality of elongated, plate-shaped collector electrodes.

24. The air treatment apparatus of claim 1 wherein said elongated interstitial electrode includes a plurality of interstitial electrode elements.

25. The air treatment apparatus of claim 1 wherein said elongated interstitial electrode includes a plurality of interstitial electrode elements which can establish a voltage gradient when energized.

26. The air treatment apparatus of claim 1 wherein said elongated interstitial electrode is electrically connected to said wire-shaped elongated emitter electrode.

27. An air treatment apparatus comprising:

a housing having an elongated shape, the housing extending along a longitudinal axis, the housing having:
  (a) an air inlet portion;
  (b) an air outlet portion positioned in a downstream direction relative to the air inlet portion, the air inlet portion and the air outlet portion being positioned on a lateral axis which intersects with the longitudinal axis;
  (c) an emitter electrode support;
  (d) a collector electrode support, the collector electrode support having at least one housing wall which defines an elongated slot extending substantially parallel to the longitudinal axis; and
(e) an interstitial electrode support;
at least one wire-shaped elongated emitter electrode supported by the emitter electrode support;
a collector electrode unit having:
(a) a base portion spaced apart from a top portion, the top portion having a handle, the base portion being configured to be slidably inserted into the elongated slot; and
(b) a plurality of elongated, plate-shaped collector electrodes, each one of the elongated, plate-shaped collector electrodes having:
(i) one end coupled to the base portion;
(ii) another end coupled to the top portion;
(iii) an elongated body extending between the ends; and
(iv) a first edge and a second edge, the second edge being positioned in the downstream direction relative to the first edge when the base portion of collector electrode unit is inserted into the elongated slot of the housing;
a potential generator, electrically coupled to the emitter electrode and the collector electrodes to create a flow of air in the downstream direction; and
at least one elongated interstitial electrode supported by the interstitial electrode support, the interstitial electrode being located between at least two of the collector electrodes, said interstitial electrode having:
(a) a plurality of spaced-apart ends, the ends being positioned along an axis which is substantially parallel to the longitudinal axis; and
(b) a portion positioned in the downstream direction relative to the first edges of the two collector electrodes when the base portion of collector electrode unit is inserted into the elongated slot of the housing; and
circuitry supported by the housing, the circuitry being operable with the potential generator to cause:
(a) the wire-shaped elongated emitter electrode to have a potential of a first sign operable to cause particles in the air to be charged with a first sign charge;
(b) each one of the elongated, plate-shaped collector electrodes to have a potential of a second sign which is opposite of the first sign; and
(c) the elongated interstitial electrode to have a potential of the first sign such that the elongated interstitial electrode is operable to deflect the charged particles toward the elongated, plate-shaped collector electrodes.

28. The air treatment apparatus of claim 27 wherein said plurality of elongated, plate-shaped collector electrodes are fin shaped and said elongated interstitial electrode is wire shaped.

29. The air treatment apparatus of claim 27 wherein said plurality of elongated, plate-shaped collector electrodes are fin shaped and said elongated interstitial electrode is rod shaped.

30. The air treatment apparatus of claim 27 wherein said elongated interstitial electrode is located midway between the plurality of elongated, plate-shaped collector electrodes.

31. The air treatment apparatus of claim 27 wherein said elongated interstitial electrode is one of wire and rod shaped with the elongated interstitial electrode located substantially along a line between trailing portions of the plurality of elongated, plate-shaped collector electrodes.

32. The air treatment apparatus of claim 27 wherein said elongated interstitial electrode and said plurality of elongated, plate-shaped collector electrodes are electrically connected.

33. The air treatment apparatus of claim 27 wherein said elongated interstitial electrode and said plurality of elongated, plate-shaped collector electrodes have a same polarity when said potential generator is energized.

34. The air treatment apparatus of claim 27 which includes at least one electrode cleaning member supported by the housing.

35. The air treatment apparatus of claim 27 which includes additional circuitry supported by the housing, the additional circuitry operable with the voltage generator to cause: (a) said wire-shaped elongated emitter electrode to emits ions when said potential generator is energized; and (b) said elongated interstitial electrode to neutralize the ions emitted by said wire-shaped elongated emitter electrode.

36. The air treatment apparatus of claim 27 wherein said elongated interstitial electrode is wire-shaped or rod-shaped.

37. An air treatment apparatus comprising:
a housing having an elongated shape, the housing extending along a longitudinal axis, the housing having:
(a) an air inlet portion;
(b) an air outlet portion positioned in a downstream direction relative to the air inlet portion, the air inlet portion and the air outlet portion being positioned on a lateral axis which intersects with the longitudinal axis;
(c) an emitter electrode support;
(d) a collector electrode support, the collector electrode support having at least one housing wall which defines an elongated slot extending substantially parallel to the longitudinal axis; and
(e) an interstitial electrode support;
at least one wire-shaped elongated emitter electrode supported by the emitter electrode support, the elongated emitter electrode being operable to generate a first electric field;
a collector electrode unit having:
(a) a base portion spaced apart from a top portion, the top portion having a handle, the base portion being configured to be slidably inserted into the elongated slot; and
(b) a plurality of elongated, plate-shaped collector electrodes, the elongated, plate-shaped collector electrodes, each one of the elongated, plate-shaped collector electrodes being operable to generate a second electric field, each one of the elongated, plate-shaped collector electrodes having:
(i) one end coupled to the base portion;
(ii) another end coupled to the top portion;
(iii) an elongated body extending between the ends; and
(iv) a first edge and a second edge, the second edge being positioned in the downstream direction relative to the first edge when the base portion of collector electrode unit is inserted into the elongated slot of the housing;
a voltage generator, electrically coupled to the emitter electrode and the collector electrodes to create a flow of air in the downstream direction, the flow of air having a plurality of particles; and
at least one elongated interstitial electrode supported by the interstitial electrode support, the elongated interstitial electrode being operable to generate a third electric field, the elongated interstitial electrode being located between at least two of the collector electrodes, the interstitial electrode having:
- (a) a plurality of spaced-apart ends, the ends being positioned along an axis which is substantially parallel to the longitudinal axis; and
- (b) a portion positioned in the downstream direction relative to the first edges of the two collector electrodes when the base portion of collector electrode unit is inserted into the elongated slot of the housing; and circuitry supported by the housing, the circuitry being operable with the voltage generator to control the first and second electric fields relative to the third electric field so as to cause the interstitial electrode to direct at least one of the particles toward at least one of the two collector electrodes.

38. The air treatment apparatus of claim 37, wherein said elongated interstitial electrode is located midway between said two of collector electrodes.

39. The air treatment apparatus of claim 37, wherein saidfirst emitter electrode and the plurality of collector electrodes have opposite polarities when said voltage generator is energized.

40. The air treatment apparatus of claim 39, wherein said wire-shaped elongated emitter electrode emits ions to charge particles contained with the airflow.

41. The air treatment apparatus of claim 39, wherein said elongated interstitial electrode and said plurality of elongated, plate-shaped collector electrodes have a same polarity when said voltage generator is energized.

42. The air treatment apparatus of claim 41, wherein said elongated interstitial electrode pushes or repels the a plurality of the particles towards said plurality of elongated, plate-shaped collector electrodes.

43. The air treatment apparatus of claim 37, wherein: (a) the first electric field corresponds to a first electric charge sign; (b) the second electric field corresponds to a second electric charge sign which is opposite the first electric charge sign; and (c) the third electric field corresponds to the first electric charge sign.

44. The air treatment apparatus of claim 37, wherein: (a) the first electric field corresponds to a first electric charge sign; (b) the second electric field corresponds to a second electric charge sign which is opposite the first electric charge sign; and (c) the third electric field corresponds to the second electric charge sign.

* * * * *